United States Patent [19]
Czernilofsky et al.

[11] Patent Number: 5,854,004
[45] Date of Patent: Dec. 29, 1998

[54] PROCESS FOR SCREENING SUBSTANCES CAPABLE OF MODULATING A RECEPTOR-DEPENDENT CELLULAR SIGNAL TRANSMISSION PATH

[75] Inventors: Armin Peter Czernilofsky; Adolf Himmler; Christian Stratowa; Ulrike Weyer, all of Vienna; Herbert Lamche, Alland; Renate Schafer, Vienna, all of Austria

[73] Assignee: Boehringer Ingleheim GmbH, Ingelheim am Rhein, Germany

[21] Appl. No.: 244,434

[22] PCT Filed: Nov. 25, 1992

[86] PCT No.: PCT/EP92/02718

§ 371 Date: May 25, 1994

§ 102(e) Date: May 25, 1994

[87] PCT Pub. No.: WO93/11257

PCT Pub. Date: Jun. 10, 1993

[30] Foreign Application Priority Data

Nov. 25, 1991 [DE] Germany .......................... 41 38 621.3

[51] Int. Cl.⁶ .......................... C12Q 1/68; G01N 33/566
[52] U.S. Cl. .................... 435/7.21; 435/6; 435/8
[58] Field of Search .......................... 435/7.21, 8, 320.1, 435/240.1, 325, 6

[56] References Cited

U.S. PATENT DOCUMENTS 5,202,257  4/1993  Heinemann et al. ................. 435/252.3
5,462,856  10/1995  Lerner et al. .......................... 435/7.21

FOREIGN PATENT DOCUMENTS 0 569 240  11/1993  European Pat. Off. .
WO 91/15602  10/1991  WIPO .

OTHER PUBLICATIONS

Angel et al., "Phorbol Ester–Inducible Genes Contain a Common Cis Element Recognized by a TPA–Modulated Trans–Acting Factor," *Cell* 49:729–739 (1987)

Billah et al., "Regulation of Phospholipase D in HL–60 Granulocytes," *J. Biol. Chem.* 264(15):9069–9076 (1989).

Brasier et al., "Optimized Use of the Firefly Luciferase Assay as a Reporter Gene in Mammalian Cell Lines," *BioTechniques* 7(10):1116–1122 (1989).

Deutsch et al., "Cyclic AMP and phorbol ester–stimulated transcription mediated by similar DNA elements that bind distinct proteins," *Proc. Natl. Acad. Sci. USA* 85:7922–7926 (1988).

De Wet et al., "Cloning of Firefly luciferase cDNA and the expression of active Luciferase in *Escherichia coli,*" *Proc. Natl. Acad. Sci. USA* 82:7870–7873 (19850

De Wet et al., "Firefly Luciferase Gene: Structure and Expression in Mammalian Cells," *Mol. Cell Biol.* 7(2):725–737 (1987).

Dohlman et al., "Model Systems for the Study of Seven–Transmembrane–Segment Receptors," *Ann. Rev. Biochem.* 60:653–688 (1991).

Doods and van Meel, *Receptor Data for Biological Experiments* (ed. Ellis Horwood), pp. 13–179, 190–289 (1991).

Gerard et al., "The Human Neurokinin A (Substance K) Receptor," *J. Biol. Chem.* 265(33):20455–20462 (1990).

Grandy et al., "Multiple human $D_5$ dopamine receptor genes: A functional receptor and two pseudogenes," *Proc. Natl. Acad. Sci. USA* 88:9175–9179 (1991).

Gritz and Davis, "Plasmid–encoded hygromycin B resistance: the sequence of hygromycin B phosphotransferase gene and its expression in *Escherichia coli* and *Saccharomyces cerevisiae,"Gene* 25:179–188 (1983).

Housley M.D., "'Crosstalk': a pivotal role for protein kinase C in modulating relationships between signal transduction pathways," *Eur. J. Biochem.* 195:9–27 (1991).

Julius et al., "The 5HT2 receptor defines a family of structurally distinct but functionally conserved serotonin receptors," *Proc. Natl. Acad. Sci. USA* 87:928–932 (1990).

Karin, M., "Complexities of Gene Regulation by cAMP," *TIG* 5(3):65–67 (1989).

King et al., "Control of Yeast Mating Signal Transduction by a Mammalian $\beta_2$–Adrenergic Receptor and $G_s$ α Subunit," *Science* 250:121–123 (1990).

Leach and Webster, "Commercially Available Firefly Luciferase Reagents," *Methods in Enzymology* 133:51–70 (1986).

Lee et al., "Purified Transcription Factor AP–1 Interacts with TPA–Inducible Enhancer Elements," *Cell* 49:741–752 (1987).

Montmayeur and Borrelli, "Transcription mediated by a cAMP–responsive promoter element is reduced upon activation of dopamine $D_2$ receptors," *Proc. Natl. Acad. Sci. USA* 88:3135–3139 (1991).

Montminy et al., "Regulation of cAMP–inducible genes by CREB," *TINS* 13(5):184–188 (1990).

Mulligan and Berg, "Selection for animal cells that express the *Escherichia coli* gene coding for xanthine–guanine phosphoribosyltransferase," *Proc. Natl. Acad. Sci. USA* 78(4):2072–2076 (1981).

(List continued on next page.)

*Primary Examiner*—David Saunders
*Attorney, Agent, or Firm*—Sterne, Kessler, Goldstein & Fox, P.l.l.c.

[57] ABSTRACT

A process is disclosed for screening substances having a modulating effect on a receptor-dependent signal transmission path in mammal cells. Test cells are used transformed with a reporter gene and with a regulatory sequence functionally linked thereto sensitive to the $IP_3$/DAG concentration, as well as with a coding DNA for a receptor coupled to the phospholipase effector system, in particular a G protein-coupled receptor. The use of reference cells without receptor DNA and reference cells with specificity for the adenylate cyclase effector system allows substances to be identified having potential pharmacological action and specificity for a determined receptor-dependent signal transmission path.

19 Claims, 48 Drawing Sheets

OTHER PUBLICATIONS

Pritchett et al., "Structure and functional expression of cloned rat serotonin 5HT–2 receptor," *EMBO J.* 7(*13*):4135–4140 (1988).

Sassone–Corsi et al., "Cross–talk in signal transduction: TPA–inducible factor jun/AP–1 activates cAMP–responsive enhancer elements," *Oncogene* 5:427–431 (1990).

Simon et al., "Diversity of G Proteins in Signal Transduction," *Science* 252:802–808 (1991).

Southern and Berg, "Transformation of Mammalian Cells to Antibiotic Resistance with a Bacterial Gene Under Control of the SV40 Early Region Promoter," *J. Mol. Appl. Gen.* 1(*4*):327–341 (1982).

Subramani and DeLuca, "Application of the Firefly Luciferase as a Reporter Gene," *Genetic Engineering Principles and Methods*, J.K. Sedlow ed. (Plenum Press N.Y.), Vol. 10:75–89 (1987).

Sudgen et al., "A Vector that Replicates as a Plasmid and Can be Efficiently Selected in B–Lymphoblasts Transformed by Epstein–Barr Virus," *Mol. Cell. Biol.* 5(*2*):410–413 (1985).

Ullrich and Schlessinger, "Signal Transduction by Receptors with Tyrosine Kinase Activity," *Cell* 61:203–212 (1990).

Voraberger et al., "Cloning the Human Gene for Intercellular Adhesion Molecule 1 and Analysis of its 5'–Regulatory Region," *J. Immunol.* 147(*8*):2777–2786 (1991).

Zhou et al., "Cloning and expression of human and rat $D_1$ dopamine receptors," *Nature* 347:76–80 (1990).

Anderson J., "The Cellular Information Highway," *The Washington Post*:A4 (Oct. 11, 1994).

BglII - BamHI Fragment after PCR of pX1

```
                                                                              EBI-2983
                                                                    ........>

(BglII)  NotI  XhoI  KpnI   HpaI   SalI
         GATCT GCGGCCGCCT CGAGGGTACC GTTAACGTCG ACAAACCCCG CCGAGCGTCT
             A CGCCGGCGGA GCTCCCATGG CAATTGCAGC TGTTTGGGGC GGCTCGCAGA

EcoRI             Thymidin Kinase Promoter
         ..->
         TGTCATTGGC GAATTCGAAC ACGCAGATGC AGTCGGGGCG GCGCGGTCCG AGGTCCACTT
         ACAGTAACCG CTTAAGCTTG TGCGTCTACG TCAGCCCCGC CGCCCAGGC TCCAGGTGAA "TATA"                      +1 (RNA Start)
         CGCATATTAA GGTGACGCGT GTGGCCTCGA ACACCGAGCG ACCCTGCAGC GACCCGCTTA
         GCGTATAATT CCACTGCGCA CACCGGAGCT TGTGGCTCGC TGGGACGTCG CTGGGCGAAT
                                                                       <--
                                                                             EBI-2984

HindIII XbaI   SpeI    SacI (BamHI)
         ACAGGCGTCAAGCTTTCTAGA ACTAGTGAGC TCG
         TGTCGCAGTTCGAAAGATCT TGATCACTCG AGCCTAG
         <
         EBI-2984
```

FIG. 2

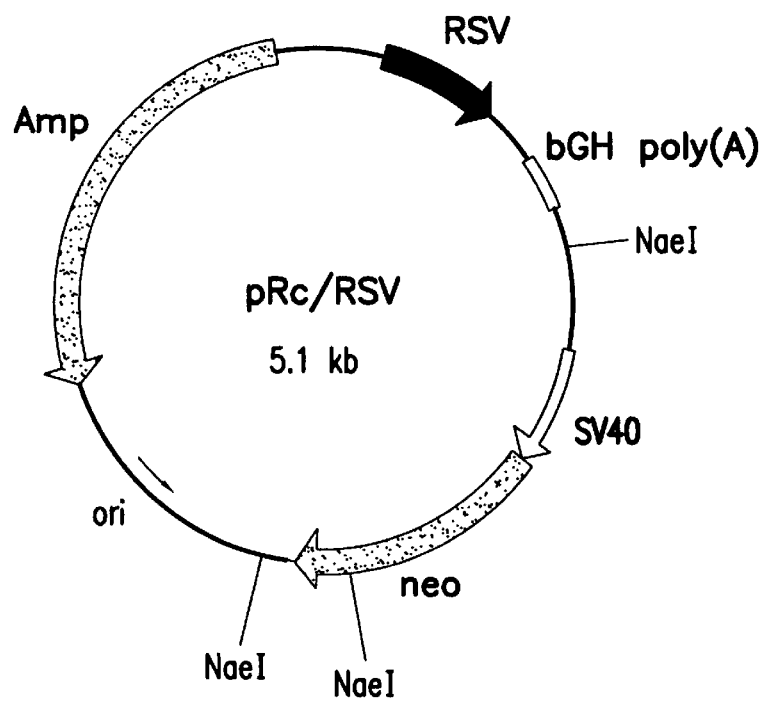
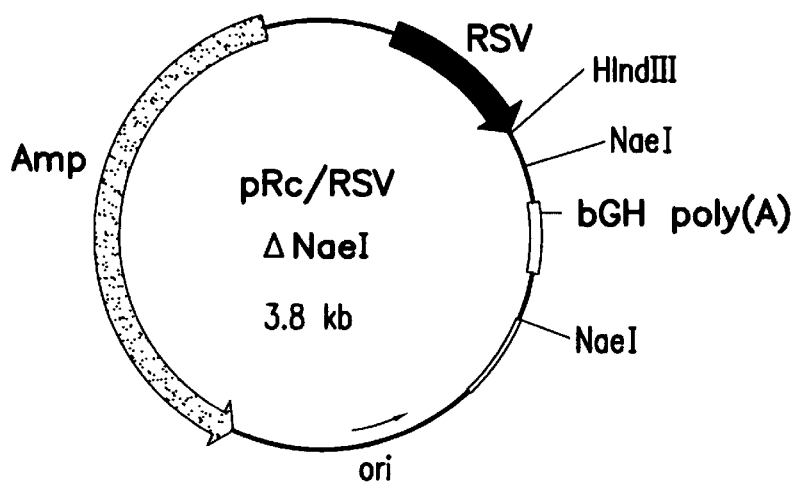
FIG.5

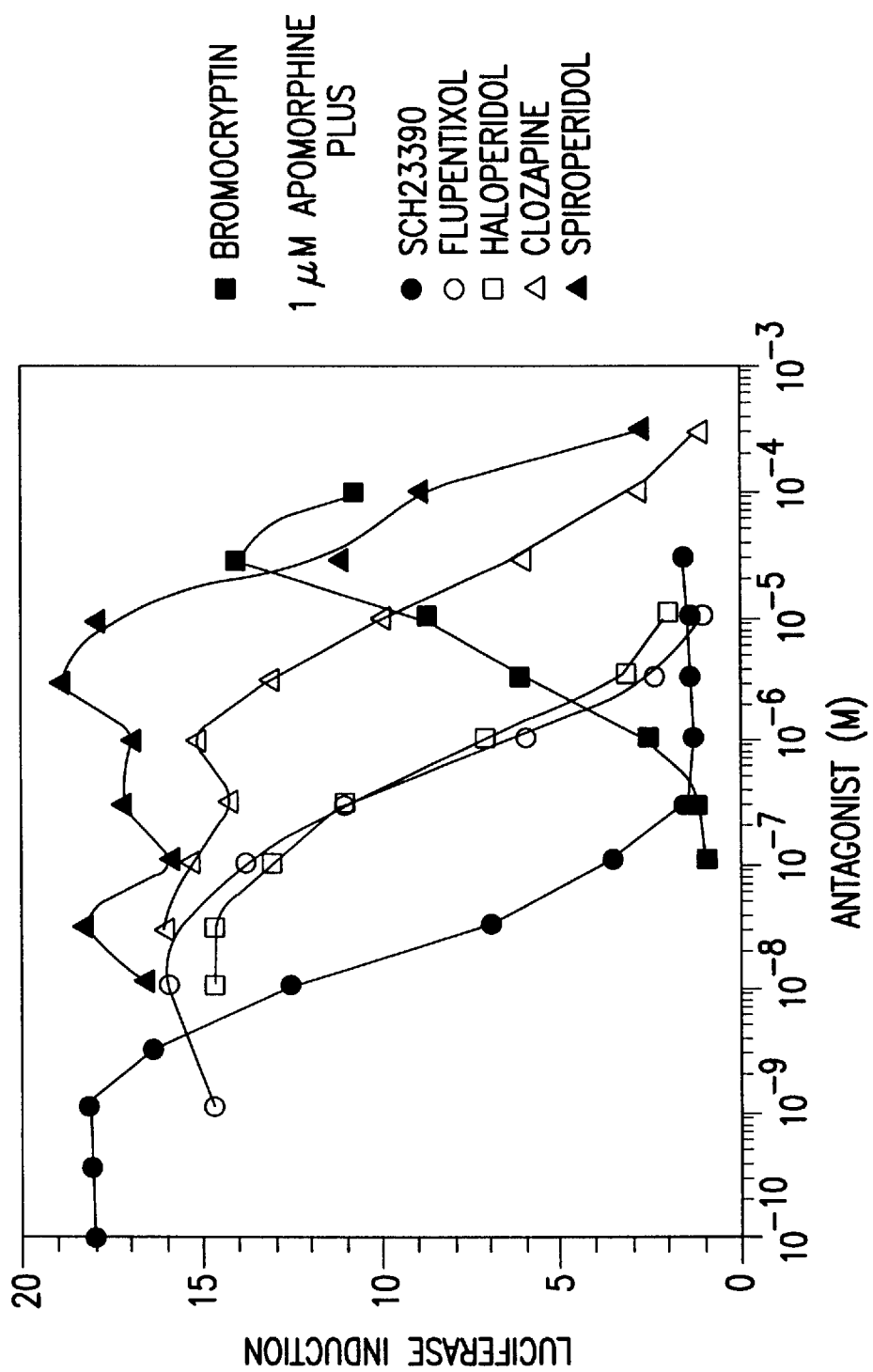

PROCESS FOR SCREENING SUBSTANCES CAPABLE OF MODULATING A RECEPTOR-DEPENDENT CELLULAR SIGNAL TRANSMISSION PATH

FIELD OF THE INVENTION

The present invention relates to a screening method of determining the modulating effect of substances on a receptor-dependent signal transduction pathway in human or animal cells.

BACKGROUND OF THE INVENTION

Conventional tests for discovering pharmacologically active substances are frequently assays in which a substance is investigated to find out to what extent it is able to displace a (labelled) ligand bound to a receptor (radioligand test). Tests of this kind are only able to identify those substances which influence the binding of known ligand receptor binding sites. Thus, these tests only cover the binding of the substance but not a functional response of the cell and therefore cannot distinguish whether the binding substance has an agonistic or antagonistic activity. For radioligand tests, relatively large amounts of receptors are required and frequently receptor-containing membrane fractions are used which are isolated from animal tissue. These tissues may consist of several types of cells containing different or heterologous receptors. In spite of the great significance of such substrates the heterologous composition or—in the case of investigating drugs for their pharmacological effect in humans—the species difference between humans and animals and the resulting difference in the binding properties of ligands to the human receptor and to animal receptors may give rise to problems in interpreting the results.

Many transmembrane signal transduction systems consist of the following membrane-bound components: a) a cell surface receptor; b) a guanine-nucleotide-binding and GTP-cleaving regulatory protein, which is known as a G-protein and which can be coupled both to the receptor and to its effector; c) a so-called "effector", e.g. an ion channel or adenylate cyclases, guanylate cyclases or phospholipases.

The so-called G-protein-coupled receptors pass on the effects of very different extracellular signals such as light, smells, (peptide) hormones, neurotransmitters, etc.; they have been identified in organisms which are evolutionally as far apart as humans and yeasts (Dohlman et al., 1991). Almost all G-protein-coupled receptors have similarities with one another in their sequence; it is assumed that all are based on a similar topological motif common to them all which consists of seven hydrophobic (possibly α-helical) sections which penetrate the lipid double layer.

Cell surface receptors recognise the appropriate liqands from a variety of extracellular stimuli. The bonding of the ligand to the receptor activates a signal cascade which begins with the activation of the heterotrimeric G-protein; the activation of the receptor over a lengthy period results in desensitisation which is caused by various modifications of the receptor. The interaction of the G-protein with the activated receptor causes the replacement of guanosindiphosphate (GDP), bound to the α-subunit, by guanosintriphosphate (GTP), dissociation of the α-GTP-complex from the β-γ-heterodimer and hydrolysis of GTP into GDP. A single receptor can activate numerous G-protein molecules, thereby intensifying the ligand binding phenomenon. The α-subunit to which the GTP is bound and the free β-γ-subunit may interact with the effectors, thereby further intensifying the signal by forming so-called "second messengers". Lower molecular second messengers such as CAMP (cyclic AMP), triggered by activation of adenylate cyclase, cGMP (cyclic GMP), triggered by activation of guanylate cyclase, or inositol-1,4,5-triphosphate ($IP_3$) and diacylglycerols (DAG), triggered by activation of phospholipases, optionally with the participation of hydrolases such as phospholipase C or phospholipase D (Billah et al., 1989), in turn bring about intracellular changes. These include the selective phosphorylation of proteins by activation of protein kinases (e.g. PKC by $IP_3$/DAG, PKA by cAMP), influencing the regulation of the transcription of certain genes, reorganisation of the cytoskeleton and depolarisation of the membrane. (A substance having an antagonistic effect can reverse the interaction caused by a substance with an agonistic effect and the resulting change in concentration of the second messenger, either wholly or partially, or may even result in a reverse functional effect). By means of this signal transduction system, cells are able to communicate with one another and coordinate their development or the effects triggered by them. The non-activated form of the G-protein is reestablished when the GTP bound to the α-subunit of the G-protein is hydrolysed to form GDP.

The specific signal transduction pathways associated with the activation of phospholipases, the reaction product of which is a DAG, or with adenylate cyclase, are hereinafter referred to as "phospholipase signal transduction pathway" (or "phospholipase effector system"), which has as its end product a DAG, or "adenylate cyclase signal transduction pathway" (or "adenylate cyclase effector system").

In mammals, approximately a hundred different G-protein-coupled receptors have been found (some of them bind the same ligands). For example, up till now, five different muscarinic receptor subtypes have been identified, more than eight different adrenergic receptors, at least five different serotonin receptors and four different opsin receptors. A growing group of receptors and receptor subtypes which respond to purines, bombesin, bradykinin, thrombin, histamine, dopamine, ecosinoids, vasopressin, peptide hormones such as GHRH ("growth hormone releasing hormone") and somatostatin have been cloned and characterised (Dohlman et al., 1991, Simon et al., 1991; TIPS Receptor Nomenclature Supplement, 1991; Doods and von Meel, 1991). Different forms, or subtypes, of receptors which respond to the same ligand can be distinguished from one another on the basis of the intracellular reactions which they trigger. These specific receptor subtypes may be coupled with various effector systems and may regulate different ion channels. Since a single receptor subtype (possibly in the same cell or in different cells) may be coupled to more than one effector and several receptor subtypes may activate the same effectors, complicated signal transduction networks are produced. Moreover, characterisation of the G-proteins and the effectors has shown that they are also specified by large families of genes. Numerous G-proteins, various types of adenylate cyclases and phospholipases such as phospholipase C and A2 have been identified. The G-protein-dependent ion channels may also be subdivided into different protein families. At present, it is not clear which criteria determine the specificity of the interaction of the heterogeneous population of G-proteins and effector proteins, how specific receptors are connected to a specific G-protein variant, how they form autonomous circuits, in what way these signal circuits interact with one another and how they are formed afresh during the cell differentiation.

The transcription factors thus activated (e.g. CREB protein, AP1 protein) interact with the regulatory DNA elements CRE (CRE-element, "cAMP responsive element") or TRE (TRE="TPA responsive element": TPA=phorbol-12-myristat-13-acetate =phorbolester), which bind CREB and AP1: many genes the transcription of which is regulated by cAMP (e.g. rat somatostatin, human-α-gonadotropin) contain in the 5'-flanking region a conserved sequence as the regulatory element. This sequence is identical or similar to the palindromic octamer TGACGTCA (Montminy et al., 1990). TRE-elements contain the very similar heptameric motif TGAGTCA, which differs from the CRE-element consensus sequence only in a single nucleotide (Deutsch et al., 1988). The TRE-motif, or very similar motifs, have been identified in numerous genes the transcription of which is activated by phorbolester (Angel et al., 1987a and b; Lee et al., 1987). Surrounding DNA sequences or protein-protein interactions with other factors determine, inter alia, the concrete regulatory phenomena at a specific gene.

Because of the complexity of the network of the signal transduction pathways there may be so-called "crosstalk" between signal transduction pathways, e.g. the adylate cyclase and the phospholipase C-signal transduction pathway. The term "crosstalk" refers to the phenomenon that the influencing of one effector-system also causes influencing of the other (Sassone-Corsi et al., 1990; Houslay, 1991). The phenomenon of crosstalk is used physiologically for integrating or cross-linking signals in order to produce a redundancy of signals or to ensure communication of the various signal transduction pathways. Crosstalk may occur at various planes of the signal transduction pathway, inter alia at the plane of the G-proteins. For example, a receptor or receptor subtype may interact with more than one G-protein variant, so that both the cAMP- and also the $IP_3$/DAG-level may possibly be affected. A possible cause of pathological changes in the cells is the disruption of these interactions, e.g. if a specific receptor does not interact correctly, in the physiological sense, with an effector system.

There is a need for assays which make it possible to discover drugs for the treatment of pathological conditions which are specific for a certain receptor or receptor subtype and which, furthermore, specifically influence only one particular receptor-dependent signal transduction pathway.

Assays have already been developed which make use of the effect that the modulating activity of substances on the receptor-dependent signal transduction pathway can be detected by means of the expression of genes:

An assay system described by King et al., 1990, is based on the influencing of the signal transduction pathway which is used by the G-protein-coupled pheromone receptors of *Saccharomyces cerevisiae*, in which the reaction to the bonding of an agonistically effective compound to a receptor transfected into the yeast cell is measured in the yeast cell by colorimetry. For this purpose a modified β-adrenoreceptor gene was co-transfected under the control of the galactose-inducible GAL1-promotor (in order to achieve high expression rates), with the mammalian G-protein-subunit $G_s\alpha$ in a yeast strain which contains a reporter gene (β-galactosidase) stably integrated in the genome under the control of a FUS1-promotor which responds to pheromone. This system offers an opportunity of screening substances the agonistic effect of which activates β-galactosidase, this activation being measurable in a simple, automated assay based on a colour change. However, this system has the disadvantage that the use of a human protein isolated from its complex system in a yeast cell cannot lead to any direct conclusions as to the processes in the human cell. Moreover, this system in yeast cells requires the co-transfection of a suitable G-protein subunit capable of interacting with the human receptor. This system does not use the signal transduction system inherent in higher cells and functional analysis of receptor-active substances in this system therefore presents problems.

Montmayeur and Borelli, 1991, described an assay which is based on the influencing of the adenylate cyclase signal transduction pathway by activation of G-protein-coupled receptors ($D_2$-receptors and the β-adrenergic receptor were used). The receptors were used to transform human cells which contain as reporter gene the chloramphenicol-acetyltransferase gene (CAT) under the control of a thymidine-kinase (TK) promotor. Preceding the promotor is a synthetic oligodesoxynucleotide sequence which contains a promotor element responding to cAMP ("cAMP responsive element" CRE). By means of the CAT-activity it was possible to demonstrate that agonistically activated compounds for the β-adrenergic receptor, which is known to activate adenylate cyclase, brought about a dosage-dependent increase in CAT-activity. After co-transfection with the dopamine receptors which inhibit adenylate cyclase, this activity fell back again. This showed that the cAMP-induced expression of the reporter gene can be modulated positively and negatively in dosage-dependent manner.

This assay is restricted to measuring the expression of genes which is regulated by the cAMP-concentration; it does not allow measurement of the $IP_3$/DAG-regulated gene expression. Interactions between the adenylate cyclase and the phospholipase C-signal transduction pathway caused by crosstalk cannot be detected with this assay either, or can only be partially detected.

BRIEF DESCRIPTION OF THE FIGURES

FIG. 2 depicts the nucleotide sequence of the BglII—BamHI fragment after PCR for the construction of plasmid pADneoTK.

FIG. 5 depicts the construction of the plasmid pRc/RSVΔNaeI.

FIGS. 37A, 37B, 38A and 38B depict dosage activity curves of luciferase activity as a function of the activation of the dopamine-D1-receptor.

DESCRIPTION OF THE PREFERRED EMBODIMENTS

Figure 1:
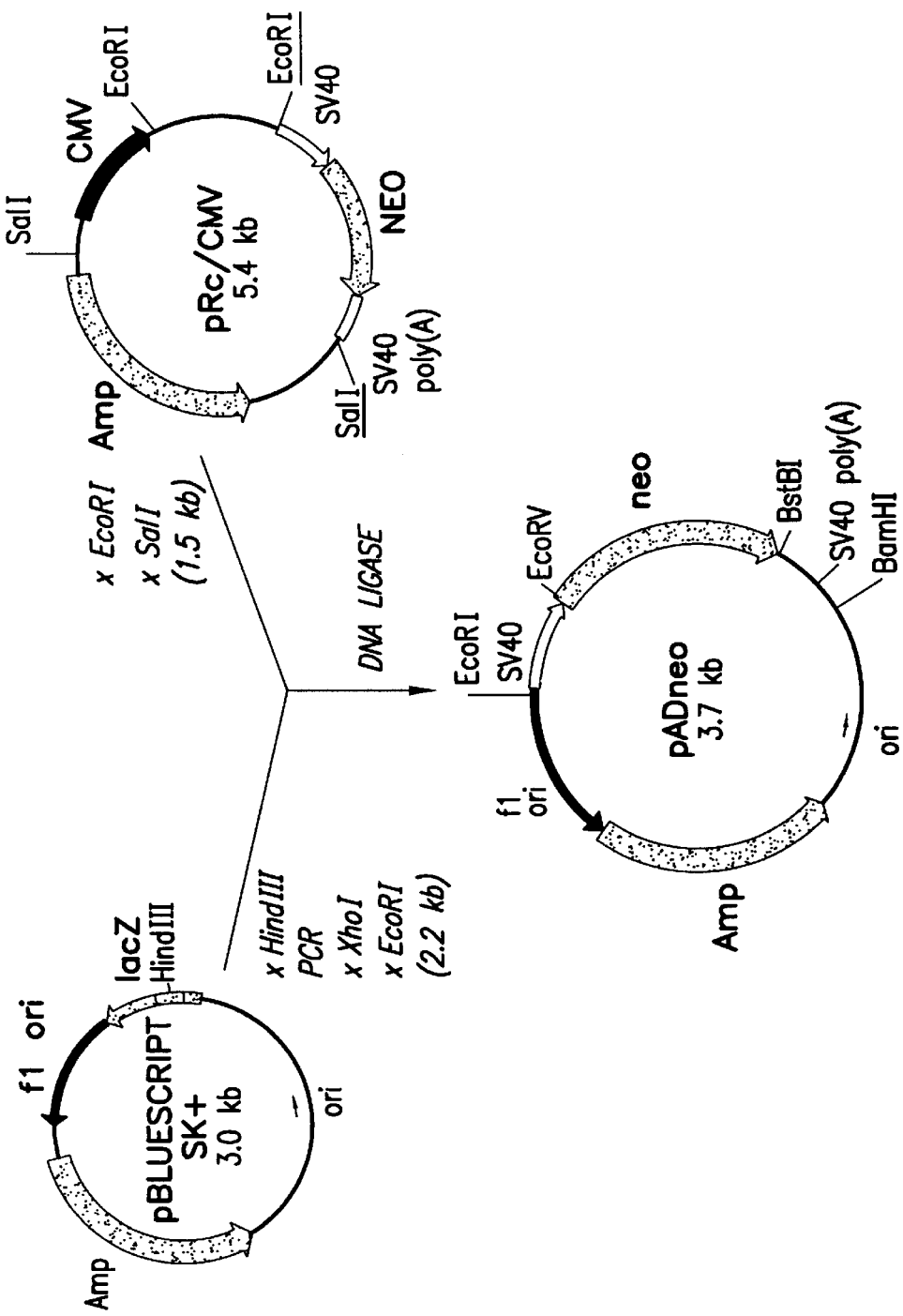
FIG. 1 depicts the construction of the plasmid pADneo.

The aim of the present invention was to provide a process suitable for screening substances which, depending on the receptor, modulate a phospholipase signal transduction pathway, particularly the phospholipase C-signal transduction pathway. These include substances which bind to the ligand binding site of the receptor, substances having an allosteric activity as well as substances which act non-competitively with respect to the ligand binding site. In particular, the present invention sets out to provide a process which can be automated and is thus suitable for screening substances at high throughputs and which also makes it possible to investigate complex mixtures of substances, such as extracts from organisms, for their content of pharmacologically active substances.

The present invention thus relates to a process for determining the modulating effect of a substance on a receptor-dependent signal transduction pathway in the human or animal cell. The process is characterised in that the modulating effect on the substance on the activity of a phospholipase which yields a diacylglycerol, optionally with the participation of hydrolysis, and particularly on the phospholipase C-activity or on a mechanism which precedes or follows the phospholipase C-activation in the signal transduction pathway, preferably its modulation of the signal transduction pathway triggered by G-protein-coupled receptors, is determined by incubating mammalian cells which a) are transformed with a recombinant DNA, containing a reporter gene and a regulatory sequence which responds to the change in concentration of inositol-1, 4,5-triphosphate ($IP_3$) and diacylglycerol (DAG) caused by the modulation of the phospholipids, particularly phospholipase C, so that the expression of the reporter gene is modulated by a change in concentration of $IP_3$/DAG, and which are furthermore b) transformed with a recombinant DNA containing a sequence coding for a receptor which is coupled to the phospholipase-effector system in such a way that the cells express the receptor, with the substance which is to be investigated and measuring the concentration of the reporter gene product.

The recombinant DNA which responds to changes in the $IP_3$/DAG concentration—or in the case of control cells, the use of which will be described hereinafter, to changes in the cAMP-concentration—is also a subject of the present invention. It is hereinafter referred to as "sensor-DNA". A reporter gene is defined by the fact that its expression product is detectable and quantifiable by measuring a signal proportional to its concentration.

Regulatory sequences contained in the sensor DNA and responding to the change in concentration of $IP_3$/DAG contain one or more heptameric TRE-motifs, hereinafter referred to as "TRE-elements".

Regulatory elements contained in the sensor DNA which respond to the change in concentration of cAMP contain one or more octameric CRE-motifs, hereinafter referred to as CRE-elements.

Alternatively, the sensor DNA may contain a sequence coding for a protein which is only activated directly post-transcriptionally by increasing the calcium concentration.

The recombinant DNA which contains a sequence coding for a receptor is hereinafter referred to as "receptor DNA".

According to another aspect the present invention relates to cells which are transformed only with sensor DNA. These cells are hereinafter referred to as "pretest cells".

Cells which are transformed with sensor DNA and receptor DNA are hereinafter referred to as test cells; these cells are also the subject of the present invention.

If substances are to be investigated with respect to their pharmacological effect for the treatment of pathological conditions in man, the receptor DNA preferably contains a sequence coding for a human receptor. (The process according to the invention is preferably used for discovering substances which are suitable for treating pathological conditions in man. It may, however, also be used for screening substances used for the treatment of animals; in this case, the corresponding animal receptors are used.)

The term "substance" for the purposes of the present invention includes both pure substances and mixtures of substances.

By "modulating" effect is meant an agonistic or antagonistic effect on a receptor-dependent signal transduction pathway.

In a preferred embodiment of the present invention the cells are transformed with a DNA coding for a G-protein-coupled receptor.

According to a preferred embodiment of the process according to the invention, in addition, control cells which are transformed only with recombinant DNA according to step a) (TRE-pretest cells) are treated with the test substance to find out whether the expression of the reporter gene can be ascribed to a receptor-dependent modulation. If the expression of the reporter gene is due to a receptor-independent modulation of the phospholipase C-effector system or, if endogenous receptors are present, a modulation of the phospholipase C-effector system dependent on these receptors, this modulation is detected by the TRE-pretest cells.

In order to investigate the specificity of the test substance on the phospholipase C-signal transduction pathway, parallel tests are conveniently carried out with pretest cells the sensor DNA of which contains a regulatory sequence which responds to the change in the cAMP-concentration caused by the modulation of adenylate cyclase (CRE-pretest cells).

If desired, CRE-test cells which are transformed with the same receptor as the TRE-test cells are additionally used as control.

CRE-test cells may be used not only as control cells but also as primary substrate cells in a screening in which substances are investigated for their receptor-dependent modulating effect on the adenylate cyclase signal transduction pathway. In this case the CRE-test cells are transformed with receptor DNA which contains the sequence coding for a receptor coupled to the adenylate cyclase effector system. CRE-pretest cells are used in such a screening as control cells. If desired, TRE-pretest cells and optionally TRE-test cells as well, transformed with the identical receptor coupled to the adenylate cyclase effector system, may be used as a further control.

Cells which do not endogenously express the receptor in question are preferred for the production of (pre)test cells, as the endogenous expression of the receptor itself, on the basis of the change in expression of the reporter gene, emits a signal which interferes with the results of the measurement. The use of cells which endogenously express the receptor is not excluded, however, provided that it is made certain that these cells strongly over-express the exogenous receptor, so that the endogenous expression by comparison thereto is negligibly small and the measuring results are not affected. In order to discover whether a cell is fundamentally suitable as a (pre)test cell for the process according to the invention, e.g. that it does not express or only slightly expresses the special receptor for which the modulating influence on the phospholipase C-effector system by the test substance is to be determined, the procedure used may be, for example, to transform a mammalian cell with TRE-sensor-DNA and subsequently treated with a substance which is known to activate the receptor in question. If the cell does not respond to this treatment or responds only to a limited extent, it can be regarded as fundamentally suitable for use as a test cell. (For testing cells for their suitability as CRE-test cells, the cells are tested analogously, with the difference that CRE-sensor DNA is used.) Another possible way of discovering whether the cell expresses the receptor is to measure the expression directly by molecular biological methods, e.g. by PCR (polymerase chain reaction) or Northern blots.

Preferably, the starting cells for the production of (pre)test cells are selected because they endogenously express none or as few as possible of the receptor types in question in order to transform them with as many different types of receptor as possible and therefore make them suitable for the production of as many test cells as possible.

It is preferable to use cells which exhibit strong expression of the TRE-regulated reporter gene after stimulation with substances which increase the $IP_3$/DAG-concentration, or pretest cells which exhibit strong expression of the CRE-regulated reporter gene after stimulation with substances which increase the cAMP-level. In order to obtain test cells in which the receptors in question efficiently couple to the phospholipase C-signal transduction pathway after the action of a drug, mammalian cells are investigated for their suitability as test cells by first transforming them with sensor DNA (pretest cells) which contain one or more TRE-elements or contain a sequence coding for a protein which is activated by calcium. The pretest cell transformed with sensor DNA is then treated on the one hand with substances which bring about or simulate an increase in the cAMP-concentration (e.g. with forskolin), and on the other hand with substances which bring about or simulate an increase in the $IP_3$/DAG-concentration (e.g. with TPA). If the cell emits a signal only when treated with TPA but not when treated with forskolin, it satisfies the primary requisite of responding specifically to changes in the $IP_3$/DAG concentration, i.e. there is no crosstalk at the expression in this cell (a corresponding procedure is used for CRE-test cells; the CRE-pretest cell responds to forskolin). Furthermore, the pretest cell is expediently investigated to find out whether a coupling will occur which is physiologically "correct" for the receptor to be introduced and whether the signal transduction pathway will thus be initiated; the prerequisite for this, inter alia, is that the cell contains the G-protein variant specific to the receptor (or a G-protein variant which can functionally replace the receptor-specific one). For an investigation of this kind, for example, the pretest cell is transformed with the receptor in question, treated with known ligands and tested to see whether modulation of the reporter gene expression takes place.

A further requisite for the suitability of a cell for use within the scope of the present invention is the stability of the cell, both in terms of its usefulness as a pretest cell (transformed only with sensor DNA) and also as a test cell (transformed with sensor and receptor DNA). In order to test the stability of the cells (viability, stable integration of the foreign DNA into the genome), experiments are carried out over a lengthy period of time under identical conditions with the pretest cells (treatment with substances which influence the concentration of second messenger) and the test cells (treatment with receptor ligands) and the reproducibility of the results is investigated.

Examples of suitable cells are those of the cell lines CHO ("Chinese hamster ovary" cell line), COS (monkey kidney cell line), A549 (human lung cancer cell line) and JEG-3 (human choriocarcinoma cell line).

The pretest cells according to the invention are used on the one hand as a starting substrate for the preparation of test cells which contain receptor DNA and on the other hand they are used in the process according to the invention as control cells for checking whether or not a signal can be put down to a receptor-dependent modulation of the signal transduction pathway by the test substance. If the substance generates a signal in the test cell and does not generate a signal in the pretest cell used as a control, the modulation of the expression of the reporter gene detected by the signal is exclusively receptor-dependent. Even though the control cell emits a signal, the substance (also) influences a process in the signal transduction pathway which is receptor-independent; the control measurement corresponding to this signal must be subtracted from that obtained in the test cell.

The sensor DNA is preferably located on a plasmid which can be replicated in a high copy number in a suitable host organism, preferably E. coli, and after transfection into mammalian cells and integration into the host genome, permits expression of a reporter gene under the control of regulatory elements. It is preferably a shuttle vector which contains an expression cassette for the reporter gene (sensor DNA) and a selectable marker for mammalian cells as well as at least one replication origin and a marker for the replication and selection in E. coli.

In order to produce permanent cell lines which contain the sensor DNA stably integrated in their genome, the vector contains a dominant selection marker. The use of a particular selection marker is not critical; for example, it is possible to use the gene for neomycinphosphotransferase (neo), which imparts resistance to the antibiotic geneticin (G-418) (Southern and Berg, 1982), the DHFR-gene (dihydrofolate reductase) for DHFR-deficient cells, the gene for xanthine-guanine-phosphoribosyl transferase (gpt), which imparts resistance to mycophenolic acid (Mulligan and Berg, 1981) or the hygromycin-B-phosphotransferase gene (hph; Gritz and Davies, 1983). Examples of promoters which operate the selection marker gene are the SV40 Early Promotor, the cytomegalovirus promotor (CMV-promotor), the promotor of the thymidine-kinase gene of the Herpes simplex virus (TK-promotor), the Rous Sarcoma virus (RSV) long terminal repeat (LTR). The plasmids are preferably constructed so that individual important elements such as the reporter gene, the promotor for the reporter gene and the regulatory sequences for the selection marker can simply be exchanged or altered, in order to be able to correspond to any different requirements resulting from the particular application, e.g. as the result of the use of a different cell line. Such measures consist, for example, in incorporating multicloning sites in front of the promotor or promoters or in front of the reporter gene in order to permit the cloning of regulatory sequences which modulate the promotor or of different reporter genes.

The guiding premise for selecting a suitable reporter gene was to provide a preferably non-radioactive, automatable assay with a high degree of sensitivity.

Within the scope of the present invention it is theoretically possible to use all the reporter genes which satisfy these conditions:

Alkaline phosphatase can be measured with high sensitivity when using a chemiluminescent substrate but it does have the disadvantage that many mammalian cells express this enzyme relatively strongly. It can therefore generally be used as a reporter gene only for those cell lines which do not express it or express it only slightly.

The expression product of the β-galactosidase and β-glucuronidase gene are able to cleave the corresponding methylumbeliferyl-galactoside or -glucuronide to form fluorescent groups. These enzyme reactions are monitored using established fluorescence assays (Wieland et al., 1985; Kricka, 1988).

The expression of chloramphenicol-acetyltransferase (CAT) can admittedly be detected with relatively high sensitivity but the assay has, inter alia, the disadvantage that it is radioactive and is difficult to automate (Hartmann, 1991).

Preferably, within the scope of the present invention, the gene coding for Photinus pyralis luciferase (De Wet et al., 1987) is used as the reporter gene. This enzyme has the advantages that it produces a high yield of bioluminescence with its substrate luciferin, with the addition of ATP, and the bioluminescence can be measured using established, automatable methods, and this enzyme is not endogenously produced by mammalian cells. Furthermore, luciferase has a relatively short half life in vivo and is not toxic even in high concentrations (Hartmann, 1991; Brasier et al., 1989).

Measurement of the activity of the firefly luciferase by means of bioluminescence is one of the most sensitive methods of measuring an enzyme. Therefore, and in view of the absence of luciferase activity in normal mammalian cells, this enzyme is particularly suitable as a reporter gene in studies of gene regulation (Subramani and DeLuca, 1987).

One disadvantage of measuring luciferase activity is the poor stability of the light signal under reaction conditions which are ideal for achieving the maximum light yield (DeLuca et al., 1979). This means that the luciferase activity is best measured in measuring equipment in which the light produced is measured directly after the addition of the substrate solution with the components required for the luminescence reaction. Another problem in determining the luciferase activity in reporter gene studies is the lysing of the cells in order to release the enzyme, which makes a further step necessary (Brasier et al., 1989).

According to another aspect the present invention thus relates to a reagent for measuring the activity of a luciferase expressed in cell cultures.

The reagent according to the invention makes it possible to measure the luciferase activity expressed in cell cultures directly in a single step. This reagent on the one hand lyses the cells by means of a detergent and on the other hand contains the substrates necessary for the luciferase reaction. By means of this reagent, with its content of selected substances, a particularly constant light signal is obtained enabling the luciferase activity to be measured in a period of between 2 and 20 minutes after the addition of the reagent. Furthermore, this reagent is stable for at least one week in its read-to-use state. The reagent consists of a basic buffer which contains suitable buffer substances such as tricin, HEPES, glycylglycine, phosphate, tris, preferably tricin (Leach and Webster, 1986). The pH of this buffer is in the range between 6 and 9, preferably between 7 and 8. Furthermore, a magnesium salt, preferably magnesium sulphate-heptahydrate ($MgSO_4.7H_2O$) is added to the buffer in a concentration of between 10 and 0.1 g/l, preferably 4g/l. The substrates required for the luciferase reaction are preferably present in the following concentrations: adenosine triphosphate (ATP) from 0.05 to 5 g/l, preferably 0.7 g/l; luciferin from 0.001 to 0.1 g/l, preferably 0.015 g/l. The buffer may additionally contain a complex-forming agent such as ethylene dinitrilotetraacetic acid disodium salt (EDTA) in a quantity of about 0.2 g/l.

The preferred basic buffer (plus substrates for the luciferase reaction) is made up of 25 mmol/l tricin, 0.5 mmol/l EDTA, 16.3 mmol/l $MgSO_4.7H_2O$, 1.2 mmol/l ATP and 0.05 mmol/l luciferin Na salt.

In order to stabilise the luciferase, a mild organic reducing agent such as dithiothreitol (DTT) or β-mercaptoethanol is used, on its own or in admixture with other reducing agents. A reducing agent of this kind prevents the oxidation of SH-groups present in the enzyme and consequent deactivation of the luciferase during the luminescence reaction. DTT is used in a concentration of between 0.1 and 50 g/l, preferably 1 g/l. BME is added in a concentration of between 0.1 and 50 ml/l, preferably 4 ml/l.

In order to stabilise and intensify the luminescence, sodium tripolyphosphate (NaTPP) may additionally be used, and is added in a concentration of between 0.005 and 5 g/l, preferably 0.2 g/l. Instead of sodium tripolyphosphate it is also possible to use sodium pyrophosphate.

The cells are lysed using a suitable detergent such as Triton X-100, Tween 20 or 80, NP 40, Brij or the like. Triton X-100 is used in a concentration of between 0.01 and 5%, preferably 0.1%.

Alternatively, the gene coding for the enzyme apoaequorin from the source Aequoria victoria (Tanahashi et al., 1990) may be used as the reporter gene. This enzyme has the advantage that, with its cofactor coelenterazin, after binding calcium ions, it produces high yields of bioluminescence which can be measured by established automated methods. A further advantage is that this enzyme is not endogenously expressed by mammalian cells.

When constructing the sensor-DNA the reporter gene is put under the control of constituent, preferably weak promotor elements which can be modulated by one or more preceding TRE- or CRE-regulating elements. The most suitable sensor DNA construction is determined by transiently transforming the cell with different sensor DNA plasmid constructs, varying on the one hand the reporter gene and on the other hand the control sequences, and investigating the measurement of the reporter gene product for its sensitivity. The person skilled in the art is familiar with the control sequences suitable for expression in particular mammalian cells; the choice may be made initially from the relevant literature (e.g. Landschulz et al., 1988, Turner and Tjian, 1989), and the choice may be narrowed down or perfected by means of the above-mentioned transient transfection experiments which are easy to carry out. Examples of suitable promoters are the β-globin promotor and the TK-promotor. If desired, known natural or synthetic promoters are modified, e.g. by shortening them to the minimum sequence required for the promotor function. If desired, the regulation sequence of a gene which can be induced by cAMP or $IP_3$/DAG may be used, this gene containing a promotor and regulatory element (Montminy et al., 1990, Deutsch et al. 1988), e.g. the 5'-regulatory sequence of the ICAM-1 gene. If the apoaequorin gene is used as reporter gene, the gene is expediently placed under the control of a strong structural promoter.

The choice of the regulatory sequence (CRE- or TRE-element including its flanking sequences) contained in the sensor DNA is generally made empirically, starting from elements known from the literature (see for example Montminy et al., 1990, Deutsch et al., 1988) which are investigated in preliminary trials for their suitability in providing a sensitively detectable inducibility of the reporter gene in a given cell system. Examples of suitable regulatory elements including the flanking sequences thereof are the sequences of somatostatin "vasoactive intestinal peptide", cytomegalovirus enhancer, bovine leukaemia virus long terminal repeat (BLV LTR) (CRE-elements) and ICAM-1, collagenase, parathyroid hormone (TRE-elements). If the TRE- or CRE-motifs contained in the natural sequences do not have a perfect consensus sequence they, and optionally the sequences adjacent to them, may be altered by exchanging one or more nucleotides.

The regulatory elements (TRE- or CRE-elements) and the sequences flanking them may be produced synthetically or may be of natural origin. If a natural sequence is to be used which is known to respond to cAMP and/or $IP_3$/DAG depending on the type of cell (Karin; 1989), it is investigated in the pretest cell as to which second messenger it responds to, by treating the cells for example with TPA and forskolin.

The sensor DNA may possibly contain one or more CRE-elements in addition to one or more TRE-elements. With a sensor DNA of this kind both the activation of one or other signal transduction pathway on its own or the parallel activation of both signal transduction pathways will be detected.

In order to intensify the modulating effect of $IP_3$/DAG and/or cAMP on the reporter gene expression, a construct may optionally be used containing numerous regulatory CRE- and/or TRE-sequences in tandem. Preferably the regulatory sequence contains three to twelve TRE- and/or CRE-elements. When arranging the individual elements of the construct the space of the TRE- and/or CRE-elements relative to one another is selected so as to ensure that the transcription factor binds to the CRE- or TRE-elements. The optimum spacing of the regulatory TRE- or CRE-elements to one another, which is also determined in the light of the steric arrangement, is determined empirically in preliminary tests, as may also be the spacing from other regulatory DNA elements which affect the transcription, e.g. from the TATA-box. The TRE- or CRE-elements and/or the flanking sequences may be identical or at least partially different, the latter embodiment being preferred for the tandem construction.

As sequences flanking the CRE- or TRE-element which have been found also to affect the regulating qualities of the CRE- or TRE-elements, it is preferable to use, particularly in the immediate vicinity thereof, those sequences which naturally surround the special regulatory element (Montminy et al., 1990, Deutsch et al., 1988). The sequence or arrangement thereof is determined empirically.

The elements of the sensor DNA and the marker gene used for the selection may possibly be found on two separate plasmids, one of which contains the reporter gene construct (including the expression control sequence which contains the regulatory sequence) whilst the other contains the selection marker gene construct.

Examples of suitable selection marker gene constructs are the plasmids pRSVneo, pSV2neo, pRSVgpt, pSV2gpt, the construction of which can be found in the relevant manuals, e.g. "Cloning vectors".) If separate plasmids are used the cells are co-transfected with the two plasmids and selected on the marker. The presence of the selection marker leads one to conclude that the cell also contains the reporter gene construct, since it is known that co-transformation of two genes which are located on DNA segments not physically connected to one another frequently leads to the expression of both co-transformed genes (Winnacker, 1985).

With respect to the measuring system to be used in the test proceedings it is advisable to perfect the ratio between the maximum change and the normal value of the measuring signal, preferably by varying the construction of the sensor DNA, e.g. by structural change to the promotor arrangement. The background signal is preferably low enough to detect induction of the reporter gene expression with a high degree of sensitivity, but at the same time high enough to make it possible to determine the detection limits with respect to the negative control.

For the reception DNA construct, basically the same considerations apply as to the sensor DNA construct, except that the receptor sequence is preferably put under the control of a strong, constituent promotor. If desired, the sequence coding for the receptor and the dominant selection marker may also be on two separate plasmids, with which the cells are co-transformed, in the case of the receptor DNA as well.

The transfection of the cells with sensor or receptor DNA is carried out by conventional methods of transfection (cf. for example Potter et al. 1984; Felgner et al., 1987), the preferred methods being electroporation, calcium phosphate precipitation and lipofection.

Generally, the cells are first transformed with sensor DNA in order to obtain pretest cells and then the pretest cell is transformed with receptor DNA to produce the test cell.

The construction of the sensor DNA is preferably perfected to achieve maximum inducibility by means of a single specific effector system of the pretest or test cell, the aim being to achieve minimum inducibility by other effector systems. The TRE-test cell thus preferably responds specifically to substances which modulate the phospholipase C-signal transduction pathway in receptor-dependent manner.

In order to rule out receptor-independent influence by the test substance, as already explained, the corresponding TRE-pretest cell is treated in parallel with the substance. In order to make it possible to pronounce on the specificity of the substance on the phospholipase C-effector system a measurement is optionally carried out, as a negative control, in which the pretest cell is transformed with CRE-sensor DNA and the test cell derived therefrom is additionally transformed with the identical receptor being investigated.)

In order to monitor the specificity of the influence on the phospholipase C-signal transduction pathway with regard to the receptor (or receptor subtype) being investigated by the substance discovered, it is convenient to carry out further control tests in which TRE-pretest cells are transformed with other different receptors and treated with the substance. If a substance is only allowed to influence one receptor specifically, which is generally the case with regard to the specificity of a drug, the substance may only modulate this one receptor.

Suitable receptors for the transfection of TRE-pretest cells in order to obtain TRE-test cells are all those receptors which are capable of coupling with the phospholipase C-signal transduction pathway. These include: α-adrenoceptor(adrenalin)-receptors of the $α_1$-type, angiotensin II receptors, atrionatriuretic peptide receptor, bombesin receptors, bradykinin receptors, cholecystokinin and gastrin receptors, endothelin receptors, metabotrophic excitatory amino acid receptors, histamin receptor ($H_1$), serotonin receptors (5-$HT_{1C}$, 5-$HT_2$), leukotriene receptors ($LTB_4$, $LTD_4$), muscarinic acetylcholine receptors ($M_1$, $M_3$, $M_5$), neuropeptide Y-receptors (also PYY, NPP), neurotensin receptor, PAF (platelet activating factor) receptor, prostanoid receptors ($EP_{1-3}$, FP, TP), $P_2$-purioceptor ($P_2$gamma), tachykinin receptors ($NK_{1,2,3}$), vasopressin and oxytocin receptors ($V_{1A}$, $V_{1B}$, OT), thrombin receptor, etc. Many of these receptors may also couple to other effectors such as adenylate cyclase. The receptors mentioned and other suitable receptors as well as the effector system to which the receptors are coupled can be found in the specialist literature; a summary can be found in the TiPS Receptor Nomenclature Supplement, 1991.

Examples of non-G-protein-coupled receptors which activate phospholipase C and can therefore be used within the scope of the present invention for the transfection of the substrate cells are members of the families of the FGF-receptors, insulin receptors, PDGF-receptors, EGF-receptors, etc. (Ullrich and Schlessinger, 1990).

Receptors which are capable of coupling to the adenylate cyclase effector system and which can be used to transfect CRE-pretest cells in order to obtain CRE-test cells can also be found in the TiPS Receptor Nomenclature Supplement, 1991. Examples include the receptors for adenosine (A1, A2), for adrenalin (β- and $α_2$-type), for dopamine (D1, D21 (=$D_{2A}$), $D_{2s}$(=$D_{2B}$), for histidine ($H_2$-type), for serotonin (5-$HT_{1A}$- and 5-$HT_{1D}$-type, 5-$HT_4$), for acetylcholine ($M_2$- or $M_4$-type) and for encephalines.

(If a receptor is to be used which has not yet been cloned or of which the cDNA is not available in corresponding vectors, the receptor DNA may be obtained, e.g. by screening of CDNA or genomic banks, and cloned.)

If a receptor is negatively coupled to adenylate cyclase (e.g. acetylcholine receptors of $M_2$- or $M_4$-type, neuropeptide Y-receptor), i.e. activation of the receptor brings about a lowering of the cAMP-concentration, the reduction in the cAMP-concentration is appropriately measured as follows: the cells are treated with the test substance; if it is an agonistically acting substance the receptor is activated, resulting in a lowering of the cAMP-level. At the same time or possibly thereafter the cell is treated with a substance which is known to increase the cAMP-concentration. It is also possible, conversely, first to increase the cAMP-concentration and then carry out the incubation with the substances being investigated. (The increase in the cAMP-level may be carried out directly, e.g. with forskolin, or indirectly by treating the cells with a substance which has an agonistic effect on a receptor which is positively coupled to adenylate cyclase. This receptor is either an endogenous receptor or a receptor with which the cell has been co-transformed.) As a control, a parallel test is set up with identical incubation conditions in which only the increase in the cAMP-concentration is determined. The difference in the signal values corresponds to the lowering of the cAMP-concentration, which can be attributed to the activity of the substance; it is a measurement of the receptor-dependent lowering of the adenylate cyclase activity. The indirect measurement of the receptor activation with negative adenylate cyclase coupling is necessary if the cAMP-concentration naturally present in the cell is very low and therefore any reduction in this concentration cannot be detected by measuring instruments.

Receptors whose activation modulates the adenylate cyclase effector system, in addition to the phospholipase C-signal tranduction pathway, by means of crosstalk, inter alia, can also be used within the scope of the invention. If the sensor-DNA responds only to the change in concentration of $PI_3$/DAG (TRE-sensor-DNA), a signal will only be generated when a transcription factor is activated which binds to the TRE-element. It is irrelevant whether the adenylate cyclase effector system is also activated in parallel and the signal or part thereof is generated by crosstalk.

After transformation of the cells with receptor DNA the positive clones are investigated for expression of the receptor, e.g. using binding assays in which known radioactively labelled agonists and antagonists are used.

The number of receptors in molecules per cell can be determined by means of Scatchard blots (Human Pharmacology, 1991).

Preferably, a clone having a receptor number which corresponds as closely as possible to the physiological receptor concentration is selected from the stable transformands which contain receptor DNA. (If the receptor number is too high, incomplete and possibly non-specific coupling may take place or, in addition to the specific coupling, non-specific coupling may occur, possibly activating other effector systems at the same time. If the receptor number is too low, the signal may possibly be too low to be picked up by the measurement.)

A receptor or receptor subtype can be transfected into two different pretest cells, one of which responds to the IP3/DAG-concentration whilst the other responds to the cAMP-concentration. (The cell used in parallel is investigated with the sensor DNA specific to the other effector system, e.g. the adenylate cyclase effector system, to discover whether it is activated specifically by means of the cAMP-signal transduction pathway, by treating it separately with substances which increase the cAMP or IP3/DAG concentration or simulate such an increase in concentration, e.g. with forskolin and TPA. For these preliminary tests the cells may either be transformed only with sensor-DNA, in which case stable transformation is not necessary, or else co-transformed with the receptor DNA; in the latter case the medium should not contain any substances which activate the receptor. Once it has been established that the cells respond only to forskolin, the assay carried out with TRE/receptor-transformed cells is repeated under the same conditions with CRE-test cells.) By comparing the data obtained with a specific substance and a specific receptor (subtype) in the specific TRE-cells and in the specific CRE-cells and in a test cell which responds to IP3/DAG and to cAMP, it is possible to establish to what extent the signal can be attributed to crosstalk and how much it can be put down to the influencing of only one of the two effector systems.

The substances to be investigated for their potential pharmacological activity by means of the process according to the invention are natural or synthetic substances and it is possible to use both pure substances and mixtures of substances (e.g. vegetable extracts, fermentation liquors, etc.). The pure substances may be, in particular, low molecular synthetic organic compounds. The substances are conveniently applied to the cells in serial dilutions in order to detect the largest possible range of concentration. The incubation time is determined empirically, e.g. by treating the given test cells with known receptor agonists and determining the moment from which the induction of the reporter gene expression can be measured reproducibly. The incubation time is generally finished at this moment and generally comes to at least one hour. The absolute number of test cells is not critical. The number of cells will depend particularly on the detection limits of the measuring signal and on the stage of growth the cells are at, the lower limit being defined by the technological possibility of uniformly distributing the cells over the test units. If microtitre plates with 96 wells are used, the number of cells will be, for example, about 20,000 to about 200,000 cells per test unit, but it may be lower if the measuring signal is sensitive enough and the cells are accurately distributed. The growth stage at which the cells are put in depends on the cell-type-specific properties of the starting cell; furthermore, it is determined primarily by the particular receptor (in different receptors the same effector system may be activated differently or to a different intensity, depending on the stage of growth); the stage of growth and number of cells are thus also determined empirically in preliminary trials by determining the kinetics of the reporter gene expression in pretest and test cells at different growth stages.

Within the scope of the present invention it has been possible to demonstrate that different cells transformed with TRE-sensor-DNA (TRE-pretest cells) respond to the addition of substances which are known to simulate DAG (this addition being equivalent to the cell of an increase in the DAG-level caused by phospholipase C-activation), thereby inducing the expression of the reporter gene, whilst they do not respond to cAMP-increasing substances. (The sensor DNA contained as regulatory element the 1.3 kb 5'-flanking region of the human ICAM-1 gene (intercellular adhesion molecule 1), which contains a TRE-element, or a plurality of TRE-elements of the ICAM-1 gene arranged in tandem). When the TRE-pretest cells were transformed with a receptor which is specifically coupled to the phospholipase C-signal transduction pathway (the human 5-$HT_2$-receptor, the neurokinin2-receptor and the human $M_3$-receptor were used), the expression of the luciferase gene was measured after treatment with receptor agonists; the induction mediated by the agonists was stopped by the addition of antagonists. On the other hand, this effect could not be detected if the phospholipase C-coupled receptor were transformed in pretest cells which respond to cAMP.

Within the scope of the invention it was also shown that in CHO-cells transformed with CRE-sensor-DNA (CRE-pretest cells) the expression of the CRE-regulated reporter gene is only increased by substances which increase the concentration of cAMP. The treatment of the CRE-pretest cells with substances which bring about or simulate an increase in the $IP_3$/DAG-concentration did not result in the induction of luciferase expression, nor did treatment with substances which are agonists for dopamine and muscarinic acetylcholine receptors. This latter result showed that the cells do not endogenously express these receptors. When the CRE-pretest cells were transfected with a receptor positively coupled to the adenylate cyclase effector system (the dopamine $D_1$-receptor was used), it was possible to induce the luciferase expression with agonists for the $D_1$-receptor and this induction was stopped again by means of antagonists.

With the aid of the present invention, a sensitive and versatile functional method of providing substances which specifically influence a signal transduction pathway in the cell in receptor-dependent manner is provided. The substances found by means of the process according to the invention serve as guide substances for the development of drugs for treating diseases associated with a malfunction of a signal transduction pathway and may be further investigated for their pharmacological properties thereafter, e.g. in secondary screening with primary cells and only after that by clinical trials on animals. The number of animals needed will therefore be significantly reduced by the use of the process according to the invention.

The process according to the invention also has the advantage of being capable of being automated, in that the loading of the cell culture vessels, e.g. microtitre plates with 96 wells, the loading with the test substance solutions, the incubation and washing steps and the measurement, e.g. with a luminometer when luciferase is used as the reporter gene product, are carried out by robots. The process according to the invention is thus suitable for screening programmes with a high throughput capacity, with the capability of testing, for example, 2000 substances or mixtures of substances per week.

With the aid of the process according to the invention it is possible to detect allosterically acting substances and substances which act non-competitively with regard to the ligand binding site.

A further advantage of this system is that, where there are several possible ways for a substance to intervene, for a specific multistage receptor dependent intracellular signal transduction pathway, there are greater prospects of detecting the most favourable parameters for the modulation of a specific signal transduction pathway. The versatility of the system with regard to the large number of receptors and receptor subtypes which may be used enables it to be used to discover pharmacologically active substances for different types of indications. The system according to the invention also makes it possible, with a deliberate choice of specific receptors and receptor subtypes, to distinguish with great specificity between key mechanisms in different cell systems, e.g. the central nervous system and the peripheral system.

With the aid of the process according to the invention it is also possible to clone receptors which are pharmacologically or biochemically characterised and which are known to the ligands. The operator starts with cDNA or genomic banks from which pools are transformed into the corresponding pretest cell line. The expression of the receptor is indicated by an expression of the reporter gene after the receptor has been activated by the binding of a ligand.

EXAMPLES

The invention is explained more fully by means of the Examples which follow:

The activity of the substances used in the Examples is given in the following Table:

| | |
|---|---|
| A23187 | $Ca^{2+}$-ionophor |
| Apomorphine | Agonist for the dopamine-receptor |
| Atropine | Antagonist for muscarinic receptors (non-specific) |
| Bromocryptin | Agonist for the dopamine-receptor |
| Carbachol | Agonist for muscarinic receptors |
| Clozapin | Antagonist for the dopamine-receptor (D4-specific) |

-continued

| | |
|---|---|
| dibutyryl-cAMP (dbcAMP) | membrane-permeable cAMP derivative |
| Dopamine | Agonist for the dopamine-receptor |
| Flupenthixol | Antagonist for the dopamine-receptor (D1-specific) |
| Forskolin | Stimulator of adenylate cyclase (increase in cAMP) |
| Haloperidoi | Antagonist for the dopamine-receptor (D2-specific) |
| IBMX | Phosphodiesterase inhibitor (accumulation of cAMP) |
| Ketanserin | Antagonist for the serotonin-receptor ($5-HT_2$-specific) |
| PMA (TPA) | Protein kinase C activator, simulates $IP_3$/DAG |
| SCH23390 | Antagonist for the dopamine-receptor (D1-specific) |
| Serotonin (5-HT) | Agonist for the serotonin-receptor |
| Spiroperidol (=Spiperon) | Antagonist ($5-HT_{1A}$-receptor > dopamine-receptor) |
| SKF-38393 | Antagonist for the dopamine-receptor (D1-specific) |

Example 1

Preparation of basic vectors for the expression of reporter genes in mammalian cells a) Construction of plasmid pADneo From parts of the plasmids pBluescript SK+ (Short et al., 1988; Stratagene, La Jolla, Calif.) and pRc/CMV (Invitrogen, San Diego, Calif.: Catalogue No. V750-20) a plasmid was prepared which contains the replication origin (ori) and selection marker for ampicillin resistance (Amp, β-lactamase) in E. coli. The intergenic region of M13 makes it possible to prepare single stranded plasmid DNA after superinfection of the transformed bacteria with a helper phage (e.g. R408 or M13K07; Stratagene) to facilitate the sequencing and mutagenesis of the plasmid DNA. Moreover, the neomycin-phosphotransferase gene (neo) under the transcriptional control of the SV40 early promotor (SV40) and the SV40 polyadenylation signal (SV40 poly (A)) are also present.

The plasmid pBluescript SK+ was linearised with HindIII and 100 ng of DNA were placed in a 100 µl PCR mixture (Saiki et al., 1988) (reaction medium: 50 mM KCl, 10 mM Tris-Cl pH 8.3, 1.5 mM $MgCl_2$, 0.01% (w/v) gelatine, 0.2 mM each of the four deoxynucleoside triphosphates (dATP, dGTP, dCTP, dTTP); 2.5 units of Taq polymerase per 100 µl). The primer used consisted of 50 pmol each of the synthetic oligonucleotides EBI-1730 (SEQ ID NO:3) (5'-GGAATTCGCGCCCTGTAGCGGCG-3') and EBI-2134 (SEQ ID NO:4) (5'-CACTGAACTCGAGCAGCTGCGT-TGCTGGCGTTTTTCC-3'). After 5 minutes denaturing at 94° C. PCR was carried out over 10 cycles (conditions of cycle: 40 seconds at 94° C., 45 seconds at 55° C., 5 minutes at 72° C., Perkin Elmer Cetus Thermal Cycler). The oligonucleotides flank the intergenic region of M13 or the replication origin (ori) with the intermediate gene for the β-lactamase. At the same time, at the end of the ori, an XhoI- and at the other end an EcoRI-cutting site are produced (underlined in the oligonucleotide sequence). The reaction mixture was freed from protein by extraction with phenol-chloroform and the DNA was precipitated with ethanol. The DNA obtained was cut with XhoI and EcoRI and after electrophoresis in an agarose gel a fragment of 2.2 kb was isolated.

The plasmid pRc/CMV was doubly cut with EcoRI and SalI, electrophoretically separated in an agarose gel and a 1.5 kb fragment was isolated, containing the SV40- promotor, the neo-gene and the SV40 poly(A)-signal. 100 ng of the 2.2 kb vector DNA were incubated with twice to three times the quantity of 1.5 kb insert DNA overnight at 14° C. with T4 DNA ligase, then *E. coli* JM101 cells made competent for the uptake of DNA (Chung and Miller, 1988) were transformed and selected for ampicillin resistance. From the resulting colonies, the plasmid DNA was dissected out and characterised by cutting with various restriction enzymes. A plasmid of the desired structure was designated pADneo (FIG. 1).

b) Construction of plasmid pADneoTK

Figure 3:
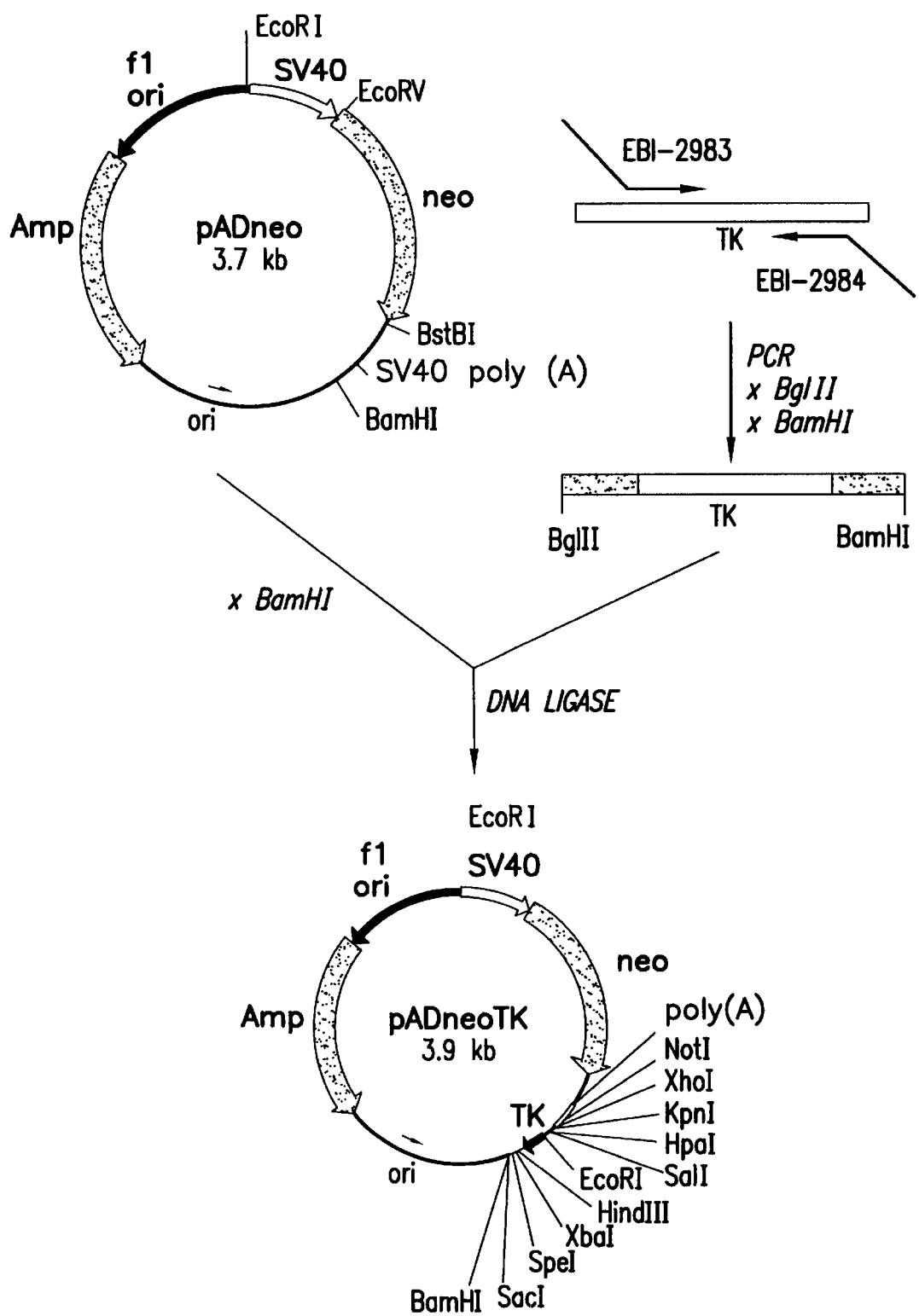
FIG. 3 depicts the construction of the plasmid pADneoTK.

Into the plasmid pADneo was inserted the promotor region of the thymidine kinase (TK)-gene of the Herpes Simplex Virus Type I (HSV-I) flanked by two polycloning sites. This DNA fragment was produced by PCR. As a precursor for the TK-promotor, the plasmid pX1 was used (Wagner et al., 1981) and the polycloning sites were produced by lengthening the amplification primers at the 5'-end, which are no longer complementary to the precursor. 100 ng of plasmid pX1 were subjected to 20 PCR cycles (cycle conditions: 40 seconds at 94° C., 45 seconds at 55° C., 1 minute at 72° C.), with 50 pmol each of the oligonucleotides EBI-2983 (SEQ ID NO:5) (5'-GACTTCAGATCTGCGG-CCGCCTCGAGGGTACCGTTAACGTCGACAAACCC-CGCCCAGCGTCTTG-3') and EBI-2984 (SEQ ID NO:6)(5'-GACTTCGGATCCGAGCTCACTAGTTCTAG-AAAGCTTGACGCTGTTAAGCGGGTCGC-3'). After removal or the Taq polymerase by phenol/chloroform extraction and ethanol precipitation of the DNA, the ends were cut with BamHI and BglII (underlined sequence) and the 0.2 kb fragment was isolated after electrophoresis from an agarose gel (FIG. 2). Then this DNA was ligated with BamHI-linearised plasmid pADneo and *E. coli* JM101 was transformed. A resulting plasmid which contained the TK-promotor in the same orientation as the neo-gene were designated pADneoTK (FIG. 3). It contains 5' from the TK-promotor singular cutting sites for NotI, XhoI, KpnI, HpaI and SalI for the cloning of regulatory sequences which modulate the promotor, and 3' from the TK-promotor singular cutting sites for HindIII, XbaI, SpeI, SacI and BamHI for the insertion of a reporter gene.

c) Construction of plasmid pADneoTKluci

Figure 4A:
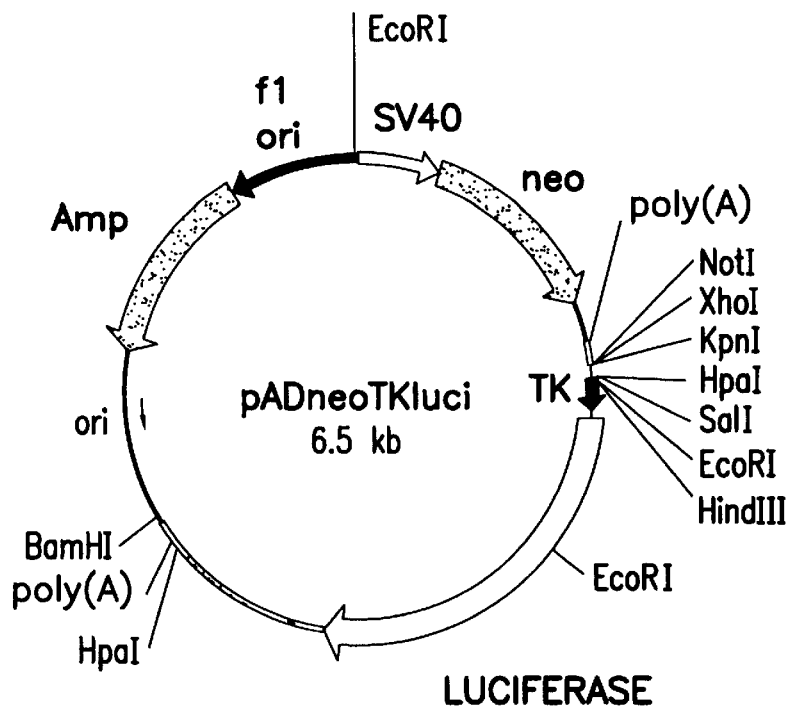
FIG. 4A depicts plasmid pADneoTKluci.

The gene for the *Photinus pyralis* luciferase with the SV40 poly(A) region was isolated from a derivative of plasmid pSV232AL-AΔ5' (De Wet et al., 1987), pBHluc (Voraberger et al., 1991) as a 2.5 kb HindIII-BamHI-fragment. pADneoTK was doubly cut with HindIII and BamHI and ligated with the 2.5 kb HindIII-BamHI fragment from the plasmid pBHluc. A plasmid of the desired structure obtained after transformation of *E. coli* JM101 was designated pADneoTKluci (FIG. 4A). This plasmid allows the expression of luciferase under the control of the TK-promotor in mammalian cells.

d) Construction of plasmid pADneoBGluci

Figure 4B:
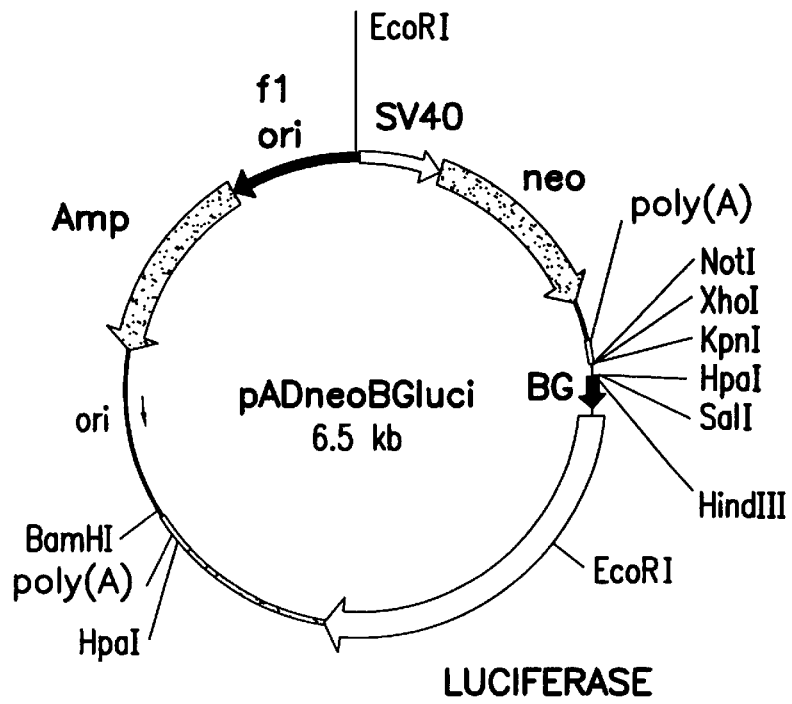
FIG. 4B depicts plasmid pADneoBGluci.

In order to perfect the inductibility of the reporter gene, the TK-promotor was replaced by a minimal promotor sequence of the rabbit β-globin gene. Plasmid pADneoTK-luci was doubly cut with SalI and HindIII and the vector component was isolated from an agarose gel. The β-globin promotor with flanking SalI and HindIII compatible ends was prepared by the synthetic oligonucleotides EBI-3182 (SEQ ID NO:7) (5'-GACTTCGGATCCGAGCTCACTAG-TTCTAGAAAGCTTGACGCTGTTAAGC-GGGTCGC-3') and EBI-3184 (SEQ ID NO:8) (5 '-AGCTTGTAAGCAG-CAGCTGCAGTGCTCTGCCTTTTATGCCCAAGG-3'). The two oligonucleotides were phosphorylated at the 5'-end by incubation with T4-polynucleotide kinase and ATP and subsequently ligated with the vector described above. A plasmid obtained after transformation of *E. coli* JM101 containing the correct sequence was designated pADneoB-Gluci (FIG. 4B).

e) Construction of plasmids pRc/RSVΔNaeI and pRc/RSVneo

For the use of sensor DNA in cell lines which permit the replication of plasmids with SV40 replication origin (e.g. Cos-7 (ATCC CRL1651) and 293 (ATCC CRL1573)), it was desirable for comparative studies with other cell lines to replace the SV40 promotor, which had in its control the neogene in the plasmids described above, for another promotor (e.g. Rous Sarcoma Virus (RSV) long terminal repeat (LTR)).

In order to prepare a new expression cassette for the neo-gene, the plasmid pRc/RSVΔNaeI and pRc/RSVneo described below were prepared.

Plasmid pRc/RSV (Invitrogen, San Diego, Calif.; Catalogue No. V780-20) was cut with NaeI, the 3.8 kb vector component was isolated from an agarose gel and religated. As a result the 1.6 kb fragment with the neo-gene was deleted. The resulting plasmid was called pRc/RSVΔNaeI (FIG. 5).

pRc/RSVΔNaeI was doubly cut with HindIII and XbaI and the DNA ends were blunted by subsequent treatment with the Klenow fragment of the *E. coli* DNA polymerase (Klenow enzyme) in the presence of all four deoxynucleotides.

Figure 6:
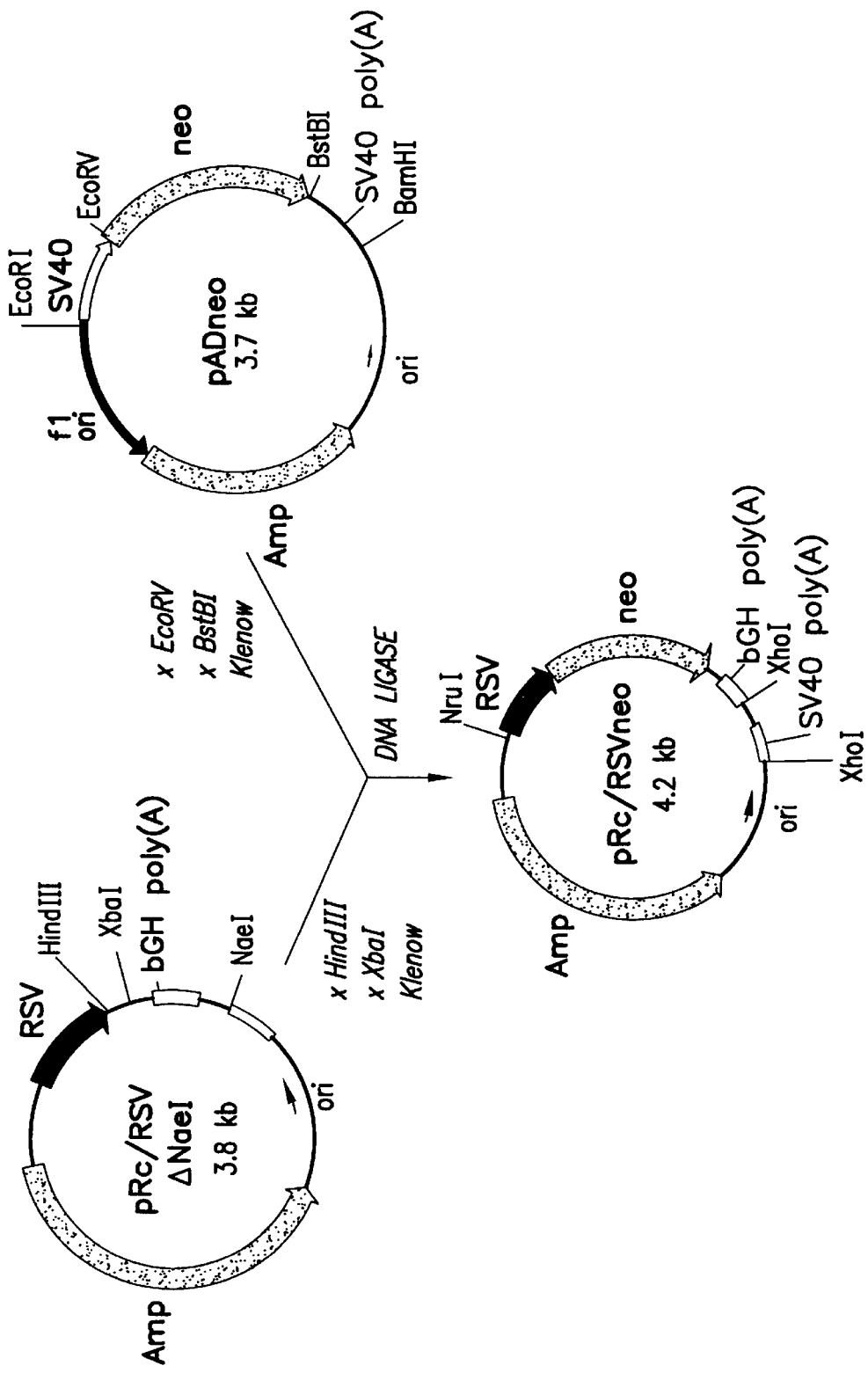
FIG. 6 depicts the construction of the plasmid pRc/RSVneo.

Plasmid pADneo was doubly cut with EcoRV and BstBI, the DNA ends were also blunted by subsequent treatment with Klenow enzyme and a 0.86 kb DNA fragment containing the neo-gene was isolated. After ligation with the vector described above and transformation, a resulting plasmid of the desired structure was called pRc/RSVneo (FIG. 6). This plasmid contains the neo-gene under the transcriptional control of the RSV promotor and the polyadenylation signal of the bovine growth hormone (bGH) and of SV40.

f) Construction of plasmid pADneo2BGluci

The expression cassette SV40 promotor—neo-gene—SV40 poly(A) signal of pADneoBGluci was exchanged for the expression cassette RSV promotor—neo-gene—bGH poly(A) from plasmid pRc/RSVneo.

The plasmid pRc/RSVneo was cut was XhoI and the DNA ends were then blunted with Klenow enzyme. An XhoI-NotI-adaptor, prepared from the oligonucleotides EBI-3285 (SEQ ID NO:9) (5'-TCGATGCGGCCGCGACTTCAG-3') and EBI-3286 (SEQ ID NO:10) (5'-CTGAAGTCGCGGCCGCA-3') was ligated with the cut pRc/RSVneo DNA. In this way the XhoI-cutting site was destroyed and an NotI site (underlined) was inserted. After heat inactivation of the DNA-ligase the DNA was doubly cut with NruI and NotI and a 1.54 kb fragment was isolated from an agarose gel. This DNA fragment contains the RSV-neo-bGH-poly(A)-cassette.

Figure 7:
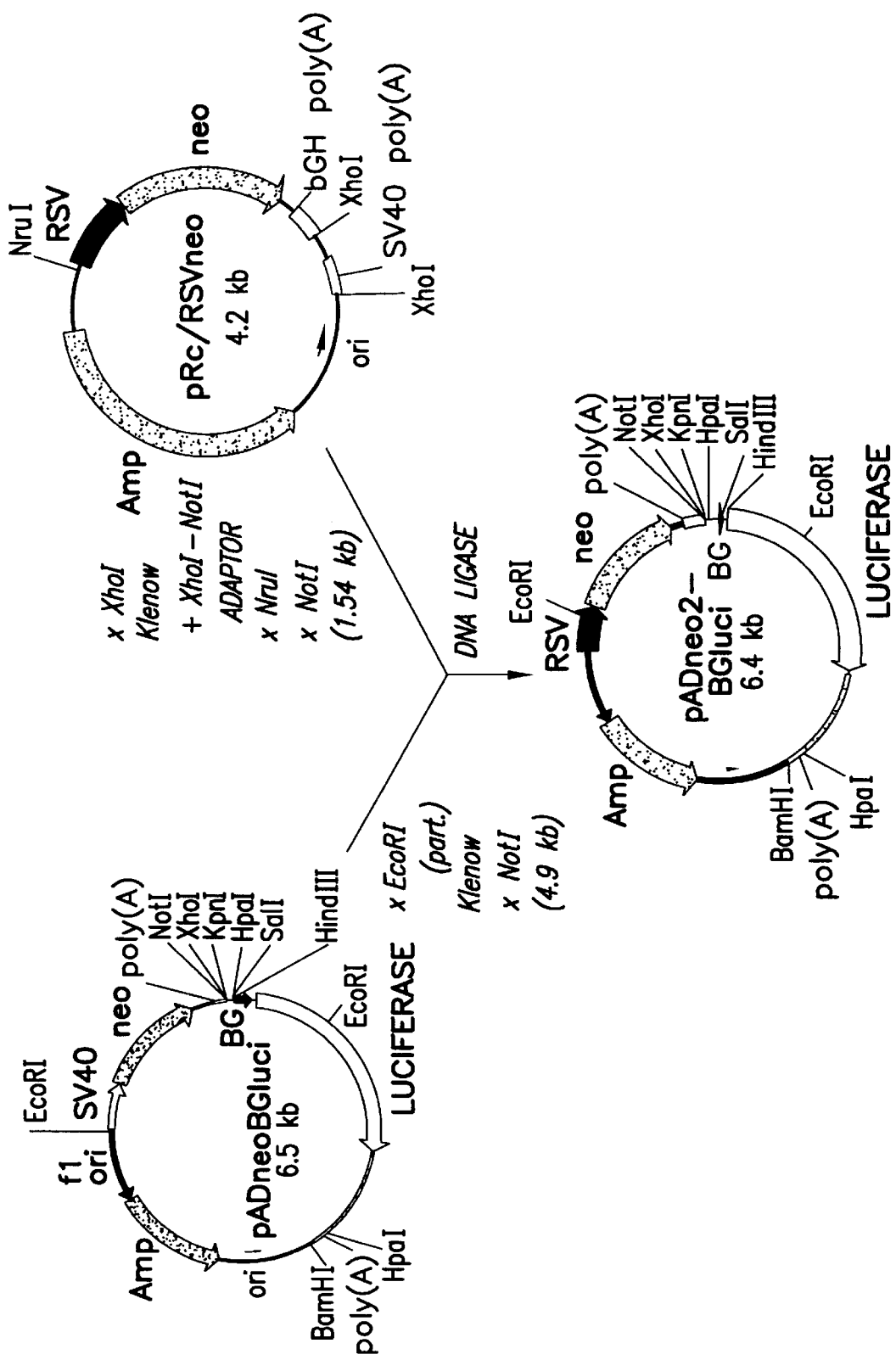
FIG. 7 depicts the construction of the plasmid pADneo2BGluci.

Plasmid pADneoBGluci was partially cut with EcoRI, the ends were straightened with Klenow enzyme and then recut with NotI. A 4.9 kb long DNA fragment was isolated from an agarose gel and ligated with the 1.54 kb NruI—NotI—fragment described above. A plasmid of the desired structure obtained after transformation of *E. coli* was designated pADneo2BGluci (FIG. 7).

g) Construction of reporter plasmids with elements regulatable by cAMP (CRE-sensor-DNA)

In order to control any possible transverse sensitivity of the sensor-DNA for IP$_3$/DAG (containing TRE-elements) the expression cassette for the luciferase reporter gene was placed under the control of various CRE-elements. The choice of CRE-sequences was made in accordance with the composition of characterised CRE-elements (Montminy et al., 1990). The CRE-sequences chosen were those which on the one hand had the perfect 8 base long, palindromic consensus sequence TGACGTCA and on the other hand, if possible, had no longer groupings of GC-pairs, which show similarity for the recognition sequences for Sp1-transcription factors (CCGCCC or GGGCGG) in the surrounding sequences. A number of CRE-sequences were used in tandem to intensify the modulating effect of CAMP. A combination of different CRE-sequences were used to avoid an unfavourable effect on cloning and stability in E. coli if totally identical sequences occur in several repetitions.

By inserting synthetic oligonucleotides into the plasmid pADneo2BGluci 5' from the β-globin promotor, two plasmids were produced having 3 successive CRE-sequences (pADneo2-C3BVC-BGL and pADneo2-C3SVC-BGL), and by combining these plasmids the plasmid pADneo2-C6-BGL with 6 CRE-sequences was prepared.

Figure 8:
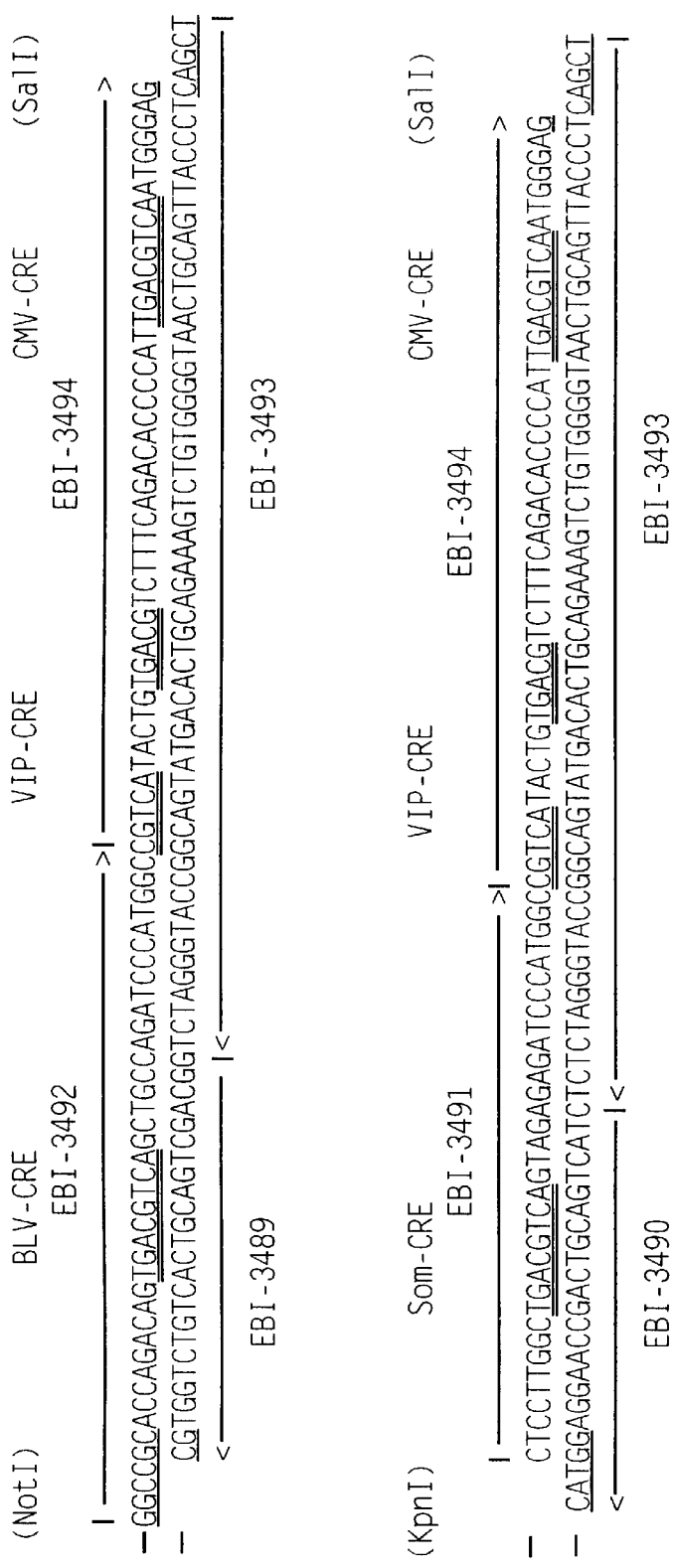
FIG. 8 depicts the oligonucleotide sequence containing three CRE-elements.

The triple CRE-sequences were produced by ligation of two pairs of oligonucleotides with DNA ends complementary with one another (FIG. 8). 20 pmol each of oligonucleotide EBI-3489 (SEQ ID NO:11) (5'-GGCAGCTGACGTCACTGTCTGGTGC-3') and EBI-3491 (SEQ ID NO:12) (5'-CTCCTTGGCTGACGTCAGTAGAGAGATCCCATGGC-3') were incubated in 15 μl of kinase buffer (70 mM Tris-HCl pH 7.6; 10 mM $MgCl_2$, 5 mM dithiotreitol, 2 mM ATP) with 15 units of polynucleotide-kinase for 1 hour at 37° C. and the enzyme was inactivated by heat (5 minutes at 95° C.). In the same way the 5'-end of the oligonucleotides EBI-3490 (SEQ ID NO:13) (5'-CTCTACTGACGTCAGCCAAGGA-GGTAC-3') and EBI-3494 (SEQ ID NO:14) (5'-CGTCAT-ACTGTGACGTCTTTCAGACACCCCATTGACGTCAA-TGGGAG-3') were phosphorylated.

Equimolar amounts of the complementary oligonucleotides without the 5'-phosphate group were mixed with the phosphorylated oligonucleotides: EBI-3492 (SEQ ID NO:15) (5'-GGCCGCACCAGACAGTGACGTCAGCTG-CCAGATCCCATGGC-3') with EBI-3489; EBI-3491 (SEQ ID NO:16) (5'-CTCCTTGGCTGACGTCAGTAGAGAGA-TCCCATGGC-3') with EBI-3490; EBI-3493 (SEQ ID NO:17) (5'-TCGACTCCCATTGACGTCAATGGGGTGT-CTGAAAGACGTCACAGTATGACGGCCATGGGATCT-3') with EBI-3494 and added on by 5 minutes incubation at 56° C. 10 pmol of the now double-stranded oligonucleotide pairs EBI-3489/EBI-3492 and EBI-3493/EBI-3494 were incubated in 30 μl of ligation buffer (70 mM Tris-HCl pH 7.6; 10 mM $MgCl_2$, 5 mM dithiotreitol, 1 mM ATP) with 1 unit of T4 DNA-ligase overnight at 14° C. and the enzyme was subsequently inactivated for 10 minutes at 70° C. The ligated pairs of oligonucleotides were phosphorylated at the 5'-end in 50 μl kinase buffer with 15 units of polynucleotide-kinase for 1 hour at 37° C.

In the same way the pairs of oligonucleotides EBI-3490/EBI-3491 and EBI-3493/EBI-3494 were joined together and then phosphorylated.

Figure 9:
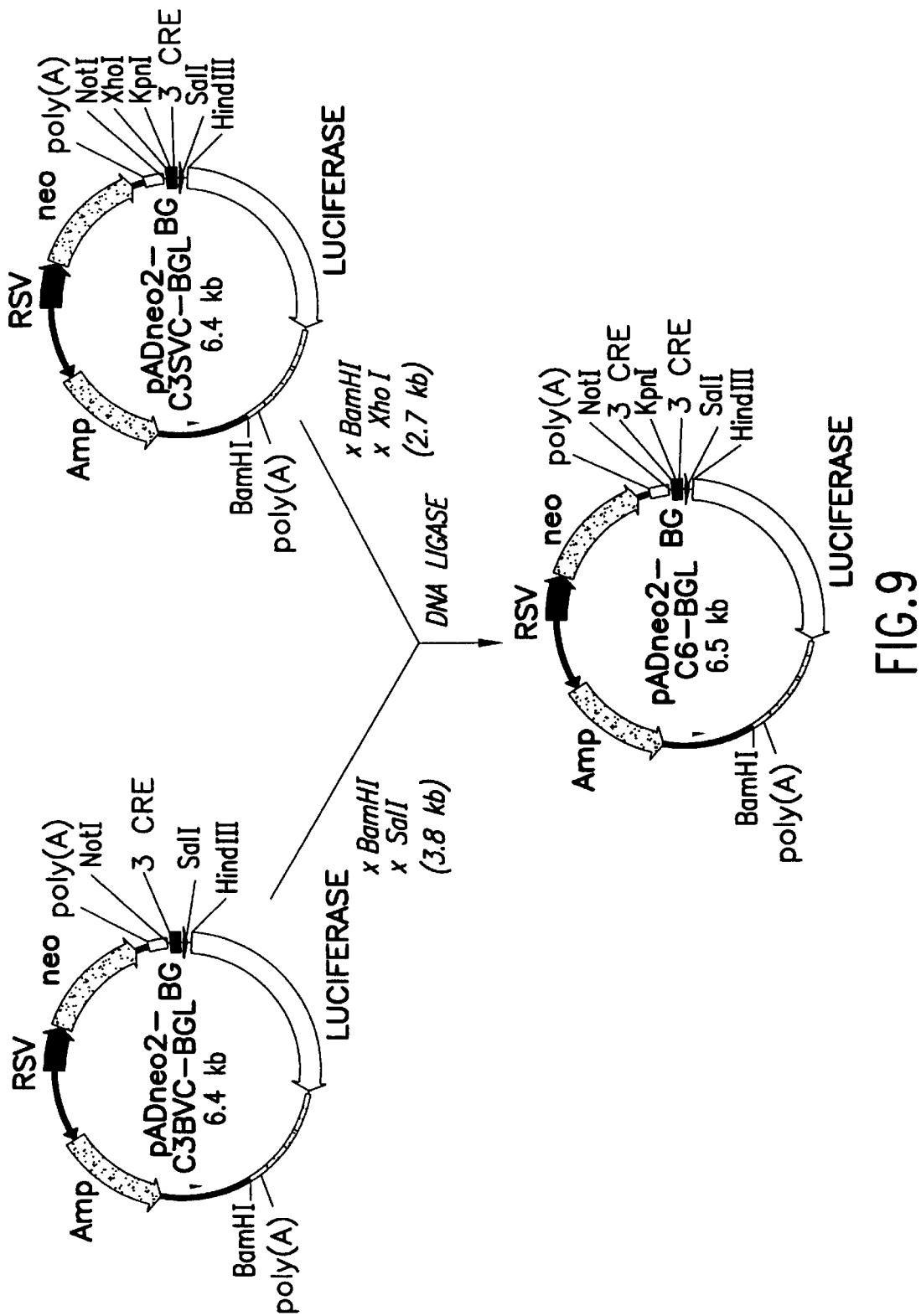
FIG. 9 depicts the construction of the plasmid pADneo2-6C-BGL, containing six CRE-elements.

100 ng of plasmid pADneo2BGluci doubly cut with NotI and SalI were incubated with 0.2 pmol of ligated oligonucleotide complex consisting of EBI-3489/3492/3493/3494 in 20 μl of ligation buffer with 1 unit of T4 DNA-ligase for 4 hours at 22° C. and then E. coli JM101 was transformed. Plasmids obtained from this were subjected to sequence analysis and a plasmid of the desired structure was designated pADneo2-C3BVC-BGL (FIG. 9). This plasmid contains 3 CRE-sequences derived from bovine leukaemia virus LTR (BLV), vasoactive intestinal peptide (VIP) and cytomegalovirus promotor (CMV). (The plasmid name refers to the sequences by the abbreviation "BVC".)

Analogously, the oligonucleotide complex EBI-3490/3491/3493/3494 was cloned in plasmid vector pADneo2BGluci doubly cut with KpnI and SalI and plasmid pADneo2-C3SVC-BGL was obtained (FIG. 9). This plasmid contains 3 CRE-sequences derived from somatostatin (Som), VIP and CMV. (The plasmid name refers to the sequences by the abbreviation "SVC".)

In order to prepare a plasmid with 6 CRE-sequences the plasmid pADneo2-C3BVC-BGL was doubly cut with BamHI and SalI and the 3.8 kb vector component was isolated from an agarose gel. Plasmid pADneo2-C3SVC-BGL was doubly cut with BamHI and XhoI and the 2.7 kb insert was isolated. These two DNA fragments were ligated and E. coli was transformed. A plasmid of the desired structure thus obtained was designated pADneo2-C6-BGL (FIG. 9).

h) Preparation of basic vectors for the expression of genes in mammalian cells with hygromycin B resistance marker Starting from the expression plasmids pAD-CMV1 and pAD-CMV2 (EP-A 393 438) and pHEBo (Sugden et al. 1985) plasmids were produced for the expression of genes or cDNAs under the transcriptional control of the CMV promotor/enhancer and the selection for hydromycin B resistance.

Figure 10:
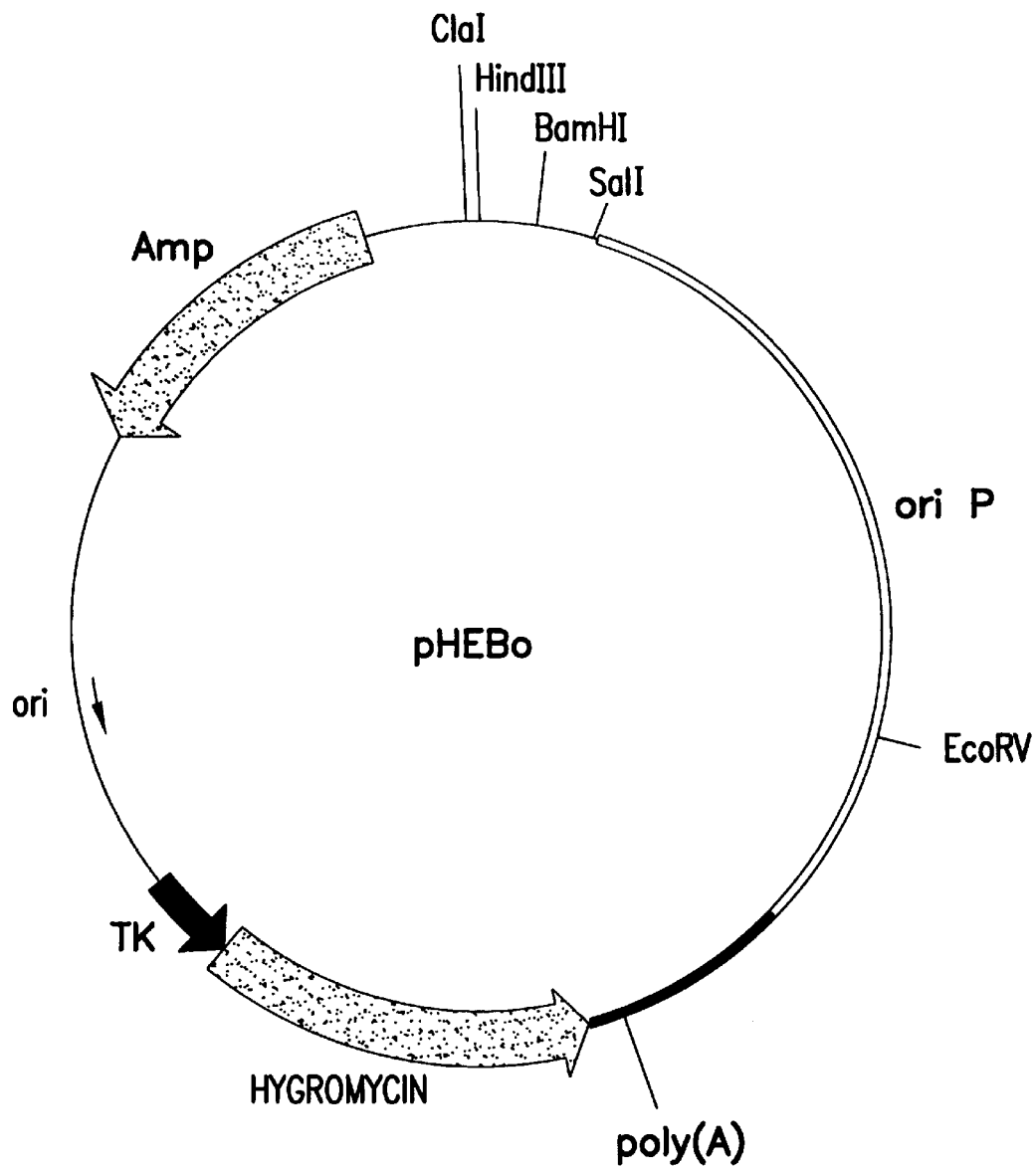
FIG. 10 depicts the plasmid pHEBo.
Figure 11:
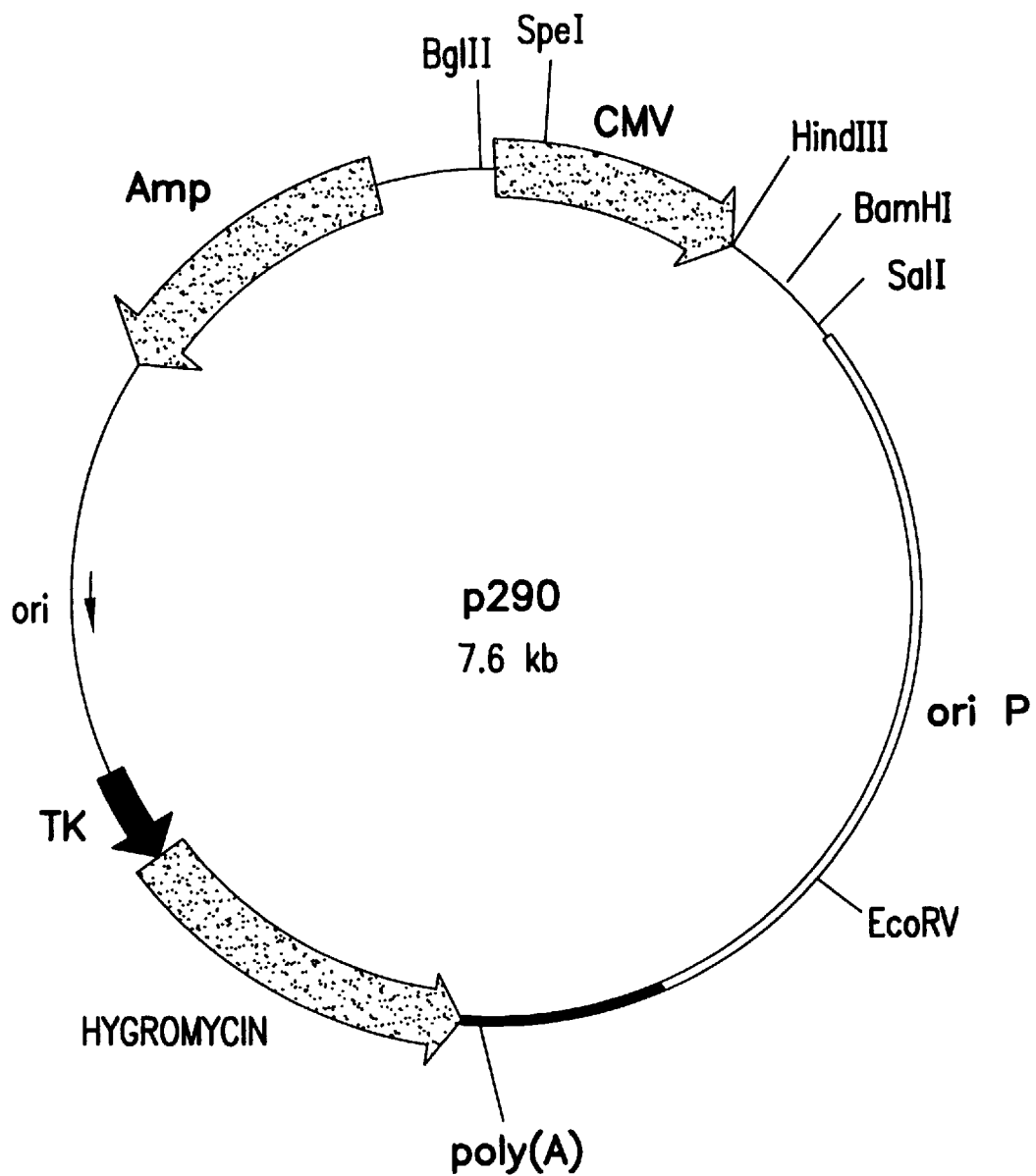
FIG. 11 depicts the plasmid p290.

Plasmid pHEBo (Sugden et al. 1985; FIG. 10) which contains the bacterial hygromycin-B-phosphor transferase gene (Gritz and Davies 1983) under the transcriptional control of the HSV thymidine kinase promotor (McKnight 1980) was cut with ClaI, the DNA ends were filled with Klenow enzyme and then cut with BamHI. Into this vector was cloned a 0.76 kb BamHI-HindIII fragment (BamHI end filled with Klenow enzyme) with the CMV promotor/enhancer sequence (Stinski and Roehr 1985) and plasmid p290 (FIG. 11) was obtained.

Figure 12:
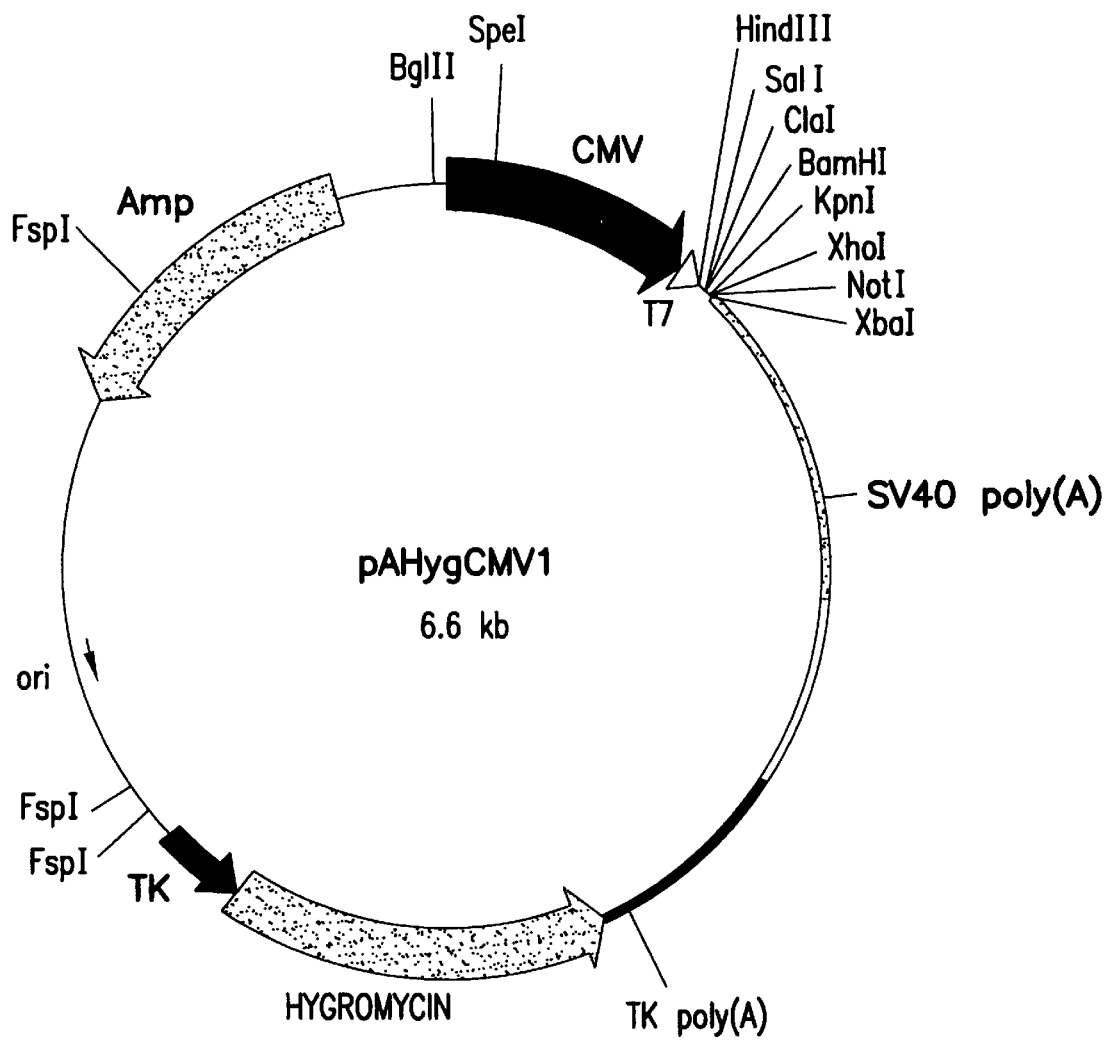
FIG. 12 depicts the plasmid pAHygCMV1.

The SpeI-EcoRV fragment of plasmid p290, which contains CMV promotor and EBV ori P, was cut out. Plasmid pAD-CMV1 was cut with BglII, the DNA ends were blunted with Klenow enzyme and subsequently cut with SpeI. The gel-purified 1.6 kb DNA fragment, which contains CMV promotor, polycloning site, SV40 splice and poly(A) signals, was ligated with the p290 vector part described hereinbefore. The plasmid obtained was designated pAHygCMV1 (FIG. 12).

Figure 13:
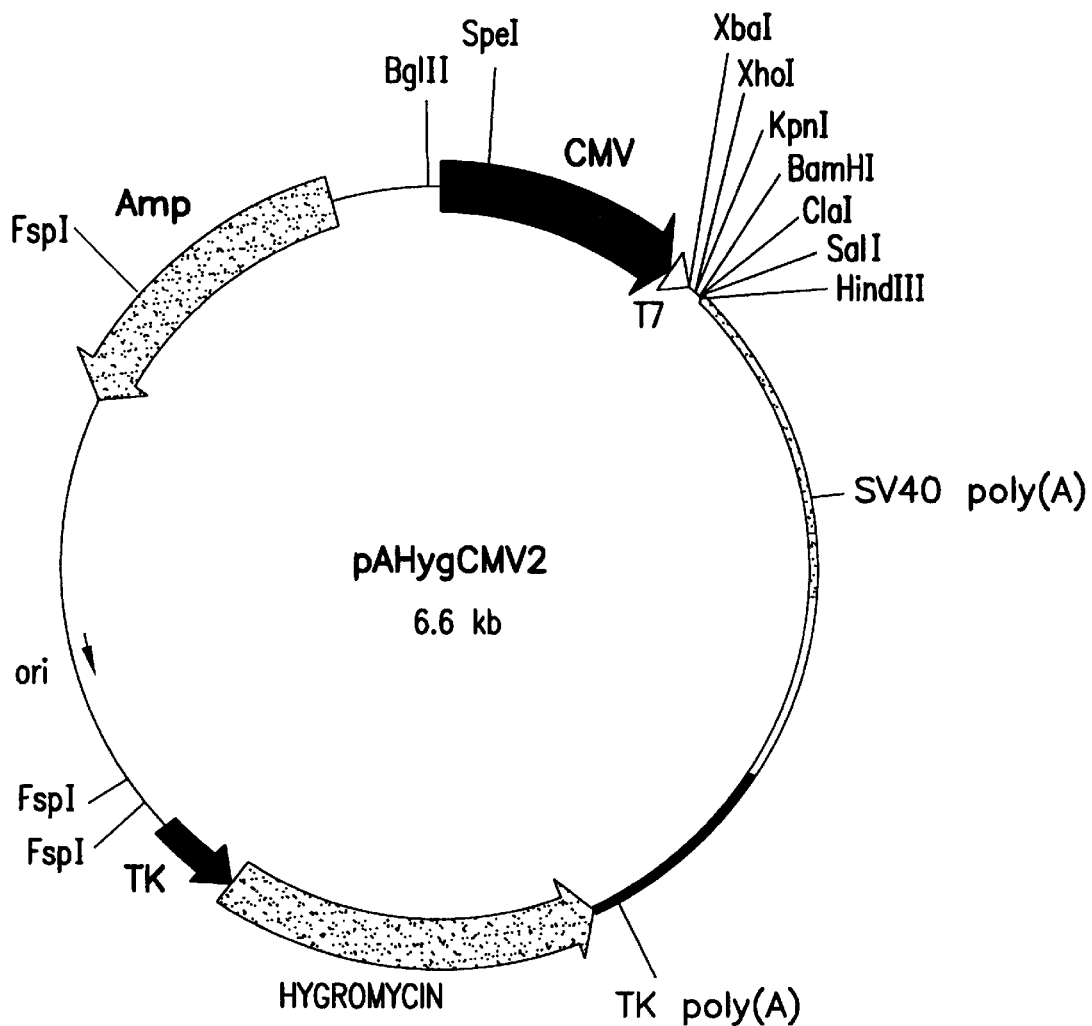
FIG. 13 depicts the plasmid pAHygCMV2.

In the same way the SpeI-BglII fragment was isolated from plasmid pAD-CMV2 and ligated with the p290 SpeI-EcoRV vector part. The resulting plasmid, which contains the polycloning site in the opposite orientation to that in pAHygCMV1 was designated pAHygCMV2 (FIG. 13).

The full nucleotide sequence of the plasmid pAHygCMV1 is in SEQ ID NO:36.

The sections on the plasmid pAHygCMV1 (given in the numbering of the bases) correspond to the following sequences:

| | |
|---|---|
| 1–767 | CMV promotor |
| 768–785 | T7 promotor |
| 794–854 | Polycloning site |
| 854–1552 | SV40 t intron and polyadenylation signals |
| 1553–1736 | 5' non-coding region of the hamster DHFR gene |
| 1737–2261 | EBV ori P partial sequence |
| 2262–2856 | HSV thymidine kinase 3' non-coding region with polyadenylation signal |
| 2857–3912 | Hygromycin B phosphotransferase gene |
| 3913–4161 | HSV thymidine kinase promotor |

| | |
|---|---|
| 4162–6531 | pBR322 vector component |
| 6532–6623 | Linker sequences formed from various cloning processes, partly from plink322 (Maniatis et al. 1982) |

The nucleotide sequence of the plasmid pAHygCMV2 is shown in SEQ ID NO:37. It differs from pAHygCMV1 only in the region of the polycloning site; the cytosine at position 856 in pAHygCMV2 corresponds to cytosine at position 849 in pAHygCMV1.

Example 2

Construction of reporter plasmids with elements (TRE-sensor-DNA) inducible by phorbolesters (TPA)

Cloning and deletion analysis of 1.3 kb of the 5'-flanking region of the human gene for intercellular adhesion molecule ICAM-1 have shown that this fragment i) can be induced by TPA in the lung adenocarcinoma cell line A549 (ATCC CCL 185), but cannot be activated by forskolin, and ii) contains a TPA response element (TRE) with the DNA sequence TGATTCA (Voraberger et al., 1991). The 1.3 kb long ICAM-1 fragment, or nucleotides which contain three TRE-elements in tandem orientation, was therefore used for the construction of vectors in which the luciferase gene can be induced by TPA.

a) Preparation of the plasmid pBHluc1.3

Figure 14:
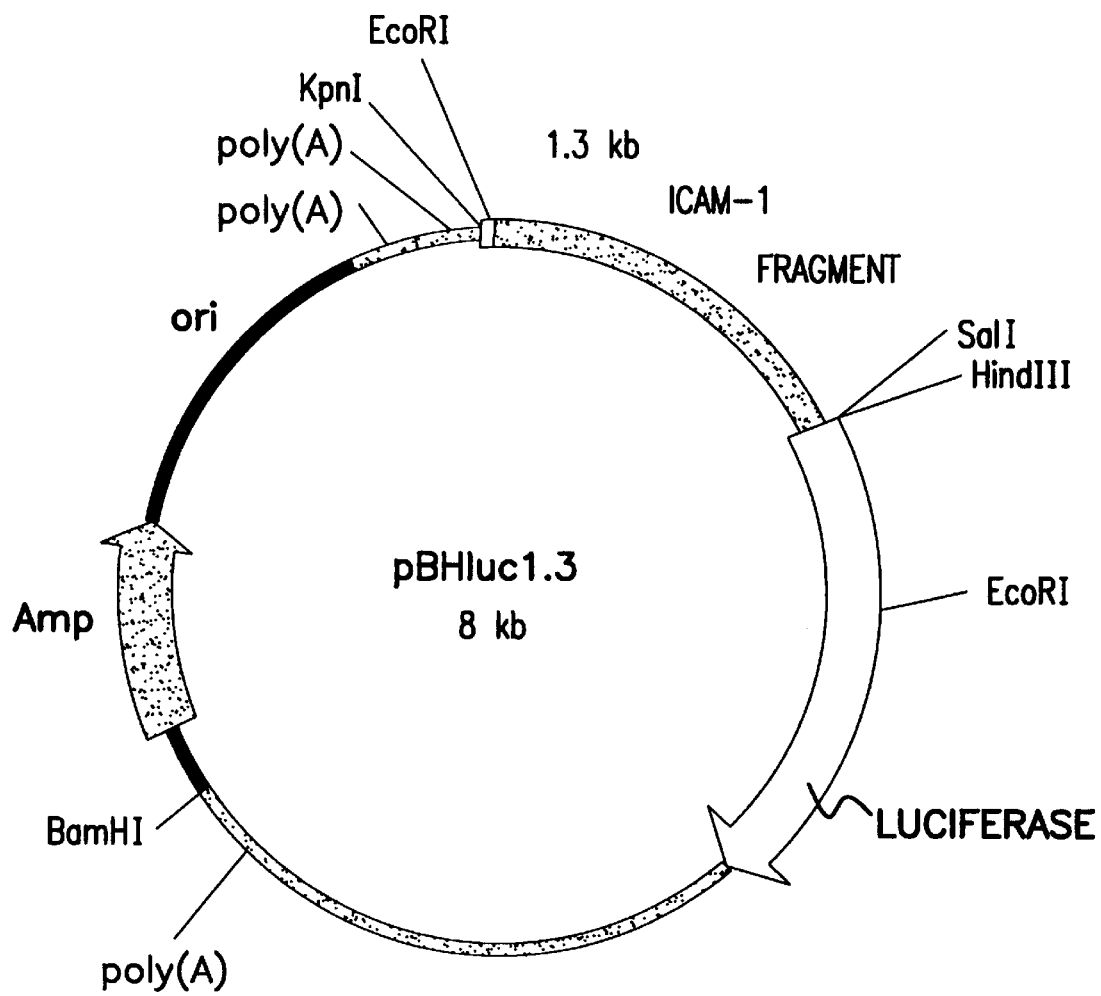
FIG. 14 depicts the plasmid pBHluc1.3.

The plasmid pBHluc1.3 (FIG. 14) contains the 1.3 kb long regulating region of the ICAM-1 gene which precedes the luciferase gene. Its preparation has been described by Voraberger et al., 1991.

b) Preparation of the plasmid pADneo(1.3ICAM)luci (TRE-sensor-DNA)

Figure 15:
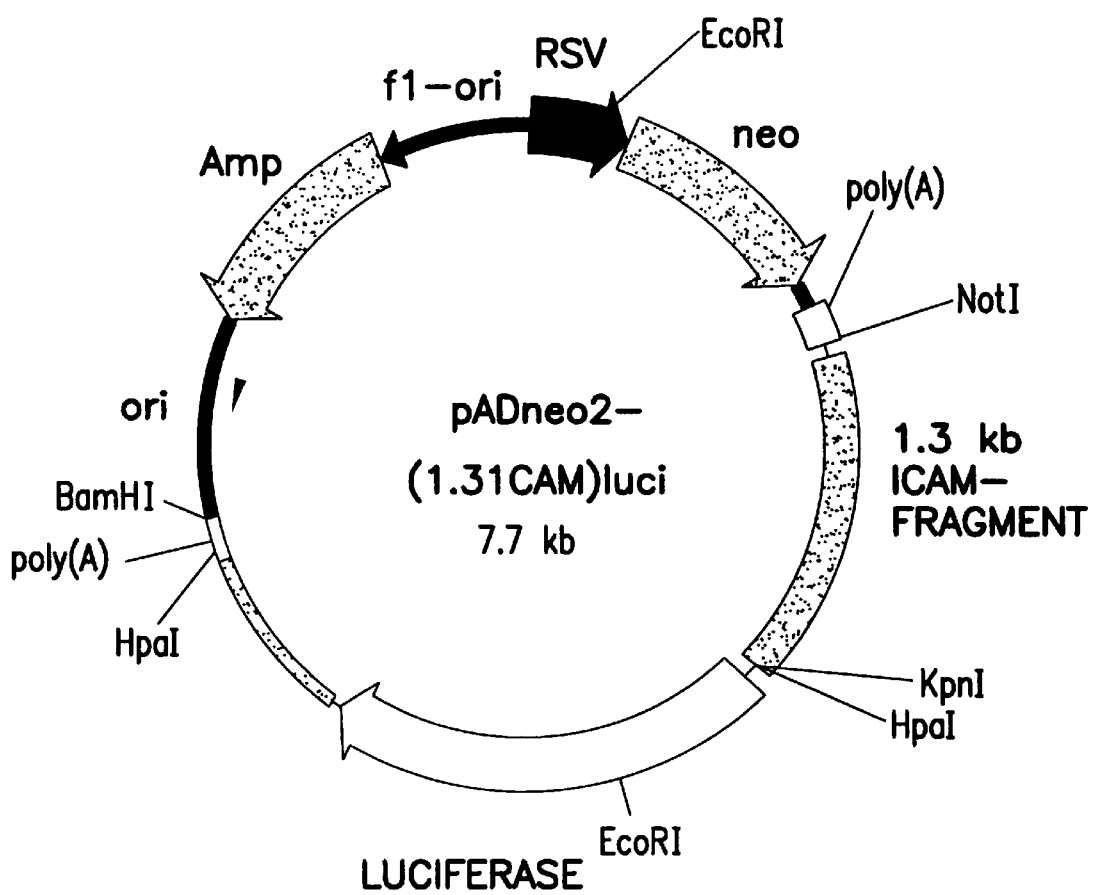
FIG. 15 depicts the plasmid pADneo(1.3ICAM)luci, containing the 5'-regulatory sequence of the ICAM-1 gene.

From the plasmid pADneo2BGluci (see Example 1) first the β-globin promotor was cut out by cutting the plasmid with the restriction enzymes SalI and HindIII, making the DNA ends of the plasmid blunt by adding all 4 dNTPs and Klenow enzyme, and finally religating the plasmid by the addition of T4-DNA-ligase. This plasmid without β-globin promotor, designated pADneo2luci, was then cut with NotI and KpnI, the 1.3 kb long ICAM-1 fragment was cut out of the plasmid Bluescript KS (see Voraberger et al., 1991) with NotI and KpnI, once again, and ligated into pADneo2luci. This plasmid, which was designated pADneo(1.3ICAM)luci (FIG. 15), contains the regulating and promotor region of ICAM-1, preceding the luciferase gene.

c) Preparation of the plasmid pADneo(3TRE)BGluci (TRE-sensor-DNA)

Figure 16:
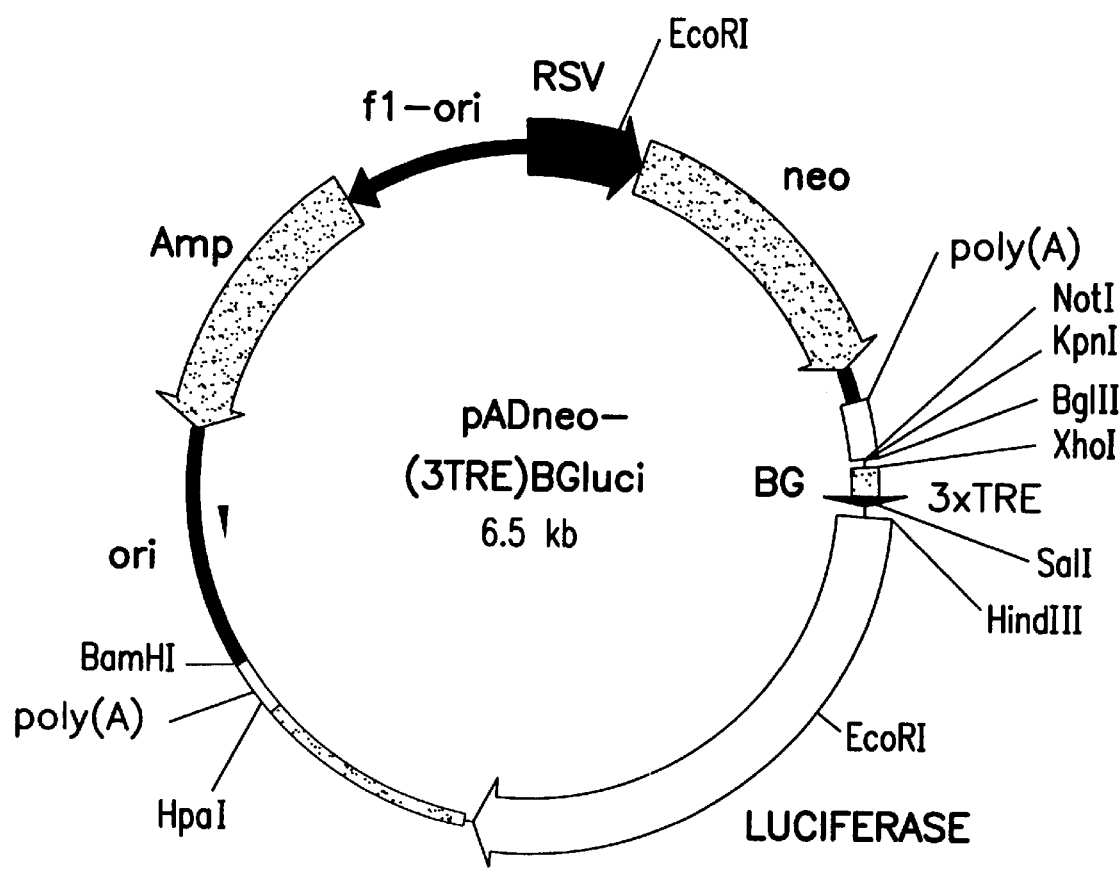
FIG. 16 depicts the plasmid pADneo(3TRE)BGluci, containing three TRE-elements of the ICAM-1-gene.

This plasmid was prepared by inserting synthetic oligonucleotides, coding for the restriction sites KpnI, BglII and XhoI, followed by 3 successive TRE-sequences, 5'from the β-globin promotor of plasmid pADneo2BGluci. To do this, the oligonucleotides EBI-3677 (SEQ ID NO:18) (5'-GGCCGCAGGTACCAGATCTACTCGAGTGTAGACCGTGATTCAAGCTTAGCTGTAGAC-3'), EBI-3671 (SEQ ID NO:19) (5'-GCTTGAATCACGGTCTACACTCGAGTAGATCTGGTACCTGC-3'), EBI-3678 (SEQ ID NO:20) (5'-TCGACTAAGCTTGAATCACGGTCTACAGCTAAG-CTTGAATCACGGTCTACAGCTAA-3') and EBI-3672 (SEQ ID NO:21) (5'-CGTGATTCAAGCTTAGCTGTAG-ACCGTGATTCAAGCTTAG-3') were phosphorylated and equimolar amounts of the complementary oligonucleotides EBI-3677 and EBI-3671, and EBI-3678 and EBI-3672 were added on to one another as described in Example 1. The vector pADneo2BGluci was cut with NotI and SalI, and equimolar amounts of cut plasmid pADneo2BGluci, the oligonucleotide pair EBI-3677/3671 and the oligonucleotide pair EBI-3672/3678 were mixed together and ligated to one another by the addition of T4-DNA-ligase. Resulting plasmids were subjected to sequence analysis and a plasmid containing the desired three TRE-sequences was designated pADneo(3TRE)BGluci (FIG. 16).

d) Preparation of the plasmids pADneo(nTREdx)BGluci

These plasmids contain a number of n TRE-elements the spacing of which from one another amounts to x bases. The plasmids pADneo(3×TREd16)BGluci, pADneo(3×TREd21)BGluci, pADneo(3×TREd24)BGluci and pADneo(3×TREd34)BGluci were prepared using the following oligonucleotides as described in c):

EBI-3775 (SEQ ID NO:22) (5'-GGCCGCAGGTACCAG-ATCTACTCGAGTGTAGACCGTGATTCAAGCTTA-GTGTAGAC-3') and the complementary oligonucleotide EBI-3671 (see above), EBI-3776 (SEQ ID NO:23) (5'-TCGACCTTGAATCACGGTCTACACTAAGCTTG-AATCACGGTCTACACTAA-3') and the complementary oligonucleotide EBI-3777 (SEQ ID NO:24) (5'-CGTG-ATTCAAGCTTAGTGTAGACCGTGATTCAAGG-3') for pADneo(3×TREd16)BGluci;

EBI-3771 (SEQ ID NO:25) (5'-GGCCGCAGGTACCAG-ATCTACTCGAGTGTAGACCGTGATTCAAGCTTAG-CCTG-3') and complementary oligonucleotide EBI-3671 (see above), EBI-3772 (SEQ ID NO:26) (5'-TCGACTA-AGCTTGAATCACGGTCTACACCAGGCTAAGCTTG-AATCACGGTCTACACCAGGCTAA-3') and complementary oligonucleotide EBI-3774 (SEQ ID NO:27) (5'-GTGTAGACCGTGATTCAAGCTTAGCCTGGTGT-AGACCGTGATTCAAGCTTAG-3¹) for pADneo (3×TREd21)BGluci;

EBI-3780 (SEQ ID NO:28) (5'-GGCCGCAGGTACCAG-ATCTACTCGAGTGTAGACCGTGATTCAAGCTTAG-CCTGGCGGTGTAGAC-3') and complementary oligonucleotide EBI-3778 (SEQ ID NO:29) (5'-CCAG-GCTAAGCTTGAATCACGGTCTACACTCGAGTAG-ATCTGGTACCTGC-3'), EBI-3779 (SEQ ID NO:30) (5'-CGTGATTCAAGCTTAGCCTGGCGGTGTAGAC-CGTGATTCAAGCTTAGCCTG-3') and complementary oligonucleotide EBI-3781 (SEQ ID NO:31) (5'-TCGA-CAGGCTAAGCTTGAATCACGGTCTACACCGCCA-GGCTAAGCTTGAATCACGGTCTACACCG-3') for pADneo(3×TREd24)BGluci;

EBI-3786 (SEQ ID NO:32) (5'-GGCCGCAGGTACCAG-ATCTACTCGAGTGTAGACCGTGATTCAAGCTTAG-CCTGGCCGGTTAGCGCGGTGTAGAC-3') and complementary oligonucleotide EBI-3782 (SEQ ID NO:33) (5'-CGCGCTAACCGGCCAGGCTAAGCTTG-AATCACGGTCTACACTCGAGTAGATCTGGTACCT-GC-3'), EBI-3790 (SEQ ID NO:34) (5'-TCGACAGGC-TAAGCTTGAATCACGGTCTACACCGCGCTAACCG-GCCAGGCTAAGCTTGAATCACGGTCTACAC-3') and complementary oligonucleotide EBI-3791 (SEQ ID NO:35) (5'-CGTGATTCAAGCTTAGCCTGGCCGGT-TAGCGCGGTGTAGACCGTGATTCAAGCTTAGCC-TG-3') for pADneo(3×TREd34)BGluci.

In order to obtain the corresponding plasmids with 6 TRE-elements the relevant plasmids with 3 TRE-elements were cut with NotI and XhoI and the corresponding oligonucleotides were ligated in once more. Because of the construction of the oligonucleotides this results in a duplication of the TRE-elements with the corresponding intervals. The resulting plasmids were designated pADneo(6×TREd16)BGluci, pADneo(6×TREd21)BGluci, pADneo(6×TREd24)BGluci and pADneo(6×TREd34)BGluci.

Example 3

Cloning of G-protein coupled receptors and preparation expression plasmid (receptor DNA)

The cDNA of the human 5-HT$_2$-receptor in question was obtained by screening a cDNA bank and cloned into the expression vectors pAD-CMV1 or pAD-CMV2 (EP-A 393 438).

a) Isolation of a clone containing the sequence coding for the human 5-HT$_2$-receptor By homology screening of a human hippocampus cDNA bank in the lambda ZAP vector (Stratagene 936205) with a clone containing the rat 5-HT$_2$-receptor sequence (Julius et al., 1990, Pritchett et al., 1988), a clone was isolated and the insert contained in plasmid pBluescript SK was sequenced. The resulting DNA sequence and the amino acid sequence derived from it are given in SEQ ID NO:1 and SEQ ID NO:2. Comparison of the amino acid sequence of the human 5-HT$_2$-receptor with the published amino acid sequence of the rat 5-HT$_2$-receptor (Julius et al., 1990) resulted in 90% agreement between the two amino acid sequences.

b) Subcloning of the 5-HT$_2$-receptor sequence in the expression vector pAD-CMV2

Figure 17:
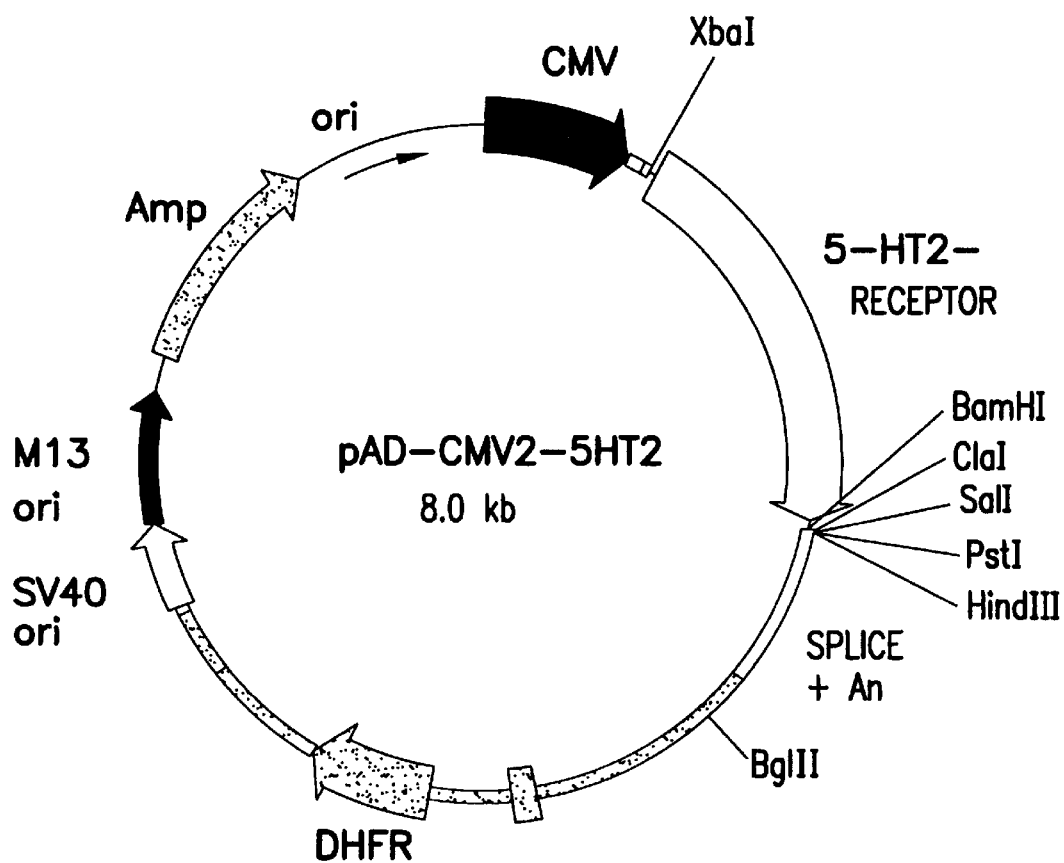
FIG. 17 depicts the plasmid pAD-CMV2-5HT$_2$, containing the sequence coding for the 5HT$_2$-receptor.

The expression vector pAD-CMV2 was cut with EcoRI, the DNA ends were made blunt by the addition of all 4 dNTPs and Klenow enzyme and then the vector was cut with BamHI. Into this vector was ligated the 5-HT$_2$-receptor sequence cut out from the plasmid pBluescript with SmaI and BamHI, and a clone thus obtained was designated pAD-CMV2-5HT$_2$ (FIG. 17).

c) Cloning of the dopamine-D1-receptor sequence into the expression vector pAD-CMV2

Figure 18:
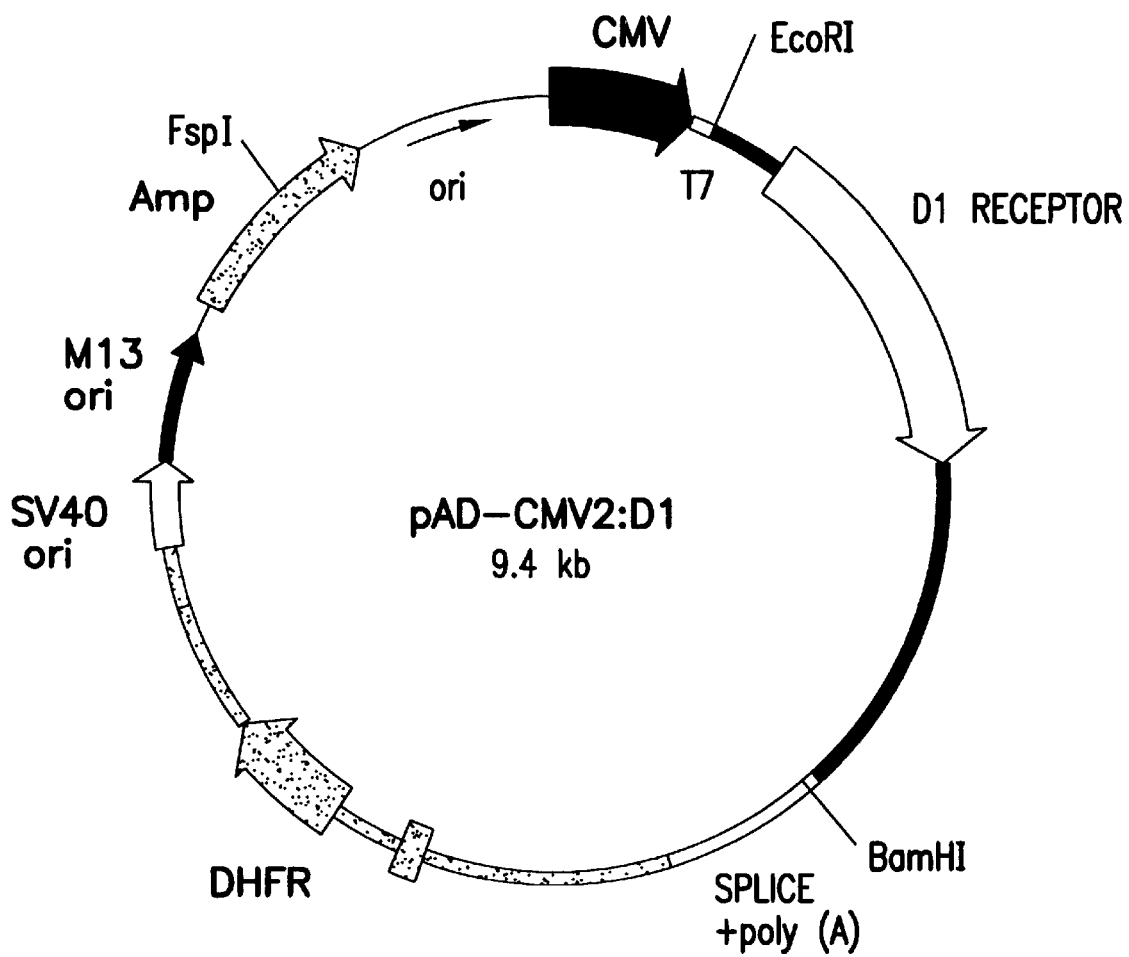
FIG. 18 depicts the plasmid pAD-CMV2: D1, containing the sequence coding for the dopamine-D1-receptor.

Plasmid pHD$_1$-gem, which contains a 3 kb EcoRI-SacI fragment of the human dopamine D1-receptor sequence in pGEM Blue Plasmid Vector (Promega) (Zhou et al., 1990), was doubly cut with EcoRI and BamHI and the 3 kb DNA-insert was isolated. Expression plasmid pAD-CMV2 (EP-A 393 438) was doubly cut with EcoRI and BamHI and the 3 kb D1-receptor fragment was cloned in targeted manner so that the transcription of the dopamine D1 receptor is under the control of the cytomegalovirus (CMV) promotor/enhancer element. The plasmid obtained was designated pAD-CMV2:D1 (FIG. 18).

d) Subcloning of the NK2- or 5HT2-receptor sequence into the expression vector pAHygCMV1

Figure 19A:
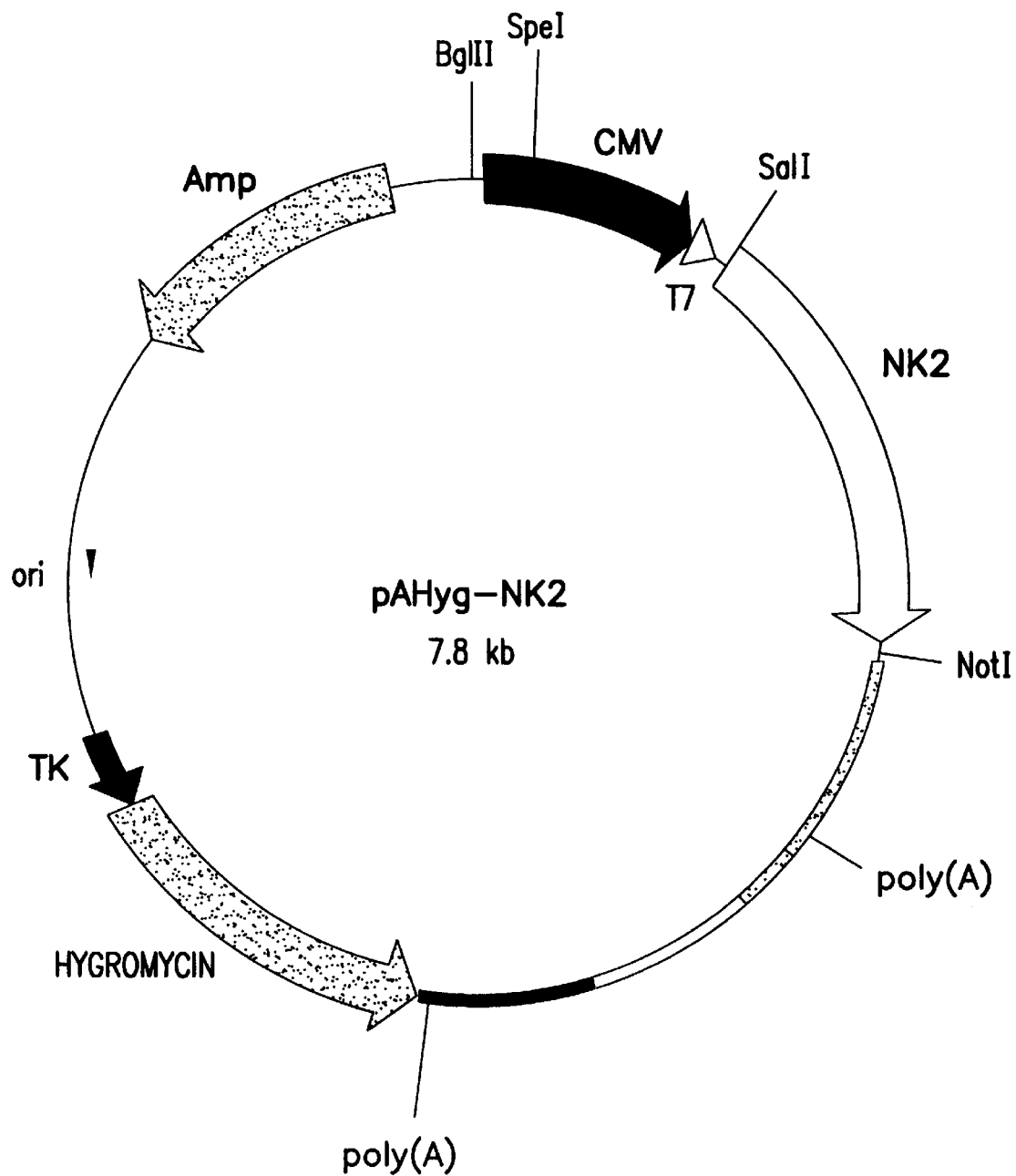
FIG. 19A depicts the plasmid pAHyg-NK2, containing the sequence coding for the NK2-receptor.

The cDNA of the human NK2-receptor was cut out of the plasmid pBluescript-NK2 using the restriction enzymes SalI and NotI, this plasmid containing the NK2-receptor cDNA in the plasmid vector pBluescript SK+ (Stratagene) (Gerard et al., 1990), and the CDNA was cloned into the expression vector pAHygCMV1 (see Example 1 h)) and the resulting plasmid was designated pAHyg-NK2 (FIG. 19A).

Figure 19B:
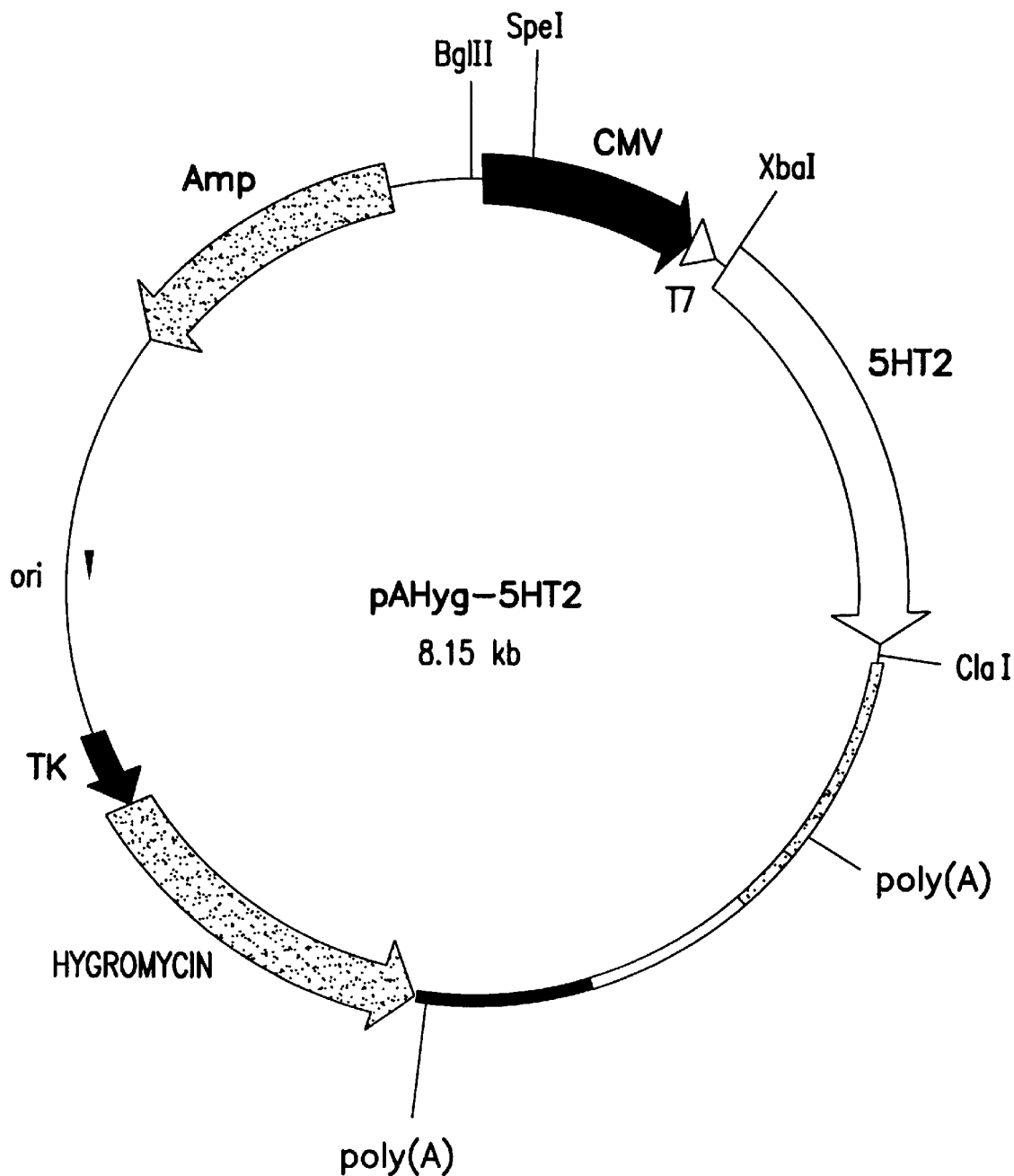
FIG. 19B depicts the plasmid pAHyg-5HT2, containing the sequence coding for the 5HT2-receptor.

The 5HT2-receptor sequence was cut out of the vector pAD-CMV2-SHT2 described above, as a XbaI-ClaI fragment, and cloned into the vector pAHygCMV2 (see Example 1H). The resulting construct was designated pAHyg-5HT2 (FIG. 19B).

Example 4

Induction of TRE-sensor-DNA by TPA in three different pretest cell lines

The following cell lines were transiently transfected with TRE-sensor-DNA (pBHluc1.3): the human lung cancer cell line A549 (ATCC CCL 185), the human cervical cancer cell line HeLa (ATCC CCL 2) and the monkey kidney cell line COS-7 (ATCC CRL 1651), by mixing A549- and COS-7 cells in RPMI-1640 medium (Gibco) and HeLa cells in MEM medium with Earle's BSS (Gibco) with 10% heat inactivated foetal calves' serum (FCS) in each case and incubating the mixtures at 37° C. in 5% CO$_2$. Approximately 1×10$^7$ cells per transfection were detached from the surface of the culture dish using trypsin and centrifuged for 5 minutes at 1200 rpm at ambient temperature (Heraeus Minifuge), washed once with 5 ml of serum-free medium, centrifuged for 5 minutes at 1200 rpm and suspended in 1 ml of serum-free medium. Then the cells were mixed with 250 µg/ml DEAE-dextrane, 5 µg plasmid DNA and 50 µg/ml chloroquin, incubated for 30 minutes at 37° C., washed once with medium containing no FCS and incubated overnight at 37° C. with 10 ml of fresh serum-containing medium. Then the medium was changed and after 4 hours the cells were induced, either with 10 ng TPA/ml medium or with 20 µM forskolin. After another 18 hours the cells were washed with PBS, released from the petri dish using a rubber scrapper and centrifuged for 5 minutes at 1200 rpm at ambient temperature (Heraeus Minifuge). The cells were lysed by the addition of 100 µl lysing buffer (1% Triton X-100, 25 mM glycylglycine pH 7.8, 15 mM MgSO$_4$, 4 mM EDTA and 1 mM DDT), the lysate was centrifuged for 5 minutes and the supernatant was transferred into a fresh test tube. The luciferase assay (De Wet et al., 1985) was carried out by adding 30 µl of the supernatant to 350 µl of assay buffer (25 mM glycylglycine pH 7.8, 5 mM ATP, 15 mM MgSO$_4$), placing the test tube in the luminometer Lumat 9501 (Berthold) and starting the reaction by injecting 300 µl of injection buffer (0.2 mmM luciferin, 20 mM glycylglycine pH 7.8). The measuring time for light emission was 10 seconds.

a) Induction of pBHluc1.3 by TPA but not by forskolin

Figure 20:
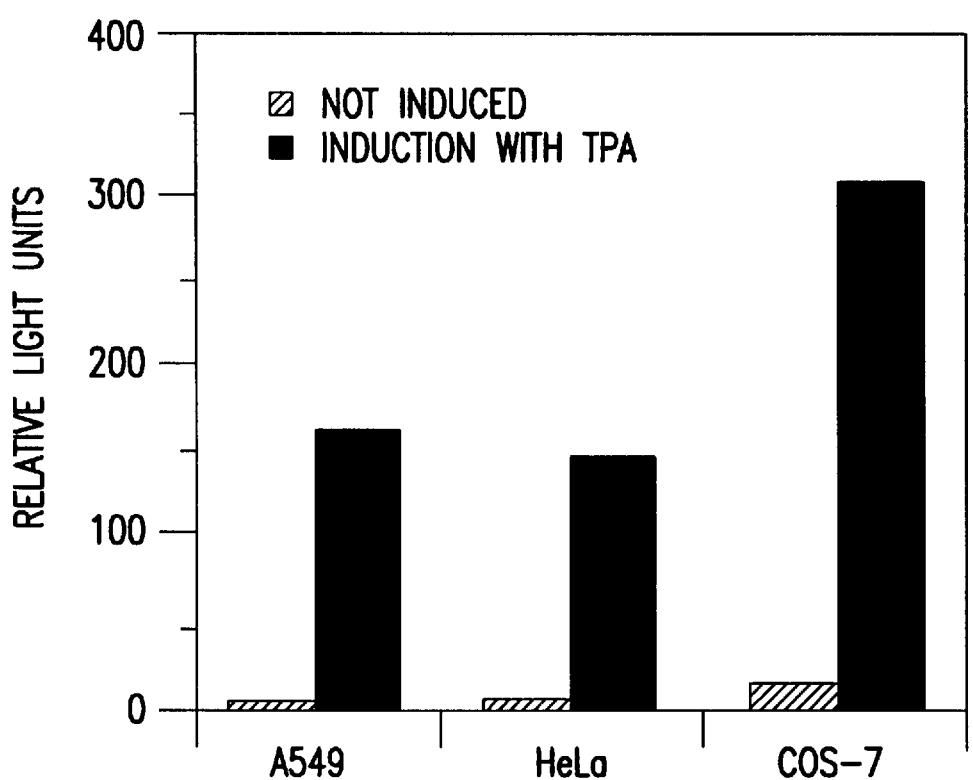
FIG. 20 depicts a bar graph showing the induction of TRE-sensor-DNA (pBHluc1.3) by TPA in the cell lines A549, HeLa and COS-7.
Figure 21A:
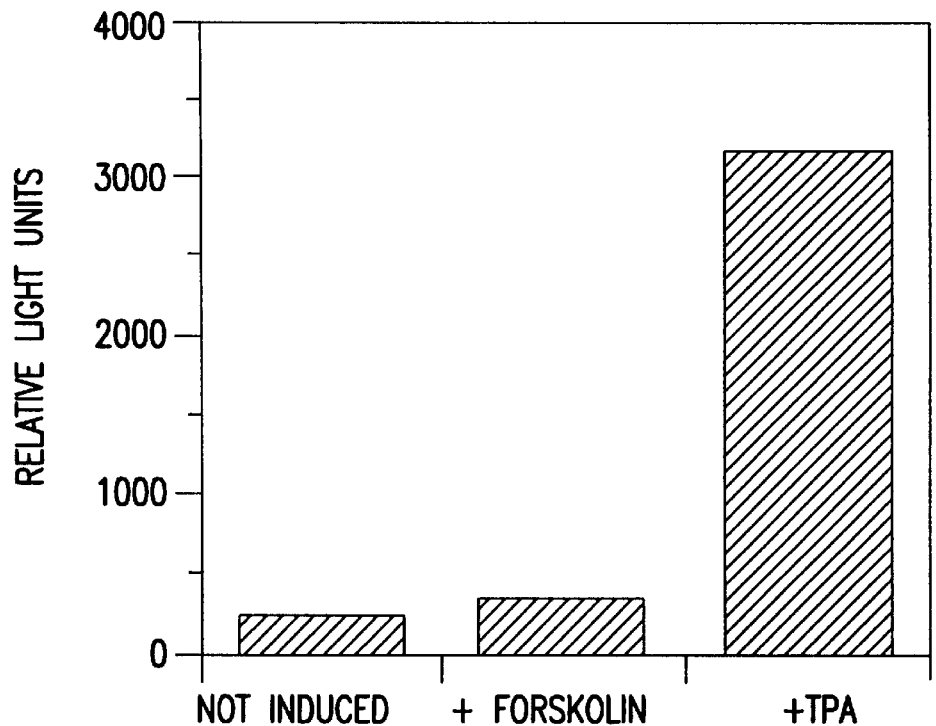
FIG. 21A depicts a bar graph showing the induction of TRE-sensor-DNA (pBHluc1.3) by TPA, but not by forskolin, in HeLa-cells.
Figure 21B:
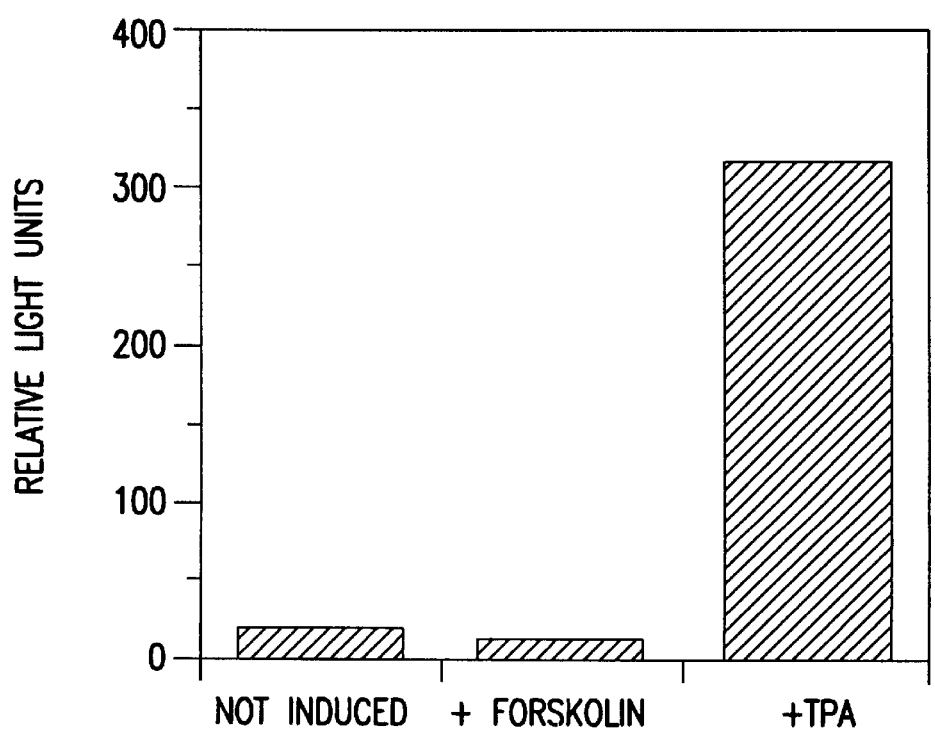
FIG. 21B) depicts a bar graph showing the induction of TRE-sensor-DNA (pBHluc1.3) by TPA, but not by forskolin, in COS 7-cells.

The cell lines A549, HeLa and COS-7 were transiently transfected as described above by the addition of plasmid pBHluc1.3 and induced by the addition of TPA. Cells which were only transfected but not induced were used as a negative control. After the specified incubation time the cells were lysed and the luciferase assay was carried out. The results of the experiment are shown in FIG. 20 and indicate that plasmid pBHluc1.3 is inducible more than 10-fold in the cells tested. Voraberger et al., 1991 showed that this construct in A549 cells cannot be induced by forskolin. In order to verify this result for HeLa and COS-7 cells as well, these cells were transfected once more with pBHluc1.3 in another experiment and induced either with TPA or with forskolin, again using non-induced cells as control. As the result of these experiments it was shown that HeLa and COS-7 cells could also be induced by TPA but not by forskolin, as can be seen in FIGS. 21A and 21B.

b) Inductions of pADneo(3TRE)BGluci by TPA but not by forskolin

Figure 22:
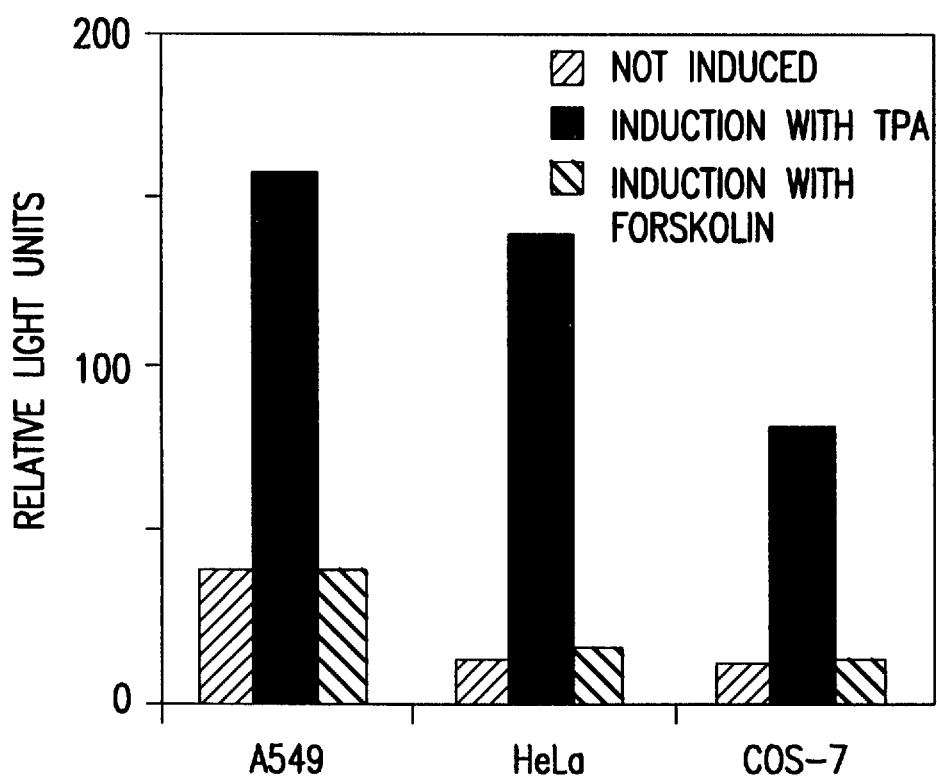
FIG. 22 depicts a bar graph showing the induction of TRE-sensor-DNA (pADneo(3TRE)BGluci) by TPA, but not by forskolin in the cell lines A549, HeLa and COS 7.

The cell lines A549, HeLa and COS-7 were transiently transfected by the addition of plasmid pADneo(3TRE)BGluci and induced by the addition of TPA or forskolin. Once again, cells which were only transfected but not induced were used as a negative control. After the specified incubation time the cells were lysed and the luciferase assay was carried out. The results of the experiments are shown in FIG. 22 and indicate that this vector, which contains only the TRE-elements of the ICAM-1 gene, can be induced in the tested cells by TPA but not by forskolin.

c) Induction of the plasmids pADneo(nTREdx)BGluci by TPA but not by forskolin

The cell lines COS-7 and A549 were transiently transfected by the addition of plasmid pADneo(3×TREd16)BGluci, pADneo(3×TREd21)BGluci, pADneo(3×TREd24)BGluci, pADneo(3×TREd34)BGluci, pADneo(6×TREd16)

Figure 23A:
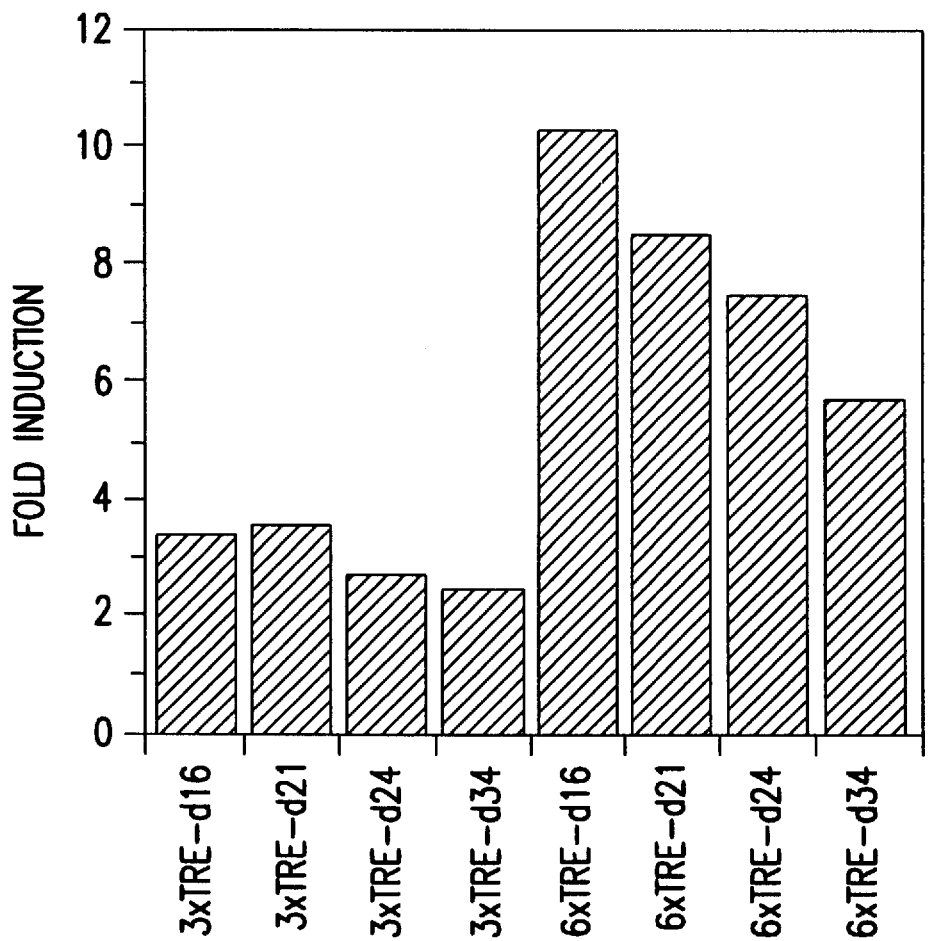
FIG. 23A depicts a bar graph showing the induction of TRE-sensor-DNA in which three or six TRE-elements are contained at different spacings from one another, by TPA in COS 7-cells.
Figure 23B:
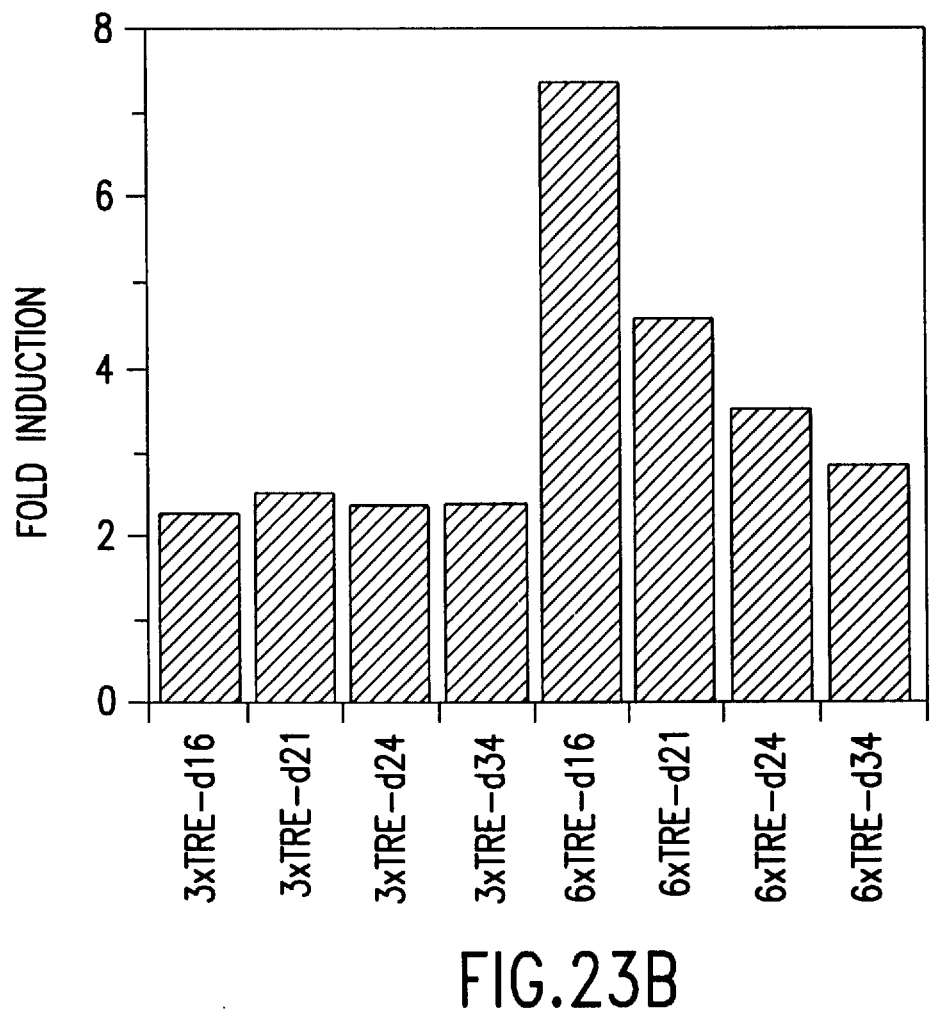
FIG. 23B depicts a bar graph showing the induction of TRE-sensor-DNA in which three of six TRE-elements are contained at different spacings from one another, by TPA in A549-cells.

BGluci, pADneo(6×TREd21)BGluci, pADneo(6×TREd24) BGluci or pADneo(6×TREd34)BGluci and induced by the addition of TPA or forskolin. Once again, cells which had been only transfected but not induced were used as negative control. After the specified incubation period the cells were lysed and the luciferase assay was carried out. The results of the experiment are shown in FIGS. 23A and 23B and demonstrate that i) the induction with TPA for the constructions with 6 TRE-elements is greater than for the constructions with 3 TRE-elements (none of the constructions can be induced with forskolin), and ii) the induction with TPA for the constructions with 6 TRE-elements is higher when the spacing of the TRE-elements is smaller than when the spacing of the TRE-elements is greater.

Example 5

Receptor-mediated induction of TRE-sensor-DNA

Figure 24:
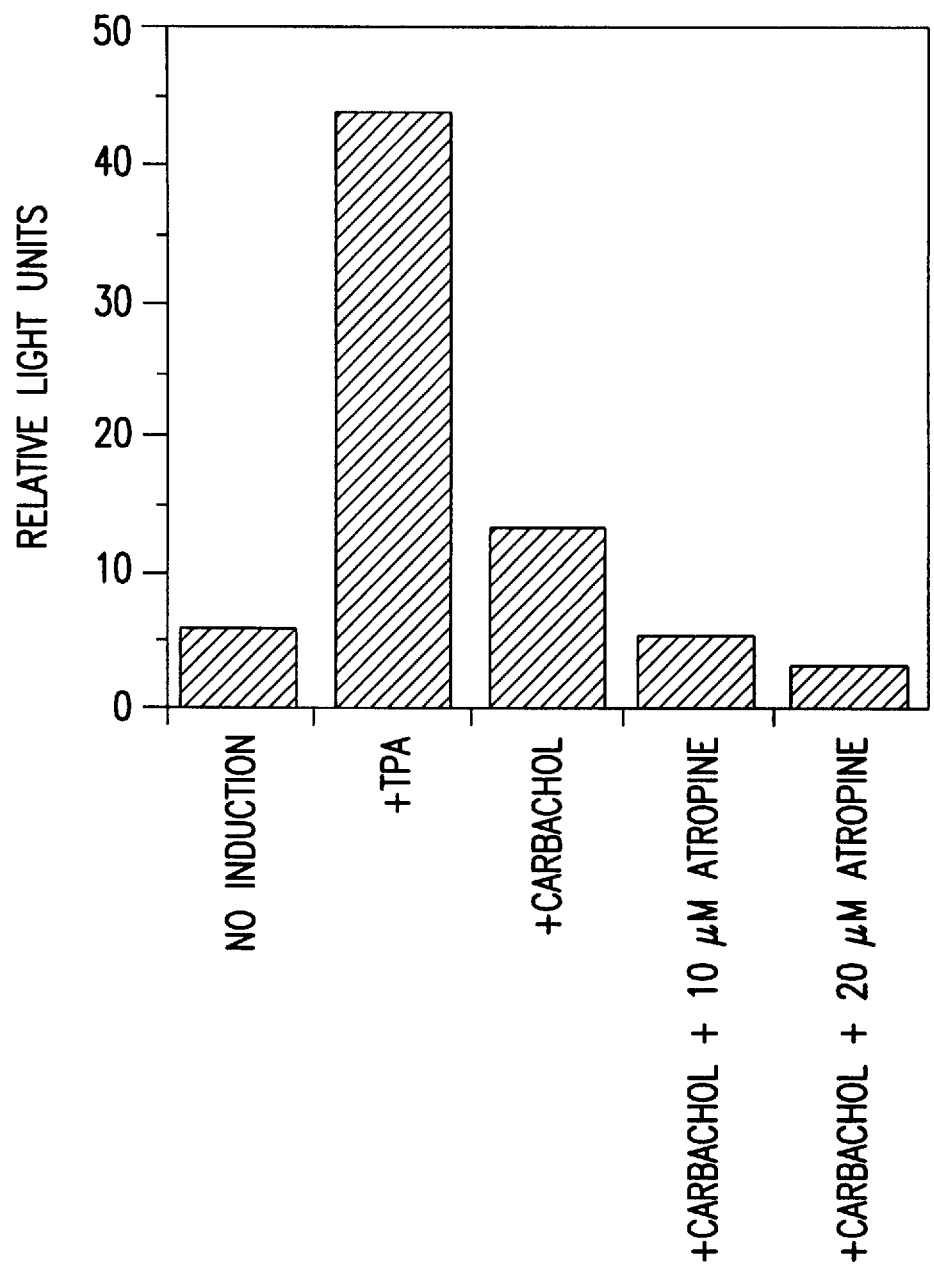
FIG. 24 depicts a bar graph showing the induction of TRE-sensor-DNA (pADneo(3TRE)BGluci) by binding an agonistically acting substance to the muscarinic M3-receptor in COS 7-cells.
Figure 25:
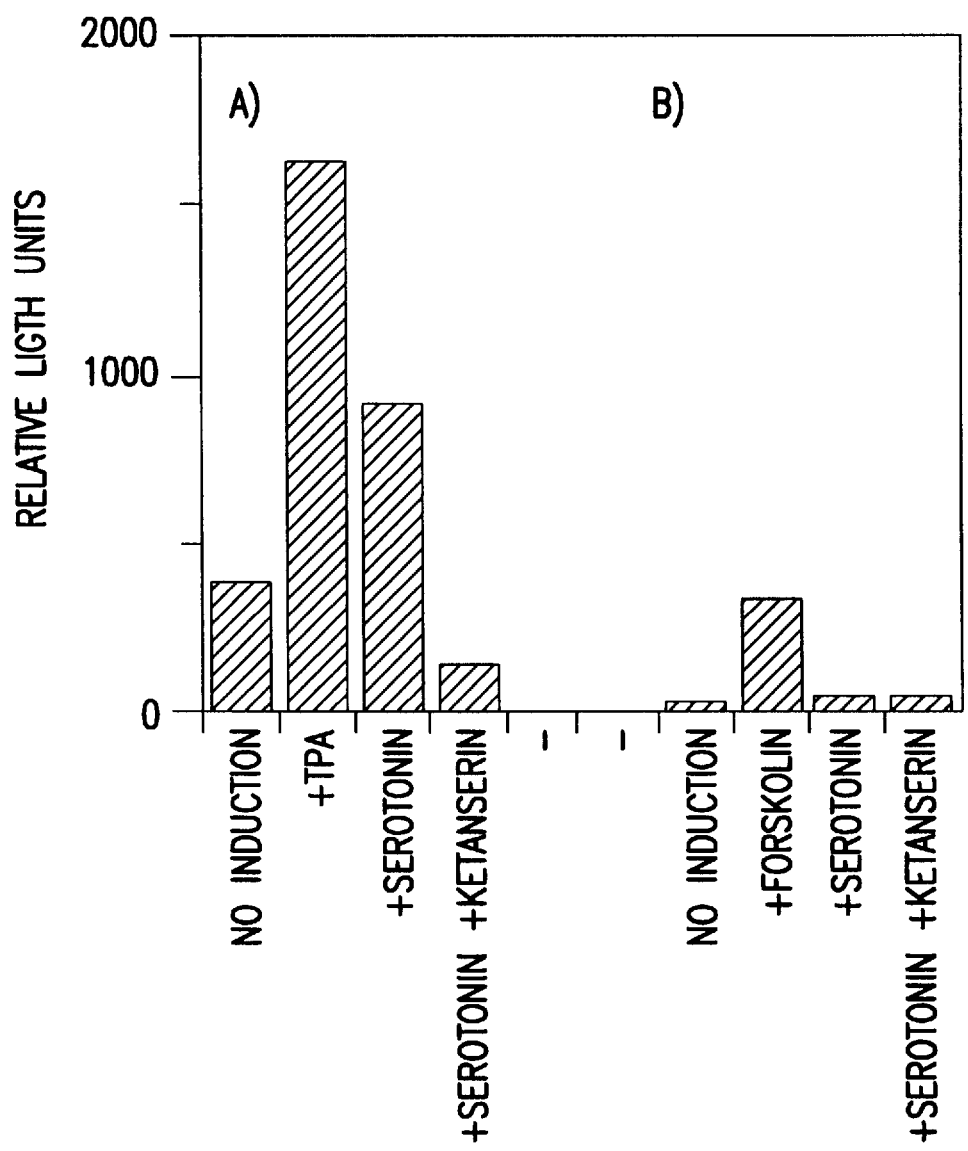
FIG. 25 (Panel A) depicts a bar graph showing the induction of TRE-sensor-DNA (pBHluc1.3) by binding an agonistically acting substance to the $5HT_2$-receptor in COS 7-cells, transformed with $5HT_2$-receptor DNA; (Panel B) depicts a bar graph showing the induction of CRE-sensor-DNA (pADneo2-C6-BGL) by a substance which acts agonistically for the $5HT_2$-receptor in COS 7-cells, transformed with $5HT_2$-receptor DNA.
Figure 26:
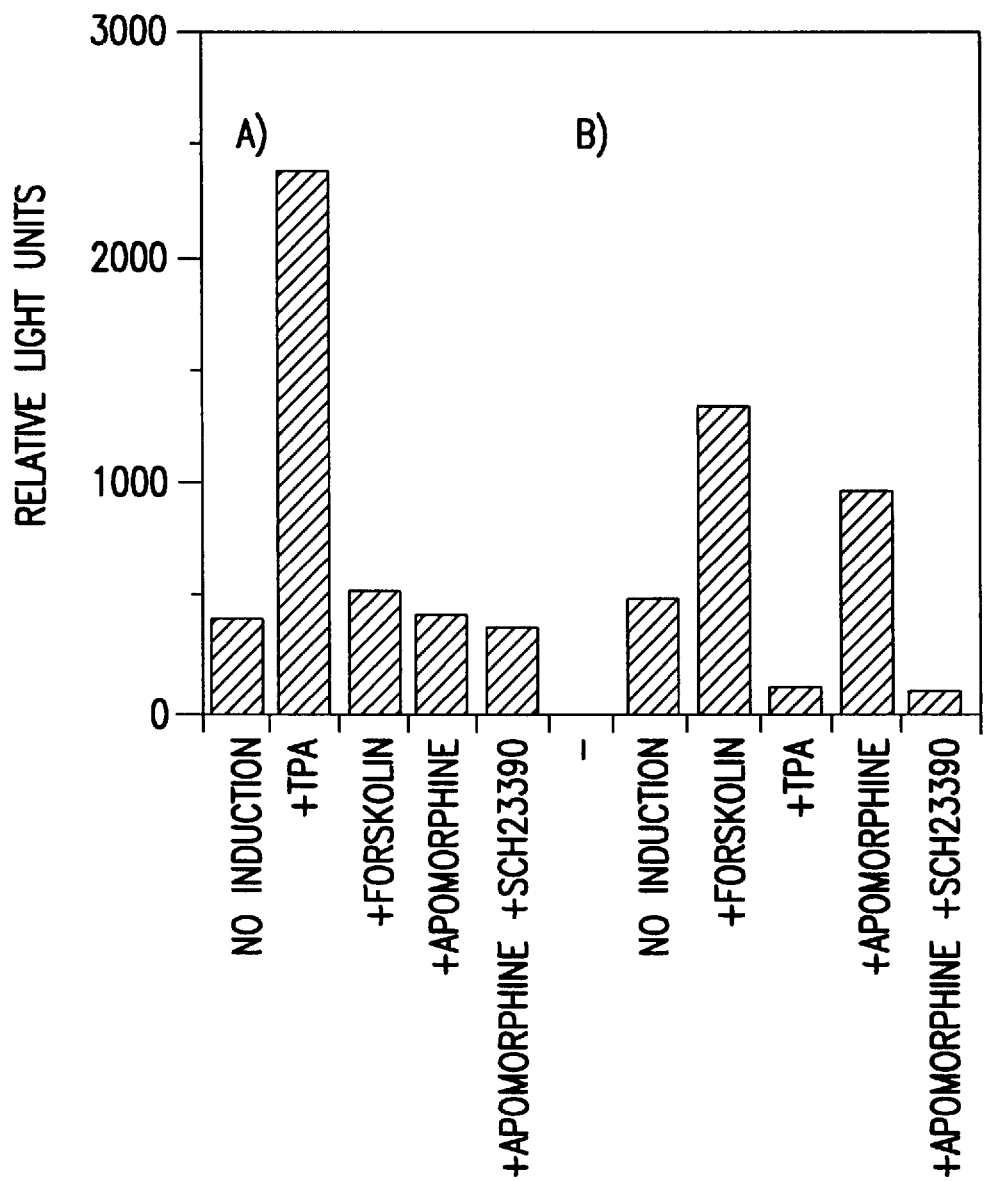
FIG. 26 (Panel A) depicts a bar graph showing the induction of TRE-sensor-DNA (pBHluc1.3) by TPA, but not by a substance which acts agonistically for the dopamine D1-receptor in COS 7-cells, transformed with dopamine D1-receptor DNA; (Panel B) depicts a bar graph showing the induction of CRE-sensor-DNA (pADneo2-C6-BGL) by forskolin and by binding an agonistically acting substance to the dopamine-D1-receptor in COS 7-cells, transformed with dopamine-D1-receptor-DNA.

In order to be able to demonstrate that sensor-DNA which is inducible with TPA can also be induced if the cell line expresses a receptor on the surface which is coupled via G-proteins to the phospholipase C-effector system, and a receptor-specific agonist is added at a suitable time, COS-7 cells were co-transfected with TRE-sensor-DNA and receptor-DNA. The use of COS-7 cells and a receptor-DNA which contains the SV40 replication origin made possible the autonomous replication of the receptor-DNA in high copy numbers and hence allowed high rates for the transient expression of the receptor on the cell surface. The co-transfection was carried out using the DEAE-dextrane method described in Example 4, except that 5 μg each of TRE-sensor-DNA and receptor-DNA were transfected. In this test series, after incubation overnight and changing the medium, either receptor-specific agonists, or agonist and competitive antagonist, or TPA as positive control were added in parallel experiments. Once again non-induced cells were used as a negative control. After 18 hours incubation the cells were lysed and the luciferase assay was carried out as described in Example 4.

a) Induction of pADneo(3TRE)BGluci by binding an agonistically acting substance to the muscarinic M3-receptor COS-7 cells were co-transfected by the addition of sensor-DNA pADneo(3TRE)BGluci and receptor-DNA pCD-M3 (Buckley et al., 1989), containing the sequence of the human muscarinic M3-receptor in the Okayama/Berg pCD expression vector (Okayama and Berg, 1983). Induction was carried out with i) 10 ng/ml TPA (Sigma P8139), ii) 1 mM carbachol (Sigma, C4382), iii) 1 mM carbachol and 10 μM atropine (Sigma A0132) and iv) 1 mM carbachol and 20 μg atropine. The results of the luciferase assay after incubation and lysis of the cells is shown in FIG. 24 and demonstrates that the expression of luciferase is induced both by TPA and by carbachol, an agonist for the muscarinic receptor. The induction mediated by the agonist is prevented by the simultaneous addition of the selective antagonist atropine.

b) Induction of pBHluc1.3, but not of pADneo2-C6-BGL, by binding an agonistically acting substance to the serotonin-5-HT$_2$-receptor COS-7 cells were co-transfected by the addition of sensor-DNA pBHluc1.3 and receptor DNA pAD-CMV2 -5HT$_2$, which contains the sequence of the human 5HT$_2$- receptor in the expression vector pAD-CMV2 (see Example 3). Induction was carried out with i) 10 ng/ml medium TPA (Sigma P8139), ii) 10 μg α-methylserotonin-maleate (RBI Research Biochemicals Incorporated M-110), and iii) 10 μM α-methylserotonin-maleate and 10 μM ketanserin-tartrate (RBI S-006). The results of the luciferase assay after incubation and lysing of the cells is shown in FIG. 25A and demonstrates that the expression of the luciferase is induced both by TPA and by α-methylserotonin-maleate, an agonist for the 5-HT$_2$-receptor. The induction mediated by the agonist is prevented by the simultaneous addition of the selective antagonist ketanserin-tartrate. In a parallel experiment, COS-7 cells were co-transfected by the addition of sensor DNA pADneo2-C6-BGL, which contains 6 CRE-elements, and receptor DNA pAD-CMV2-5HT$_2$. Induction was carried out with i) 20 μM forskolin (Sigma P8139), ii) 10 μα-methylserotonin-maleate (RBI M-110), and iii) 10 μα-methylserotonin-maleate and 10 μM ketanserin-tartrate (RBI S-006). The results of the luciferase assay after incubation and lysing of the cells are shown in FIG. 25B and demonstrate that the expression of luciferase is indeed induced by forskolin but not by the 5-HT2-receptor-agonist α-methylserotonin-maleate. It follows, from the above results, that, depending on 5-HT$_2$-receptors, only regulation elements which respond to IP$_3$/DAG (TRE), but not regulation elements which respond to cAMP (CRE) are selectively activated.

c) Induction of pADneo2-C6-BGL but not of pBHluc1.3 by binding an agonistically acting substance to the dopamine-D1-receptor COS-7 cells were co-transfected by the addition of sensor-DNA pBHluc1.3 and receptor DNA pAD-CMV2-D1, which contains the sequence of the human dopamine-D1-receptor in the expression vector pAD-CMV2 (see Example 3). Induction was carried out with i) 10 ng/ml TPA (Sigma P8139), ii) 20 μM forskolin (Sigma P8139), iii) 1 μM apomorphine (RBI D-004), and iv) 1 μM apomorphine and 1 μM SCH23390 (RBI D-054). The results of the luciferase assay after incubation and lysis of the cells are shown in FIG. 26A) and demonstrates that the expression of the luciferase gene is indeed induced by TPA but not by apomorphine, an agonist for the D1-receptor. In a parallel experiment, COS-7 cells were co-transfected and induced by the addition of sensor-DNA pADneo2-C6-BGL, which contains 6 CRE-elements, and receptor-DNA pAD-CMV2-D1. The results of the luciferase assay after incubation and lysis of the cells are shown in FIG. 26B) and demonstrate that the expression of the luciferase is induced by forskolin and by apomorphine. The induction mediated by the agonist is prevented by the simultaneous addition of the selective antagonist SCH23390. It follows from the above results that the dopamine-D1-receptor only selectively activates regulating elements which respond to the adenylate cyclase signal transduction system (CRE), but not regulating elements which respond to the phospholipase C-signal transduction system (TRE).

Example 6 a) Development of recombinant A549 cell lines which express luciferase depending on the intracellular IP$_3$/DAG concentration (TRE-cell lines)

The TRE-sensor-DNA pBHluc1.3 had been induced in transient transfection experiments in the cell line A549 more than 10 times by the addition of TPA. (Example 4a). In order to produce a stable (pre-)test cell line for substances which influence the expression of the luciferase gene by direct or receptor-mediated modulation of the IP$_3$/DAC-signal transduction pathway, A549 cells were simultaneously transfected with the plasmid pBHluc1.3 and the selection plasmid pRSVneo by electroporation as follows: after removal of the medium the cells were detached from the surface by means of a trypsin/PBS solution, suspended in medium and sedimented for 5 minutes at 250×g. The cells were washed in serum-free RPMI-1640 medium (Gibco), centrifuged again and resuspended in serum-free RPMI-1640 at a density of 1.25×10$^7$ cells/ml. 0.8 ml of cell suspension were combined with 20 μg of pBHluc1.3 and 2 μg of pRSVneo. Both plasmids had previously been linearised with BamHI. The transfection was carried out with the PG200 Progenetor II electroporation apparatus (Hoefer Scientific Instruments) with a single current impulse of 270 V, 1080 μF, 1000 msec. Then the cells were diluted in RPMI-1640 medium, mixed with 10% foetal calves' serum, and sown at a density of 2–5×10$^5$ cells per 90 mm culture dish. From the day after transfection onwards the cells were grown in selection medium (RPMI-1640, enriched with 10% dialysed foetal calves' serum, Na-penicillin G (100 units/ml), streptomycin (50 units/ml) and 800 μg/ml geneticin (G-418, Gibco-BRL).

15–20 days after transfection, individual cell clones were transferred into 96-well microtitre plates and further cultivated. G-418-resistant clones were tested for the inducibility of luciferase expression by the addition of TPA. Approximately 40,000 cells in each clone were sown, in a procedure repeated 6 times, in 200 μl per well of a light-impervious 96-well microtitre plate coated with tissue culture (Microlite™, Dynatech Laboratories) and incubated overnight at 37° C. Three mixtures were treated with 10 ng TPA/ml and incubated for a further 8 hours. Then the medium was removed and the cells were washed twice with PBS. The cells were taken up in 150 μl lysing buffer (25 mM tricine, 0.5 mM EDTA, 0.54 mM sodium tripolyphosphate, 6.5 mM DTT, 16.3 mM MgSO$_4$. 7H$_2$O, 0.1% Triton X-100, 1.2 mM ATP, 0.05 mM luciferin; pH7.8) per batch and the luciferase activity was measured in a 96 well luminometer (ML-1000, Dynatech). Cell clone A20 was selected for further experiments as it showed a measurable base level of luciferase activity as well as being 15–20-times inducible by TPA.

b) Development of recombinant A549 test cell lines which express luciferase as a function of the activation of the human neurokinin 2-receptor This Example illustrates the preparation of a test cell line for the human neurokinin 2 (NK2)-receptor which is coupled to the phospholipase C-signal transduction pathway. This test cell line makes it possible, by measurement of the luciferase activity, to identify substances which modulate the intracellular IP$_3$/DAG concentrations, depending on the receptor.

Figure 27:
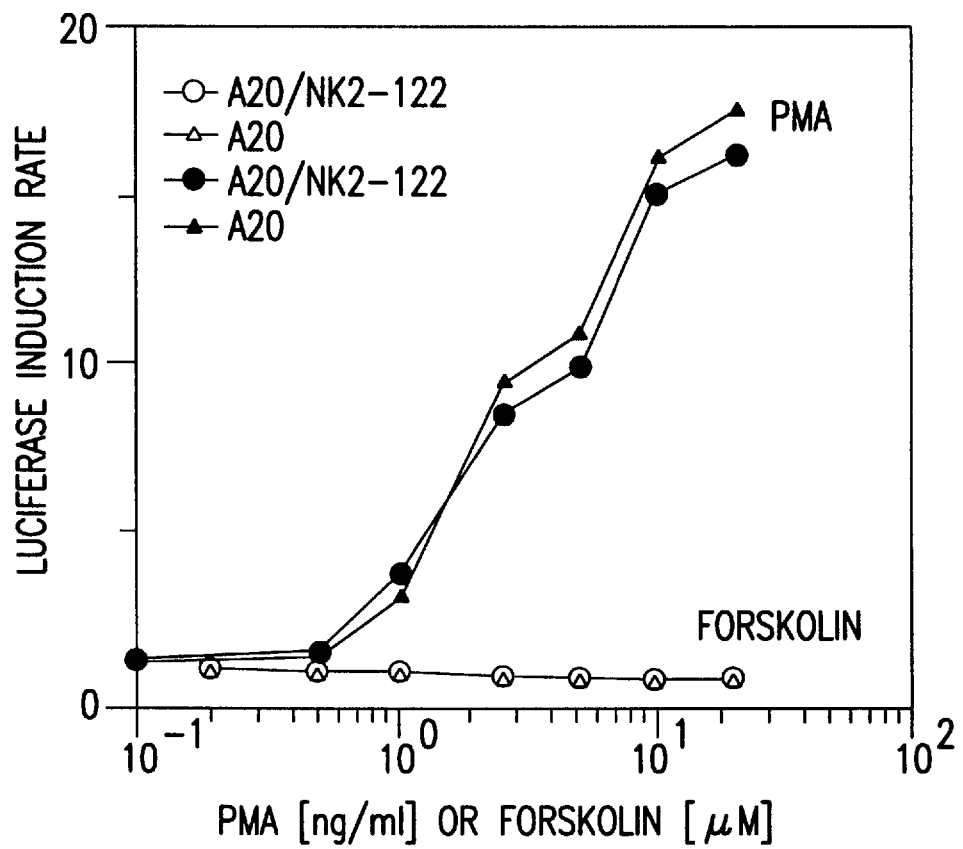
FIG. 27 depicts a graph showing the induction of luciferase expression in the TRE-pretest cell line A20 and in the TRE-test cell line NK2-122 which expresses the human neurokinin2 receptor.

The pretest cell line A20 was transfected, as described under a), by electroporation with the plasmid pAHyg-NK2, which had previously been linearised with BglII. From the day after transfection onwards, the cells were grown in selection medium, as used for the cell line A20 and additionally enriched with 150 μg/ml hygromycin B (Sigma). Individual clones were tested for inducibility of the luciferase activity as described under a). In this case, however, neurokinin A (1 μg, Sigma) was used instead of TPA as the inductor. Clone A20/NK2-122 showed, in repeated experiments a 5–7-fold induction of the luciferase activity after activation of the neurokinin 2-receptor. As shown in FIG. 27, in the pretest cell line A20 and also in the NK2-test cell line A20/NK2-122, the expression of the luciferase is increased only via the IP$_3$/DAG-signal transduction pathway but not by increasing the intracellular cAMP concentration. Whereas in both cell lines the luciferase activity could be induced up to a maximum of 18 times by TPA, depending on the dose, forskolin (the stimulator of adenylate cyclase) did not result in any induction of luciferase activity.

Figure 28:
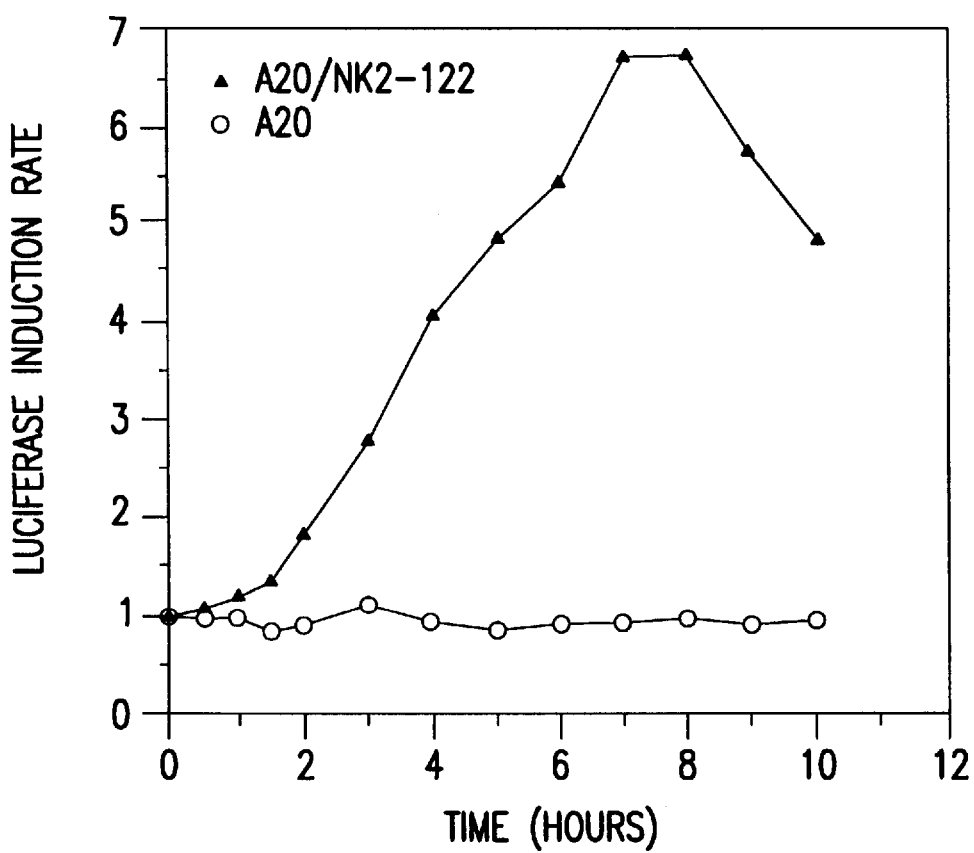
FIG. 28 depicts a graph showing the kinetics of luciferase induction by means of an NK2-specific agonist.

The kinetics of luciferase induction by means of the NK2-specific agonist NKA GR64349 (1 μM, Neosystem S.A.) in the test cell line A20NK2-122 is shown in FIG. 28. The maximum luciferase activation was measured after an induction period of 7–8 hours. In cell line A20, on the other hand, the luciferase activity could not be induced by the addition of the NK2-agonist GR64349. This means that the pretest cell line A20 does not contain any endogenous NK2-receptor molecules and is thus a suitable control cell line for the NK2-test cell line.

Figure 29A:
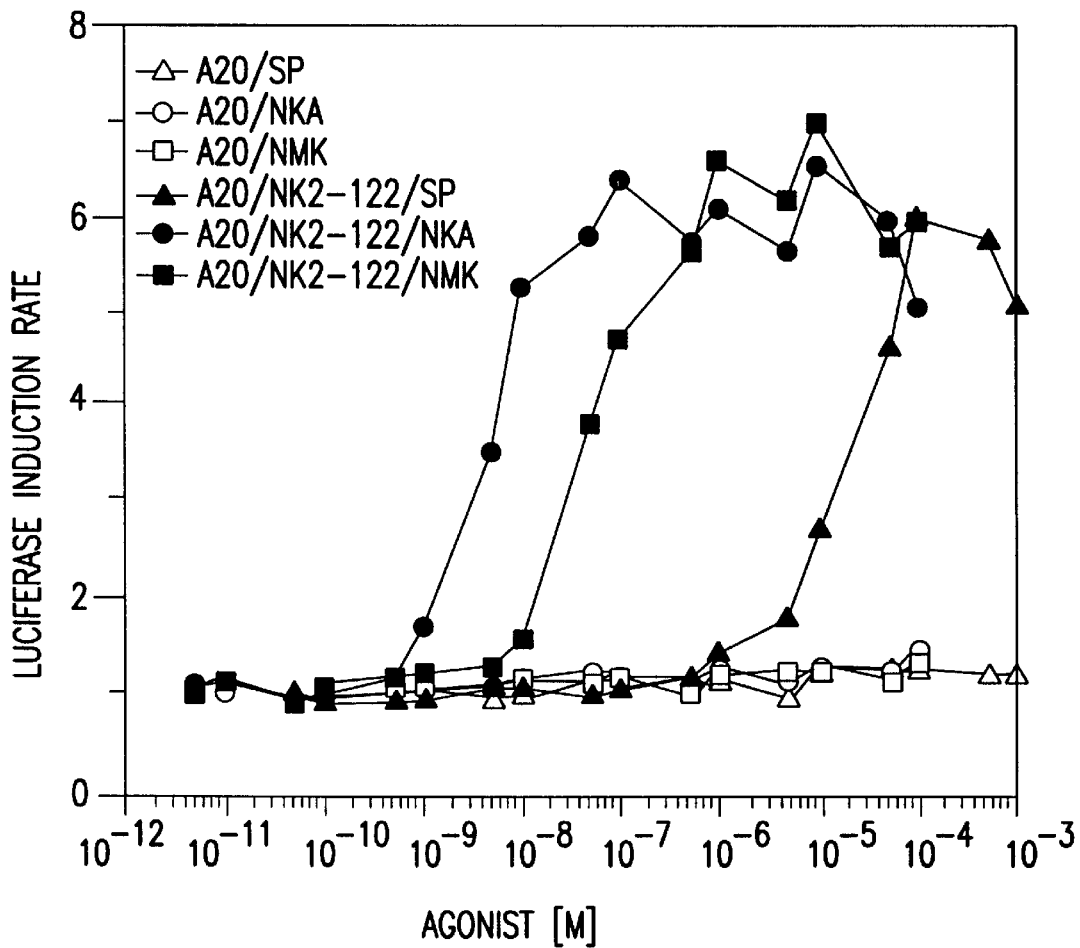
FIG. 29A depicts a graph showing the dosage-activity curves of luciferase activity depending on the activation of the human neurokinin2-receptor by neurokinins.
Figure 29B:
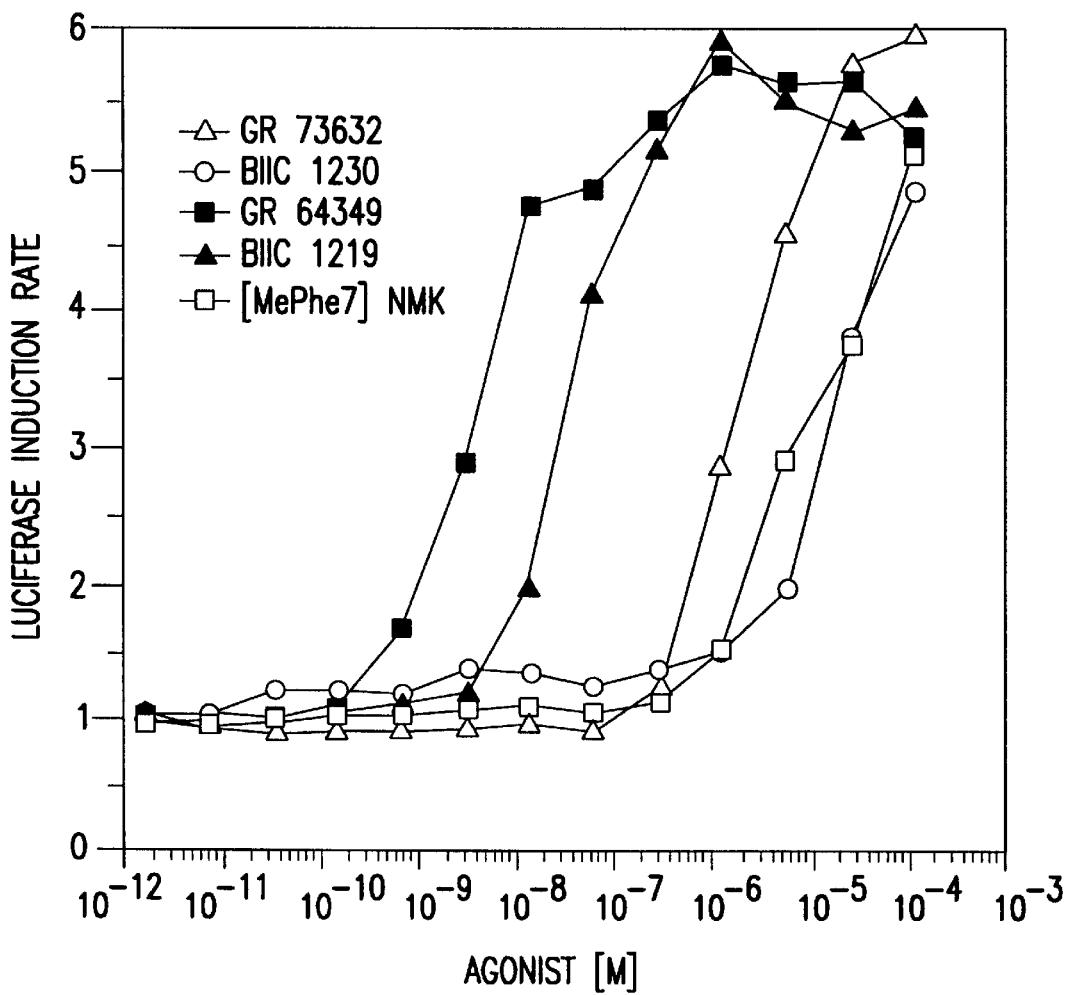
FIG. 29B depicts a graph showing the dosage-activity curve of luciferase activity depending on the activation of human neurokinin2-receptor by agonists for a neurokinin receptor.

FIG. 29A shows the dosage activity curves of luciferase activity as a function of the activation of the human neurokinin 2 receptor by neurokinins. The relative effectiveness of the neurokinins (Sigma), NKA>neuromedin K (NMK) >substance P (SP), in the cell line A20/NK2-122 agrees with data already described in the literature obtained from receptor binding studies. The cell line A20 could not be induced by any of the three tachykinins, which means that it does not contain any of the neurokinin receptors endogenously. The dosage-dependent activity of a series of agonists which are specific for one of the three neurokinin receptors are: NK1: GR73632 (Neosystem S.A.), BIIC 1230 ([β-Ala$^4$, Sar$^9$,Met (O$_2$)$^{11}$]SP(4–11)); NK2: GR64349 (Neosystem S.A.), BIIC 1219 ([β-Ala$^8$ ]NKA(4–10)); NK3: [MePhe$^7$]NMK (Bachem Feinchemikalien AG), is shown in FIG. 29B.

Figure 30:
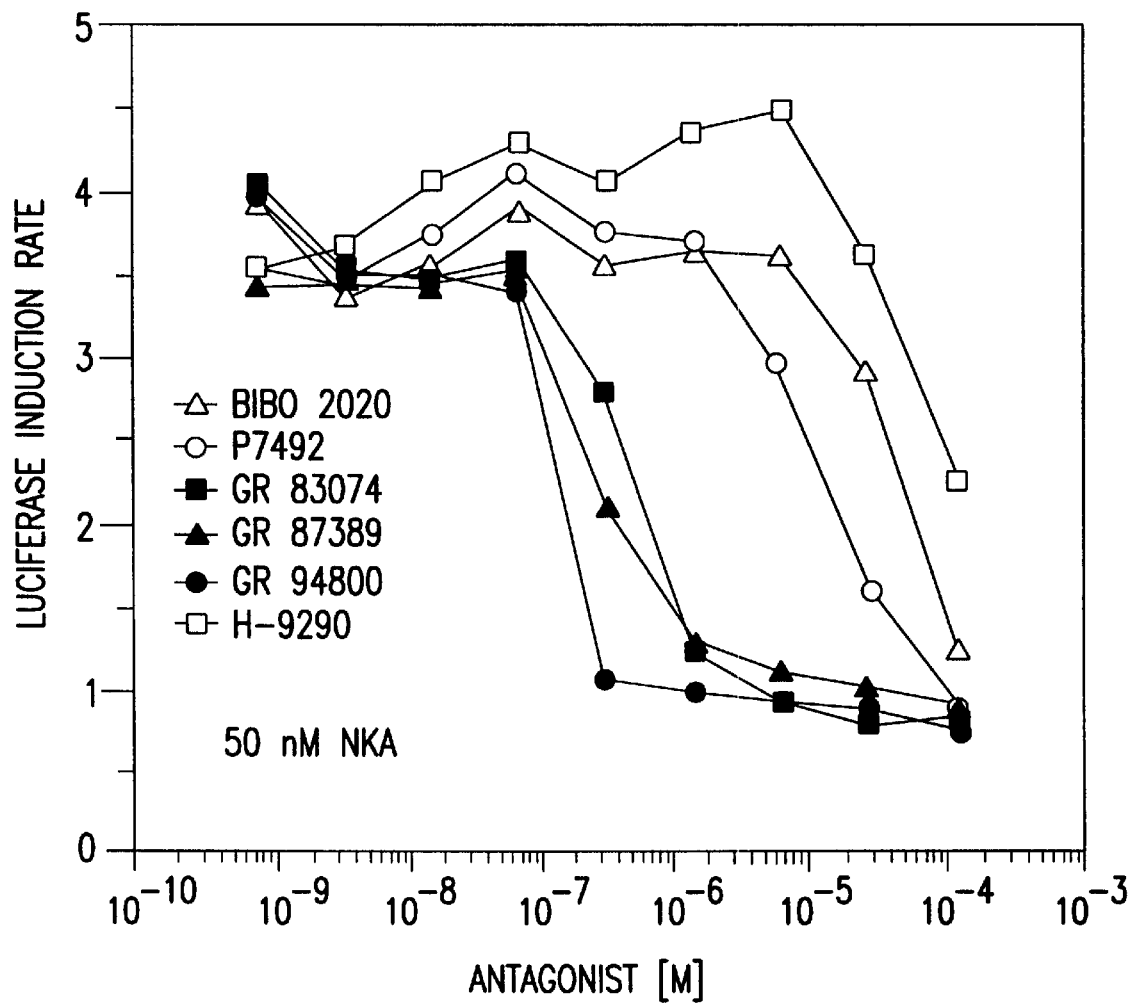
FIG. 30 depicts a graph showing the inhibition of the agonistic activity of neurokinin A by NK2-specific antagonists.

The agonistic effect of neurokinin A in the cell line A20/NK2-122 could be inhibited by the addition of NK2-specific antagonists (GR83074, GR87389, GR94800, Neosystem S.A.) (FIG. 30). For this purpose the cells were simultaneously treated with a constant quantity of neurokinin A (50 nM) and increasing amounts of antagonist. NK1-specific antagonists (i.e. BIBO 2020 (±cis-3-(2-methoxybenzylamino)-2-benzhydrylquinulidine), P7492 (Peninsula Lab.)) or NK3-specific antagonists (H-9290, Bachem Feinchemikalien AG) on the other hand were effective at higher concentrations (P7492>BIBO 2020>H-9290).

c) Development of A549 cell lines which express luciferase as a function of the activation of the human 5HT2-receptor The human 5HT2-receptor is another example of a receptor coupled to the phospholipase C-signal transduction pathway. The TRE-cell line A20 is therefore also suitable in this case as a starting cell line for establishing a test cell line in order to discover substances which modulate the activity of the 5HT2-receptor.

The plasmid pAHyg-5HT2, linearised with BglII, was for this purpose transfected into the cell line A20 by electroporation as described under a) and grown in selection medium. Hygromycin B-resistant cell clones were tested for the inducibility of the luciferase activity after the addition of 5HT2-specific agonist α-methylserotonin maleate (10 μM, Research Biochemicals Inc.), and the clone A20/5HT2-11, in which a 4–5-fold induction was measured, was selected for further experiments.

Figure 31:
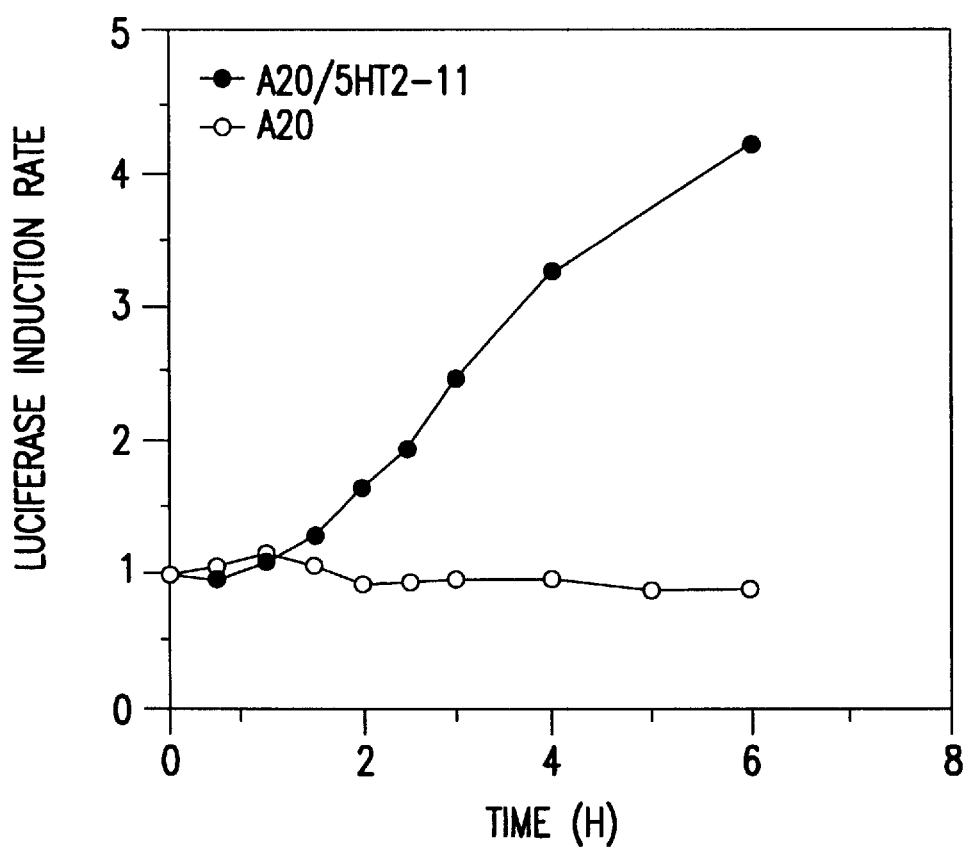
FIG. 31 depicts a graph showing the kinetics of the serotonin-induced luciferase expression in a test cell line which expresses the 5HT2-receptor.

The kinetics of luciferase-induction by means of serotonin (1 μM) in the test cell line A20/5HT2-11 are shown in FIG. 31. As in FIG. 28 the luciferase activity increases continuously up to an induction time of 6 hours. An induction time of 6 to 8 hours is therefore sufficient for testing agonistically or antagonistically acting substances. In cell line A20 the luciferase activity could not be induced by the addition of serotonin. This means that the pretest cell line A20 does not contain any endogenous 5HT2-receptor molecules and is thus a suitable control cell line for the 5HT2-test cell line.

Figure 32A:
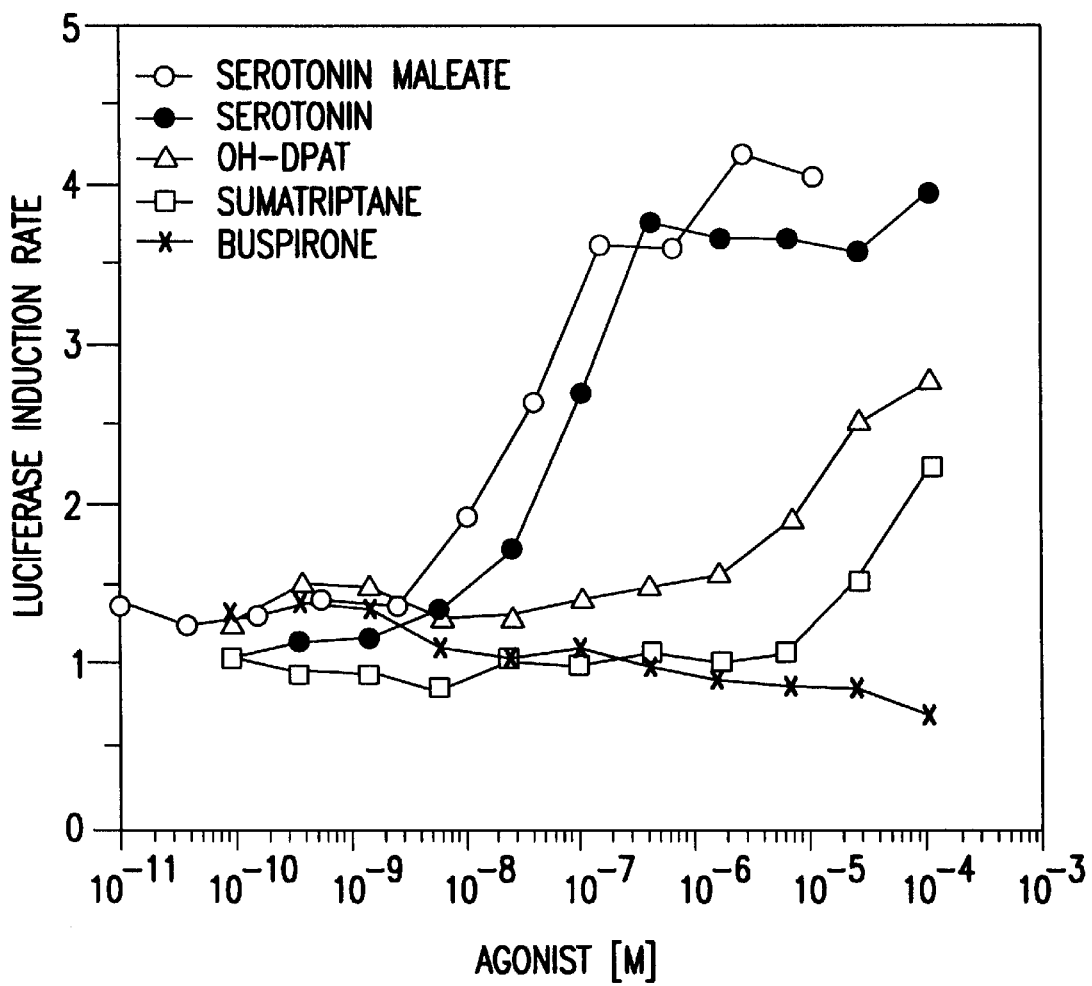
FIGS. 32A and 32B depict dosage-activity curves of luciferase activity as a function of the activation of the human 5HT2-receptor by agonists.

FIG. 32A shows the dose-activity curves of luciferase activity as a function of the activation of the human 5HT2-receptor by agonists. As expected, the dosage-activity curves are selective for serotonin and the 5HT2-receptor agonist serotonin maleate, unlike the 5HT1A-receptor agonist 8OH-DPAT (Research Biochemicals Inc.) and buspirone.

Figure 32B:
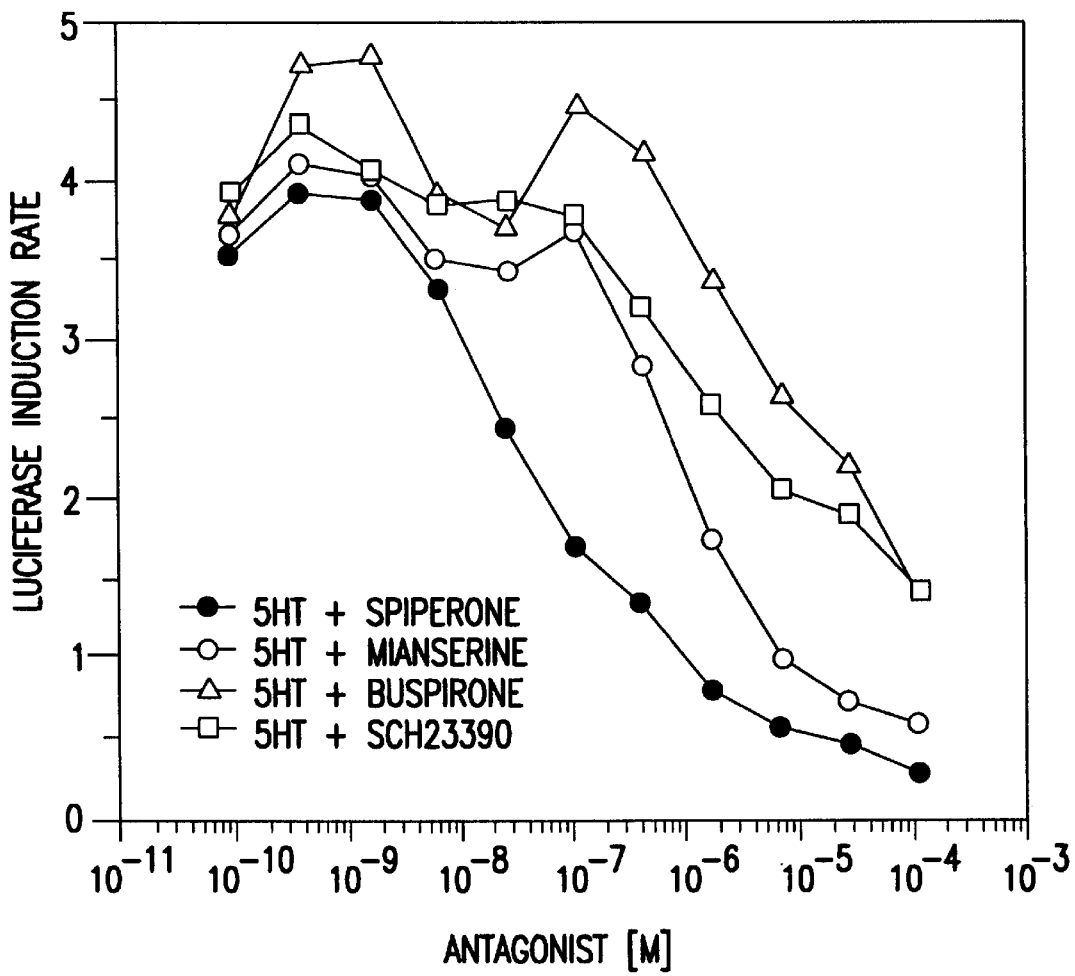

The agonistic activity of serotonin in the cell line A20/5HT2-11 was able to be inhibited by the addition of the 5HT2-specific antagonists spiperone and mianserine (Research Biochemicals Inc.) (FIG. 32B). For this purpose the cells were simultaneously treated with a constant amount of serotonin (1 µg) and increasing amounts of antagonist.

Example 7 a) Development of recombinant Chinese hamster ovary (CHO) cell lines which express luciferase as a function of the intracellular cAMP-concentration (CRE-cell lines)

In order to prepare (pre)-test cells for investigating substances which influence the intracellular cAMP level directly or indirectly by interacting with receptor molecules, the Chinese hamster ovary cell line CHO-DXB11 (Urlaub and Chasin, 1980) was transfected with the sensor DNA pADneo2-C6-BGL.

The parental cell line CHO-DXB11 was calculated in Roswell Park Memorial Institute (RPMI) medium 1640 (Gibco), supplemented with 10% foetal calves' serum (Sebak), hypoxanthine (100 µM), thymidine (16 µM), sodium penicillin G (100 units/ml) and streptomycin (50 units/ml). One day before transfection the cells were placed in fresh medium.

The transfection by electroporation was carried out as follows: after removal of the medium the cells were detached from the surface by means of a trypsin/PBS solution, suspended in medium and pelleted for 5 minutes at 250×g. The cells were washed in HBS (10 mM HEPES pH 7.4, 150 mM NaCl) and pelleted by centrifuging. The cells were suspended in HBS in a density of $1 \times 10^7$ cells/ml. 0.8 ml of cell suspension were mixed with 20 µg of DNA of the plasmid pADneo2-C6-BGL linearised with ScaI and transferred into an electroporation dish. The transfection was carried out using the PG200 Progenetor II Electroporation apparatus (Hoefer Scientific Instruments, San Francisco, Calif.) with a single current impulse of 320 V, 1080 µF, 1000 msec. After the electroporation the cells were diluted in the medium mentioned above, 20,000 cells per 90 mm culture dish was sown and incubated overnight at 37° C. From the day after transfection onwards, the cells were cultivated with selection medium (RPMI 1640 medium supplemented with 10% foetal calves' serum, hypoxanthine (100 µM), thymidine (16 µM), sodium penicillin G (100 units/ml), and streptomycin (50 units/ml), 700 µg/ml of geneticin (G-418, Gibco-BRL) and thereafter inspected visually for cell growth.

7 to 10 days after transfection, individual cell clones which had formed were transferred into cell culture dishes with 24 wells and cultivation was continued. 25 isolated G-418 resistant cell clones were tested for the inducibility of luciferase expression by activation of the adenylate cyclase.

Approximately 300,000 cells of each clone were sown four-fold in each well of a 6-well cell culture plate and incubated 24 hours at 37° C. Two batches of each were treated with 20 µM forskolin and incubated for a further 5 hours at 37° C. Then the medium was removed from all the cells and the cells were washed with PBS. The cells were lysed with 1% Triton X-100 and the luciferase activity was determined in a Berthold Lumat LB9501 luminometer (Brasier et al., 1989). Cell clone C6-13 was selected for further experiments because it had the highest base level of luciferase activity whilst at the same time a very high inducibility by forskolin.

Figure 33:
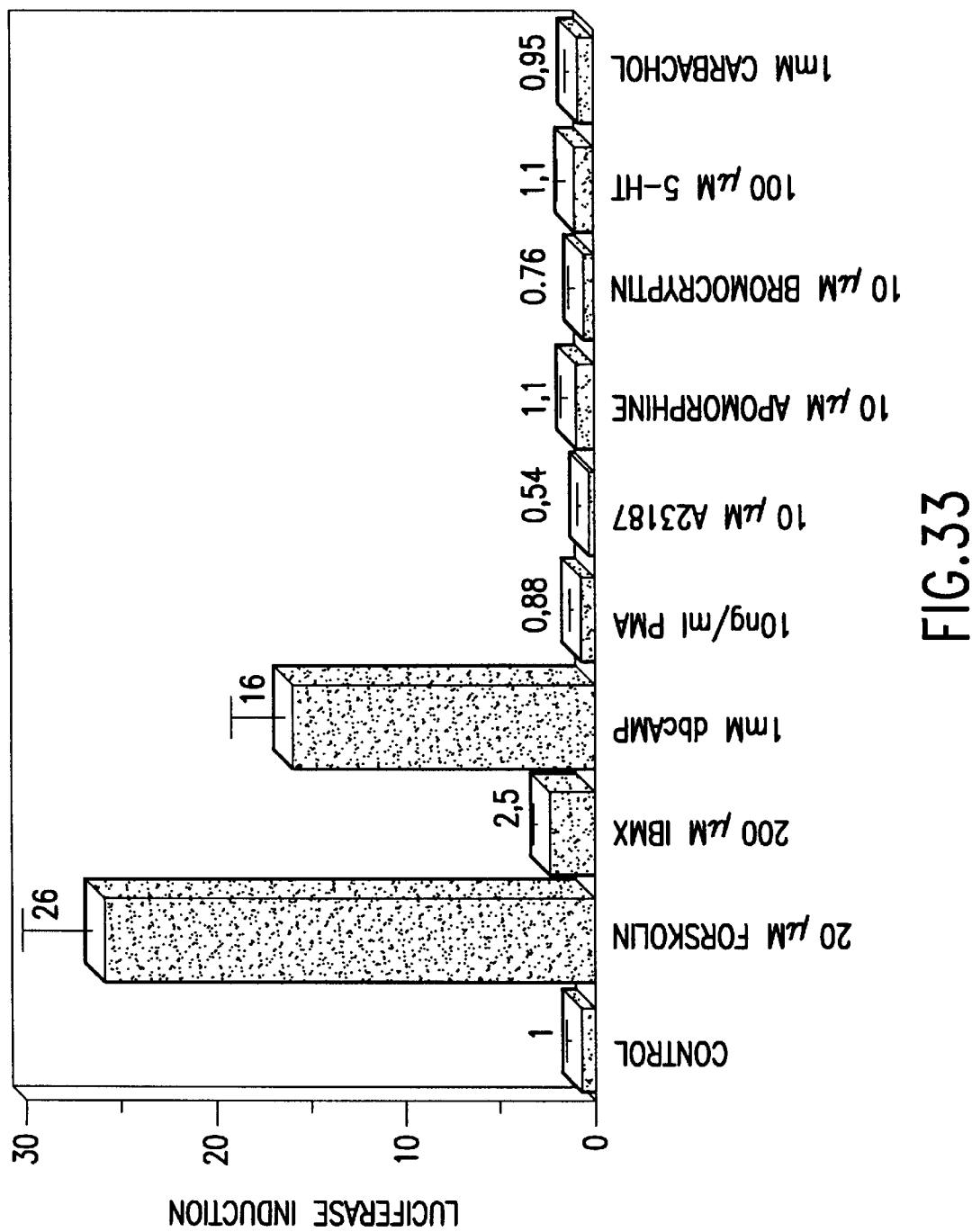
FIG. 33 depicts a bar graph showing the treatment of CRE-pretest cells (CHO-cells, stably transformed with pADneo2-C6-BGL) with various substances which alter the cAMP- or $IP_3$/DAG-concentration or simulate a change in concentration, or with receptor-specific agonists.

Cells of the cell line CHO C6-13 were treated for 3 hours with various substances which alter the intracellular concentration of cAMP or IP$_3$/DAG or simulate a change in concentration, and also treated with receptor-specific agonists which influence the above-mentioned signal transduction mechanisms. As shown in FIG. 33, in the cell line CHO C6-13 the expression of the luciferase was increased only by cAMP-increasing substances such as forskolin (stimulator of adenylate cyclase) dibutyryl-cAMP (membrane-permeable cAMP-derivative and isobutylmethylxanthine (IBMX, phosphordiesterase-inhibitor). Phorbolester PMA, $Ca^{2+}$-ionophor A23187 and agonistic compounds for dopamine receptors (apomorphine, bromocryptin), muscarinic acetylcholine receptors (carbachol) and serotonin did not bring about any significant change in the luciferase activity. This means that the luciferase expression in the cell line CHO C6-13 is modulated only by the change in the cAMP-concentration but not by the change in the IP$_3$/DAG-concentration, and furthermore that the cells do not contain any biologically detectable cAMP stimulating receptors of the dopaminergic, muscarinic or serotonin type.

Figure 34:
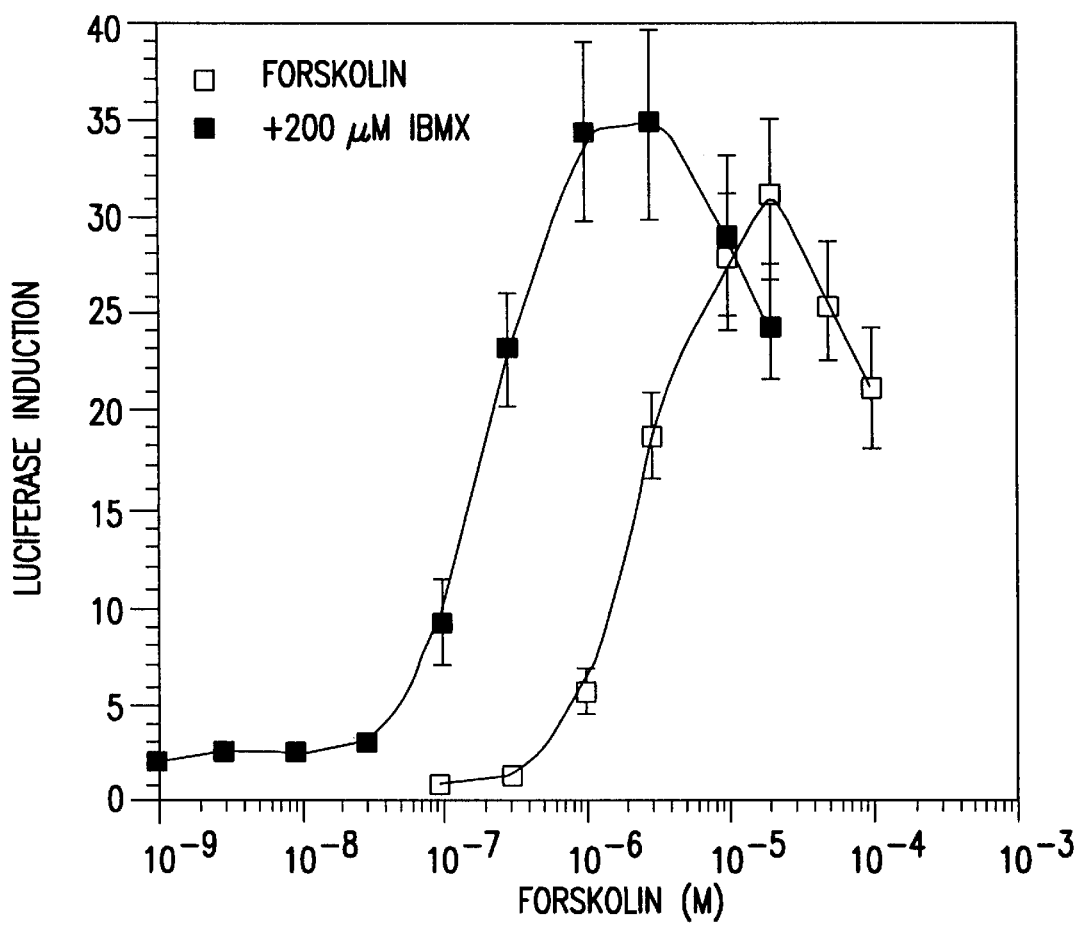
FIG. 34 depicts a dosage activity curve of the transcription of activation of the luciferase gene in CRE-pretest cells by forskolin.

The dosage-activity curve of the transcriptional activation of the luciferase reporter gene by forskolin-induced increase in the cAMP-concentration, as shown in FIG. 34, yields maximum induction at 20 µM forskolin. The drop in luciferase induction at even higher concentrations of forskolin would appear to be due to toxic effects of the forskolin itself or the excessively high CAMP level. Inhibition of phosphodiesterase by IBMX results in a reduced breakdown of the cAMP formed and consequently increased cAMP levels, with simultaneous activation of the adenylate cyclase. The maximum induction of the luciferase reporter gene was not significantly influenced by IBMX treatment, which means that the maximum activation of transcription is achieved at a cAMP concentration, obtained by 20 µM forskolin. The shift in the dosage-activity curve with IBMX by one order of magnitude to lower forskolin concentrations clearly demonstrates the accumulation of cAMP by inhibiting the enzyme responsible for its breakdown.

Figure 35A:
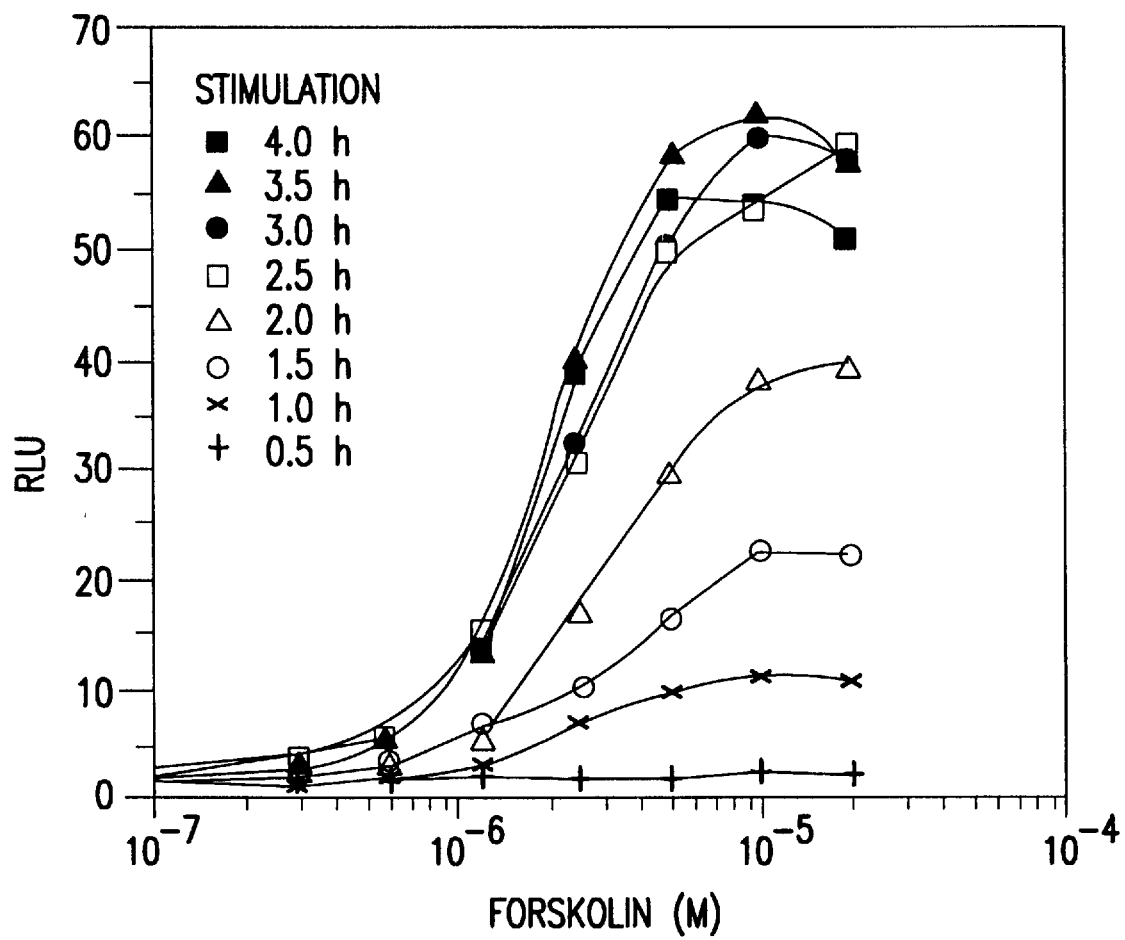
FIG. 35A depicts a graph showing the kinetics of luciferase induction in CHO-cells as a function of the dosage of forskolin.
Figure 35B:
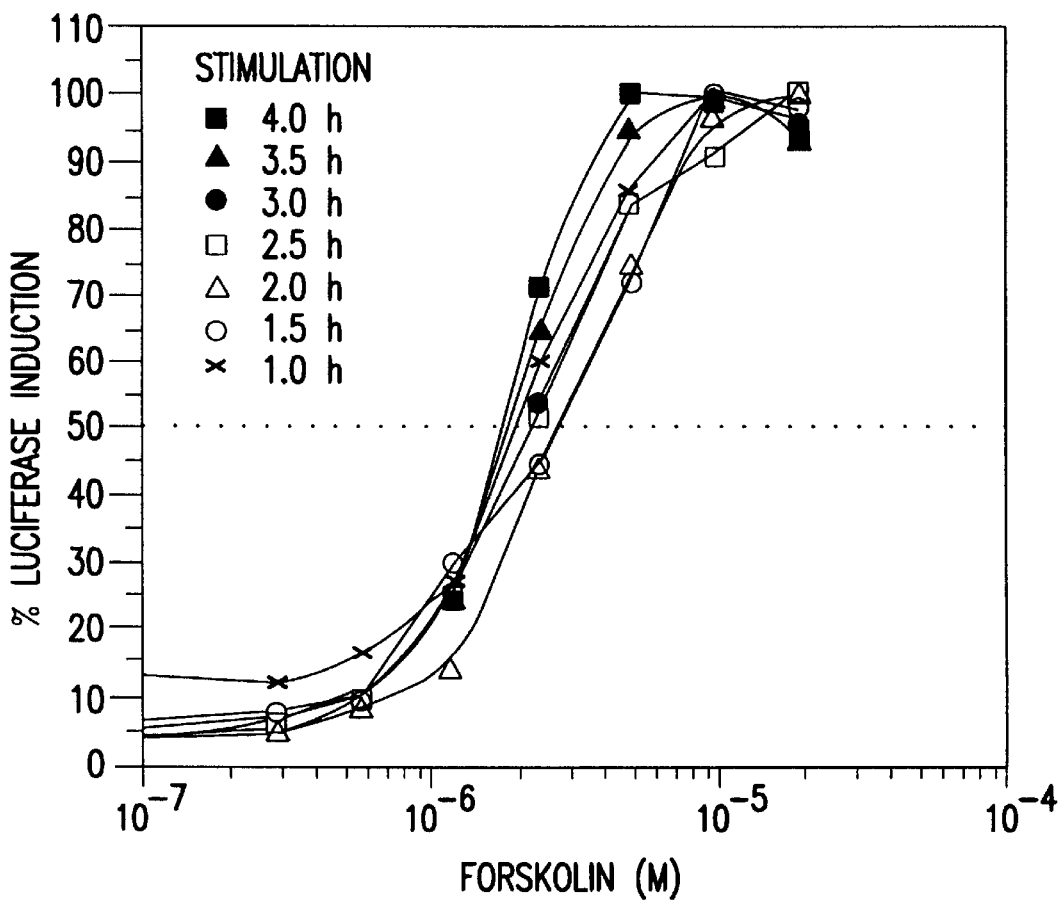
FIG. 35B a graph showing the kinetics of the luciferase induction in CHO-cells as a function of the dosage of forskolin ($ED_{50}$ measurement).

The kinetics of luciferase-induction as a function of the dosage of forskolin, shown in FIG. 35A, showed that 60 minutes after stimulation with forskolin an increased luciferase activity can be detected. Total induction of the luciferase expression is achieved after 2.5 hours and does not change up to 4 hours after forskolin stimulation. Although the absolute level of luciferase induction increases up to 2.5 hours, the ED$_{50}$ levels remain virtually unaffected by the duration of the forskolin treatment (FIG. 35B).

b) Development of recombinant CHO-test cell lines which express luciferase as a function of the activation of the human dopamine-D1-receptor This Example, like the following Example 8, demonstrates the preparation of (control) CRE-test cells which are also suitable for a cellular screening system for substances which modulate specific, preferably human adenylate cyclase-coupled receptors. The human dopamine D1-receptor sequence was used to produce receptor DNA.

The cell line CHO C6-13 characterised above was transfected, as described under a), by electroporation with plasmid pAD-CMV2:D1, which had previously been linearised with FspI. From the day after transfection onwards the cells were cultivated in selection medium for the selection according to dihydrofolate reductase (DHFR) (nucleotide-free medium α-MEM (Gibco)), 10% dialysed foetal calves' serum (Sebak), sodium penicillin G (100 units/ml), and streptomycin (50 units/ml), 700 µg/ml geneticin (G-418, Gibco-BRL) and thereafter visually inspected for cell growth. 24 individual isolated cell clones were grown in 6-well cell culture dishes as described above and 4 hours after treatment with 10 µM apomorphine (agonist for the dopamine receptor) they were tested for the increase in luciferase activity compared with untreated cells. Clone CHO 13D1-38 showed, in repeated experiments, the highest increase in luciferase activity after activation of the dopamine D1-receptor.

Figure 36:
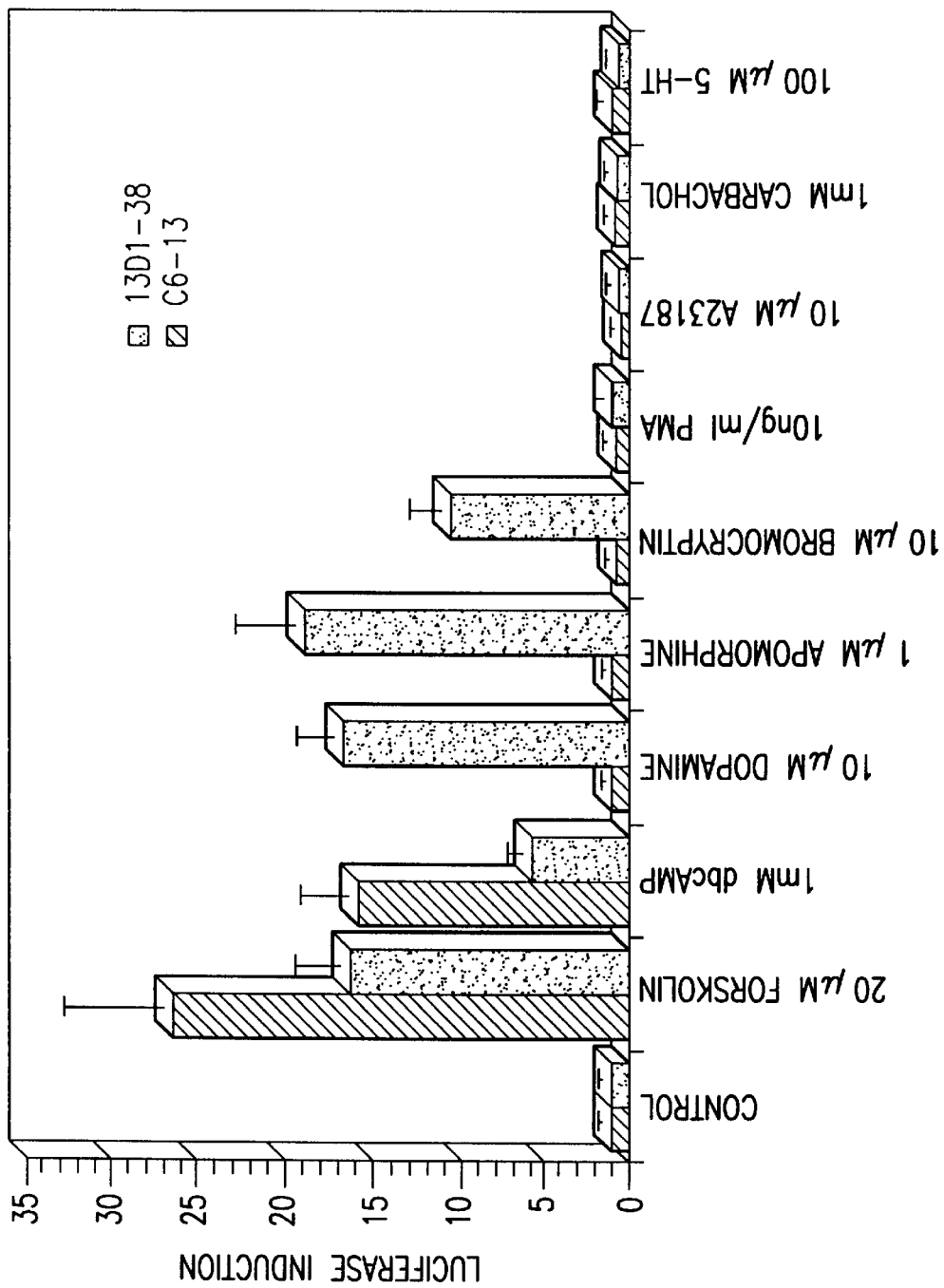
FIG. 36 depicts a bar graph showing the treatment of CHO-pretest and test cells, stably transformed with CRE-sensor-DNA and with dopamine-D1-receptor DNA, with various substances.

For the use of test cell lines in an automatic screening system with a high throughput rate it is advantageous to use microtitre plates having 96 wells per plate. For this purpose, 60,000 cells (CHO C6-13 or CHO 13D1-38) were sown in 200 µl medium per well in light-impermeable microtitre plates coated with tissue culture (Microlite™, Dynatech Labroatories) and incubated overnight at 37° C. Then various chemicals were added to the cells and they were incubated for a certain length of time (usually 3 hours). After removal of the medium the cells were washed with PBS, lysed in 1% Triton X-100 and the luciferase activity was measured in a 96-well luminometer (ML-1000, Dynatech) (FIG. 36).

Figure 37A:
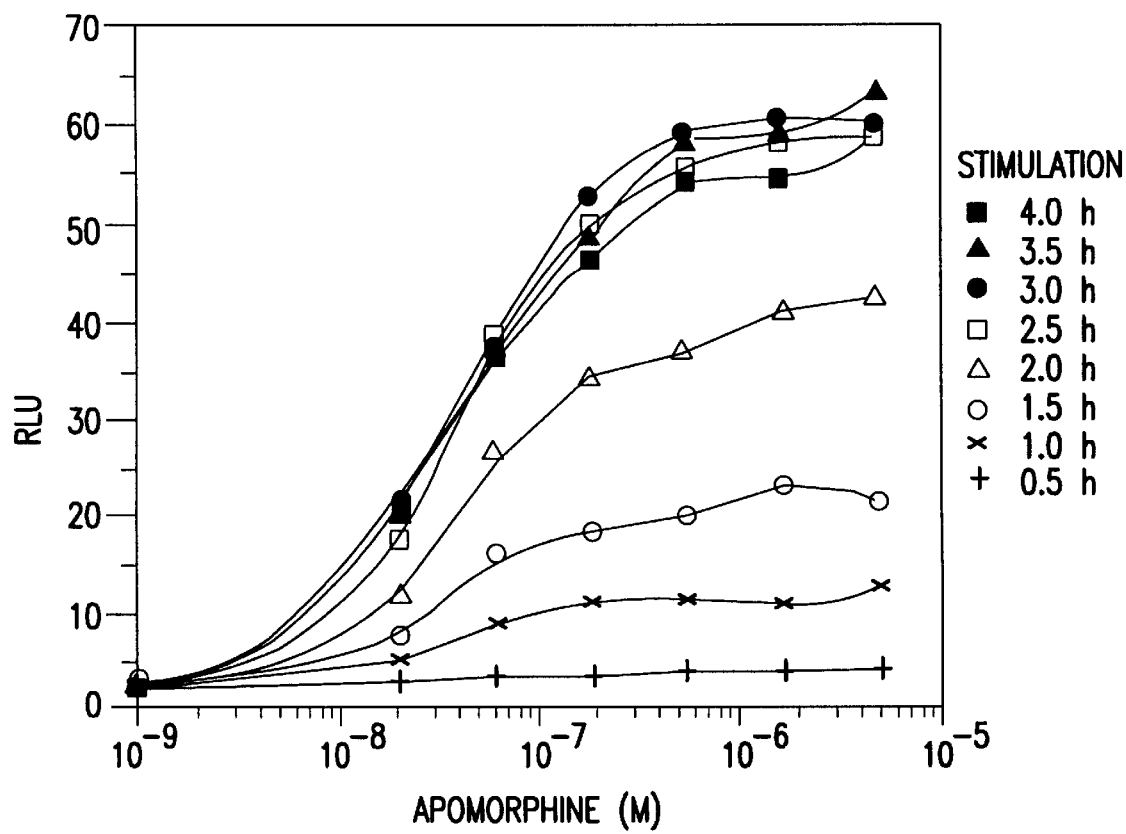
Figure 37B:
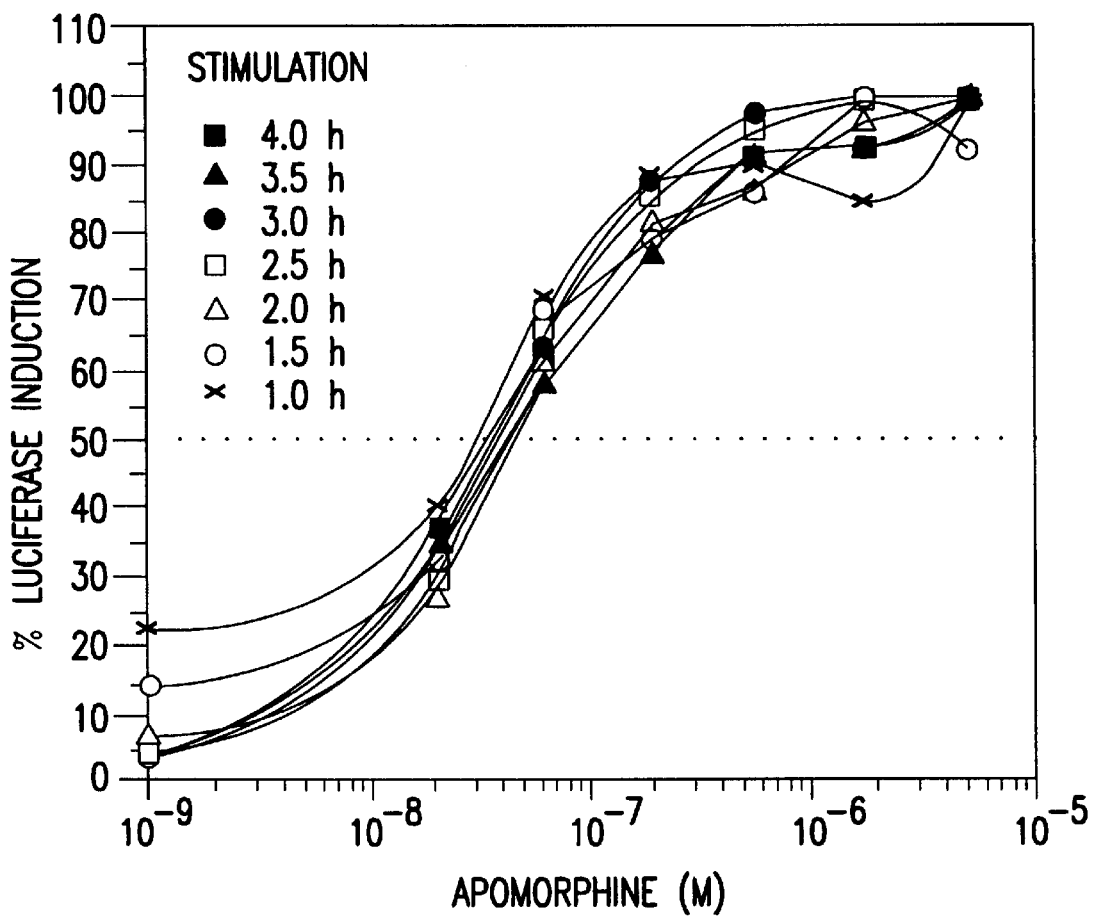
Figure 38A:
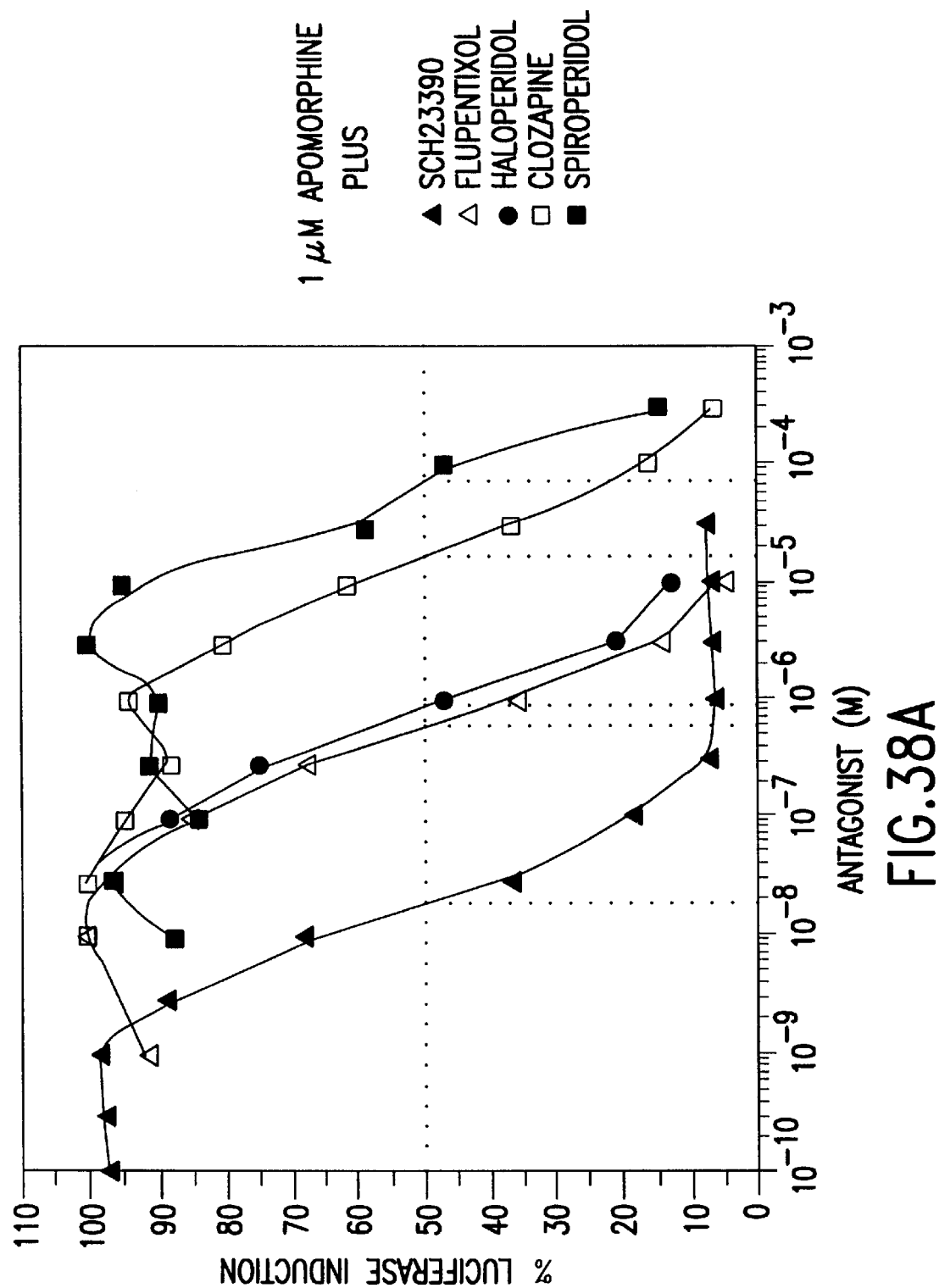

The dosage activity curves of the luciferase activity as a function of the activation of the human dopamine D1-receptor, shown in FIGS. 37A and 37B and in FIGS. 38A and 38B, were plotted in the microtitre plate format and represent for each dot on the curve the average of 4 separate measurements; the standard deviation was about 15%.

Analogously to the kinetics of luciferase-induction by means of forskolin in the pretest cell line CHO C6-13 (Example 7 a)) increased luciferase activity was measured in the dopamine D1-receptor test cell line CHO 13D1-38 one hour after stimulation of the D1-receptor with apomorphine (FIG. 37A). The maximum luciferase activation was achieved after 2.5 hours stimulation and remained constant for up to 4 hours. The comparison with the kinetics after direct activation of the adenylate cyclase using forskolin (FIG. 35A) leads one to conclude that the step which determines the speed is the transcription and translation of the luciferase reporter gene, but not the stimulation of the adenylate cyclase by the activated receptor.

The amended recording of the measurements for determining the $ED_{50}$ values of apomorphine in FIG. 37B showed no significant dependency of the $ED_{50}$ values on the duration of receptor stimulation with the agonist.

FIG. 38A shows that the induction of the reporter gene by the activation of the D1-receptor with an agonist (Apomorphine) could be prevented in dosage-dependent manner with antagonists. For this purpose the test cells were mixed with the antagonist 24 hours after being sown in the microtitre plates and immediately afterwards a constant quantity of apomorphine (1 µM final concentration) was added, which as shown in FIG. 37A brings about maximum induction of the luciferase reporter gene. In order to simulate a screening process in which the test substances are preferably supplied in a uniform solvent, a final concentration of 1% DMSO was used in this experiment.

The effectiveness of the substances used in this test procedure correlates well with the data described in the literature by means of receptor binding studies.

FIG. 38B shows the same values recorded in another form (x-fold induction of the luciferase compared with identical untreated cells as control) and additionally the dosage-dependent activity of the agonist bromocryptin. The reversal of luciferase induction at the highest concentration of bromocryptin (100 µM) can be attributed to the cell toxicity of bromocryptin itself or to the low pH which was necessary to dissolve the bromocryptin.

Example 8 a) Development of recombinant Chinese hamster ovary (CHO) cell lines which express luciferase as a function of the intracellular cAMP-concentration (CRE-cell lines)

For the preparation of (pre)-test cells for testing substances which affect the intracellular cAMP level directly or indirectly by interaction with receptor molecules, the Chinese hamster ovary cell line CHO-DXB11 (Urlaub and Chasin, 1980) was transfected with sensor DNA pADneo2-C12-TKL. (This plasmid differs from the pADneo2-C6-BGL described in Example 1) in that the section containing the 6 CRE-elements is duplicated and the β-globin promotor is replaced by the TK-promotor (see Example 1 b)). In order to do this the SalI-HindIII-β-globin-promotor-fragment was replaced by a similarly cut fragment containing the TK-promotor (McKnight, 1980)).

The parental cell line CHO-DXB11 was cultivated in Roswell Park Memorial Institute (RPMI) medium 1640 (Gibco) supplemented with 10% foetal calves' serum (Sebak), hypoxanthine (100 µM), thymidine (16 µM), sodium penicillin G (100 units/ml), and streptomycin (50 units/ml). One day before transfection the cells were placed in fresh medium.

The transfection and testing of the cell clones were carried out as in Example 7 a). Cell clone C12-32 was selected for further experiments as it showed the highest base level of luciferase activity whilst at the same time having very high inducibility by forskolin.

b) Development of recombinant CHO-test cell lines which express luciferase as a function of the activation of the human dopamine D5-receptor This Example (like the preceding Example 7) demonstrates the preparation of (control) CRE-test cells which are also suitable for a cellular screening system for substances which modulate specific, preferably human adenylate cyclase-coupled receptors. The human dopamine-D5-receptor sequence was used to prepare receptor DNA.

The cell line CHO C12-32 characterised earlier was transfected as described under a) by electroporation with plasmid pAD-CMV1:D5 which had previously been linearised with 20 µg StuI. (The plasmid pAD-CMV1:D5 was prepared by ligating the 1.6 kb SalI-XbaI-fragment of phD5-gem, which contains the coding region of human D5-receptor gene (Grandy et al., 1991), into the human vector pAD-CMV1 which has also been cut.) From the day after transfection onwards the cells were cultivated in selection medium for the selection according to dihydrofolate reductase (DNFR) (nucleotide-free medium α-MEM (Gibco), 10% dialysed foetal calves' serum (Sebak), sodium penicillin G (100 units/ml), and streptomycin (50 units/ml), 700 µg/ml geneticin (G-418, Gibco-BRL) and thereafter visually inspected for cell growth. 24 individual isolated cell clones were grown in 6-well cell culture dishes as described above and 4 hours after treatment with 10 µM apomorphine (agonist for the dopamine receptor) they were investigated for any increase in luciferase activity compared with untreated cells. In repeated experiments, clone CHO 32D5-39 showed the highest increase in luciferase activity after activation of the dopamine D5-receptor.

Figure 39A:
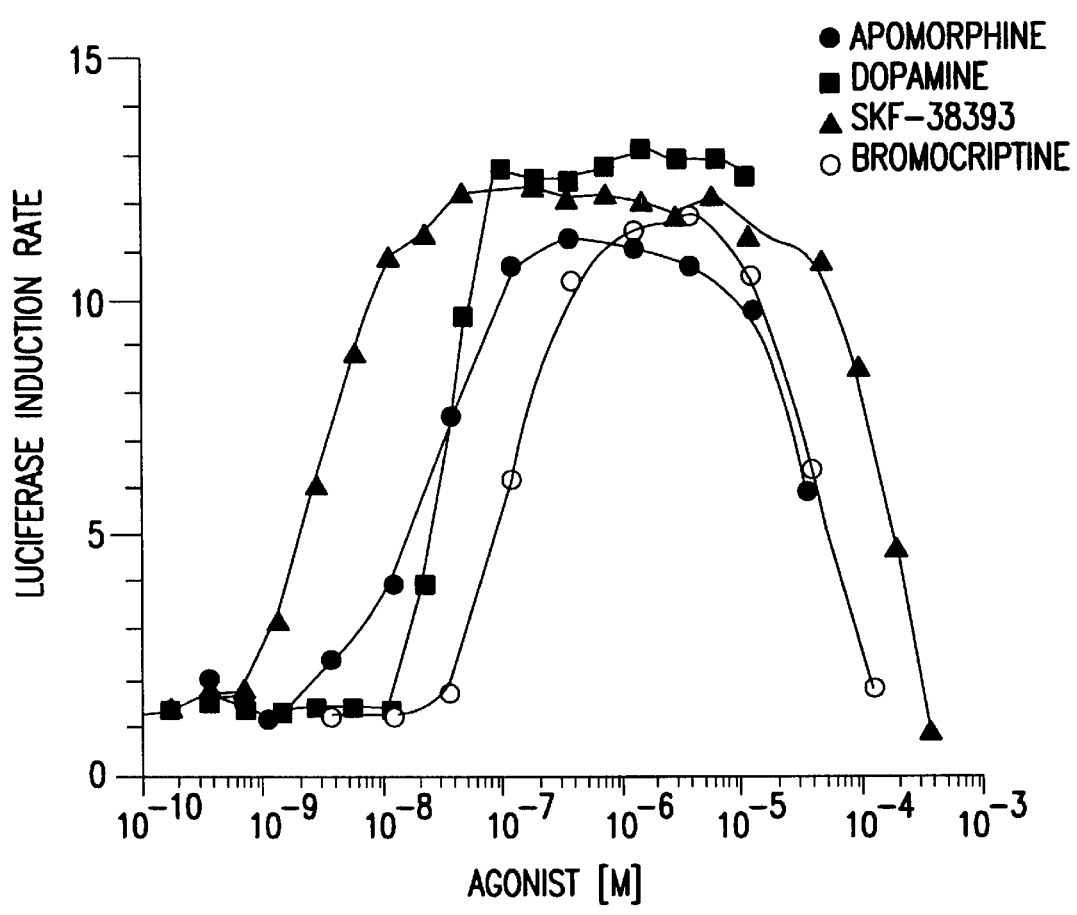
FIGS. 39A and 39B depict dosage activity curves of luciferase activity as a function of the activation of the dopamine-D5-receptor.
Figure 39B:
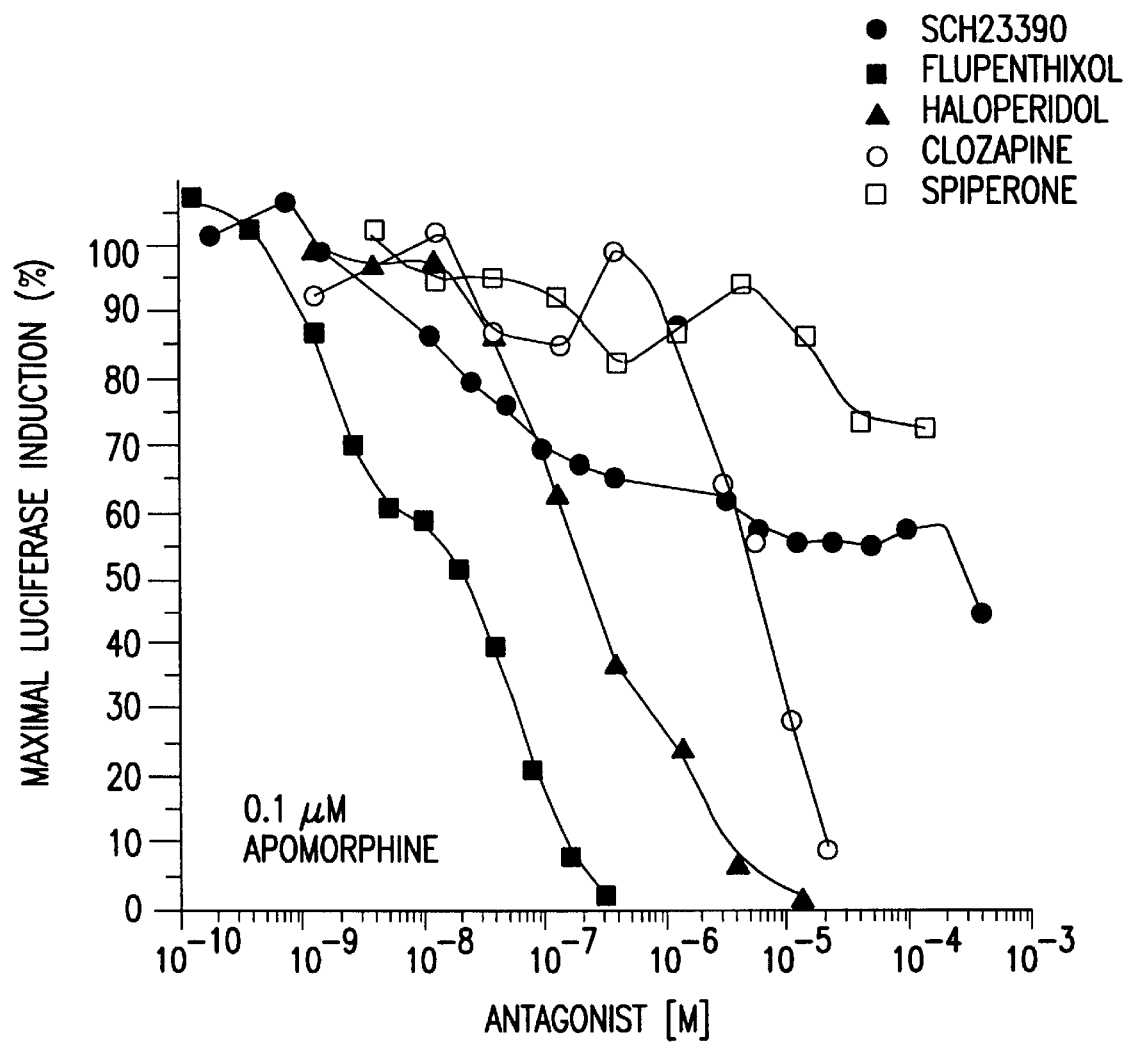

FIG. 39A shows that the induction of the reporter gene by the activation of the D5-receptor with an agonist (apomorphine) could be prevented by means of antagonists, in dosage-dependent manner. To do this, the test cells were mixed with the antagonist 24 hours after sewing in the microtitre plates and immediately afterwards a constant quantity of apomorphine (0.1 µM final concentration) was added, which brings about maximum induction of the luciferase reporter gene, as shown in FIG. 39A. The results of these experiments are shown in FIG. 39B.

The efficacy of the substances used in this test procedure correlates well with the data described in the literature by means of receptor binding studies.

Example 9

Development of a reagent for measuring the luciferase activity

The effect of varying the concentration of ATP, luciferin, $MgSO_4 \cdot 7H_2O$, dithiothreitol (DDT), β-mercaptoethanol (BME), sodium tripolyphosphate (NaTPP), Triton X-100 and the pH on the luciferase measuring signal obtained was determined (Table 2). The remaining components were present in the concentrations corresponding to the preferred basic buffer shown in Table 1. The measurements obtained 3 minutes after the addition of the reagent were used for comparison (given as percentage of the maximum measuring signal obtained).

Figure 40:
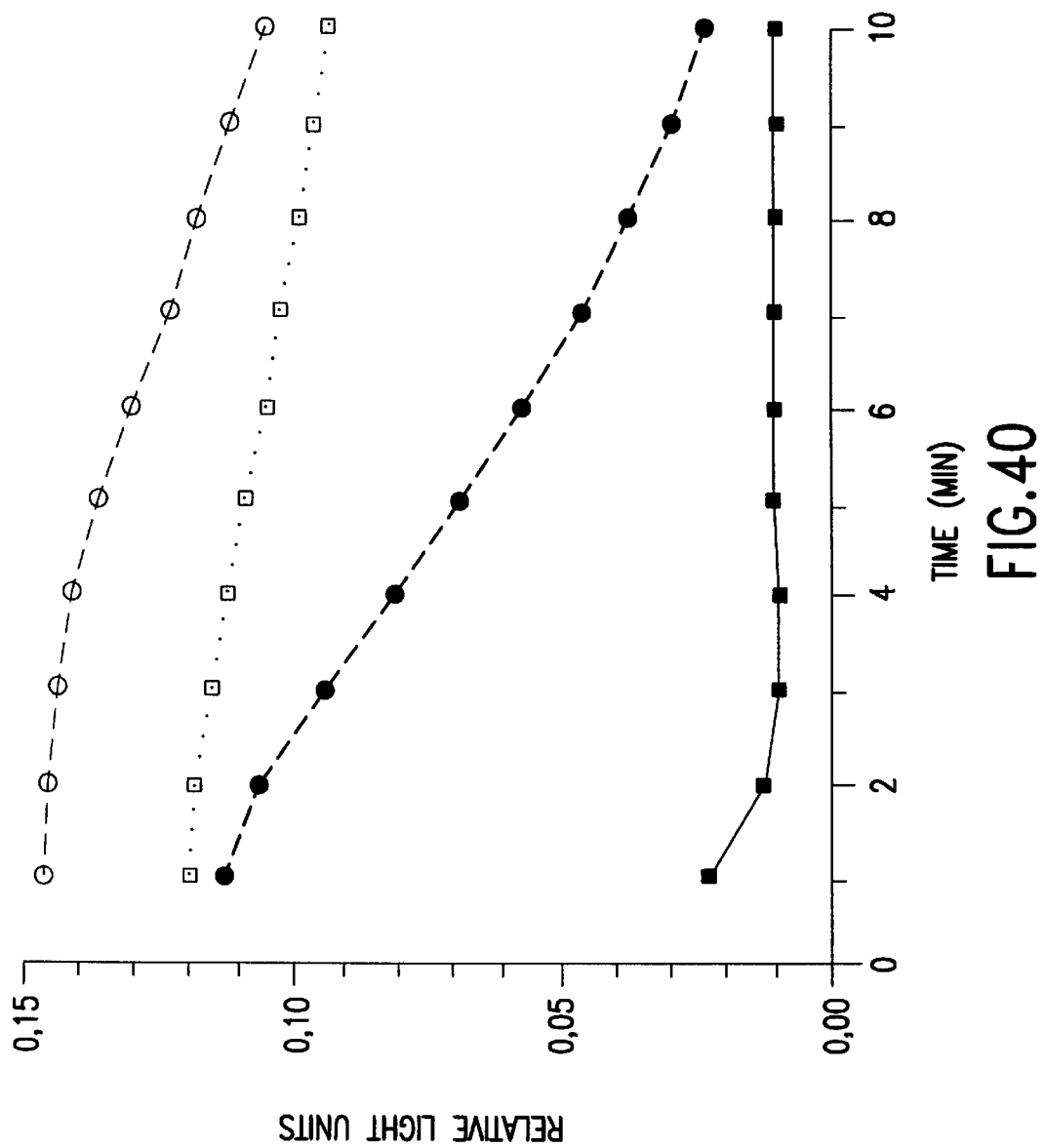
FIG. 40 depicts a curve showing the perfecting of a reagent for measuring luciferase activity.

FIG. 40 shows the effect of adding β-mercaptoethanol and/or sodium tripolyphosphate to the basic buffer on the luciferase measuring signal (filled-in squares: basic buffer; open squares: addition of 4 μl/ml β-mercaptoethanol; closed circles: addition of 0.2 mg/ml sodium tripolyphosphate; open circles: addition of 4 μl/ml β-mercaptoethanol plus 0.2 mg/ml sodium tripolyphosphate). A luminometer bearing the name Microlite ML1000 made by Dynatech was used for all the experiments.

TABLE 1

| Substance | nmol/l | MW | g/l |
|---|---|---|---|
| Tricin* | 25 | 179 | 4.48 |
| EDTA | 0.5 | 372 | 0.186 |
| MgSO$_4$.7H$_2$O | 16.3 | 246 | 4.0 |
| ATP | 1.2 | 605 | 0.726 |
| Luciferin, sodium salt | 0.05 | 302 | 0.015 |
| DTT | 6.5 | 154 | 1.0 |
| NaTTP | 0.54 | 368 | 0.2 |

*N-tris-(hydroxymethyl)methyl-glycine
Triton X-100: 1 ml/l. The pH is adjusted to 7.8 with 1N NaOH.

| ATP-Conc (g/l) | 3.30 | 1.47 | 0.65 | 0.29 | 0.13 | 0.06 | | |
|---|---|---|---|---|---|---|---|---|
| % max. signal | 78 | 83 | 98 | 100 | 95 | 61 | | |
| Lucifenn-Conc (mg/l) | 15.0 | 10.0 | 6.67 | 4.44 | 2.96 | 1.98 | 1.32 | 0.88 |
| % max. signal | 100 | 95 | 88 | 75 | 65 | 58 | 42 | |
| MgSO$_4$-conc. (g/l) | 4.00 | 2.67 | 1.78 | 1.19 | 0.79 | 0.53 | 0.35 | 0.23 |
| % max. signal | 100 | 100 | 77 | 77 | 64 | 48 | 20 | |
| DTT-Conc (g/l) | 5.0 | 4.0 | 3.0 | 2.0 | 1.0 | 0.0 | | |
| % max. signal | 71 | 89 | 95 | 97 | 100 | 91 | | |
| BME-conc. (ml/l) | 10.0 | 6.67 | 4.44 | 2.96 | 1.98 | 1.32 | 0.88 | 0.59 |
| max. signal | 93 | 94 | 100 | 86 | 84 | 68 | 82 | 80 |
| NaTPP-conc.(mg/1) | 500 | 158 | 50.0 | 15.8 | 5.01 | 0.0 | | |
| % max. signal | 75 | 100 | | 82 | 64 | 54 | 49 | |
| Triton-X100 (%) | 0.30 | 0.20 | 0.13 | 0.09 | 0.06 | 0.04 | 0.03 | 0.02 |
| % max. signal | 82 | 88 | 92 | 100 | 99 | 97 | 87 | 28 |
| pH | 7.0 | 7.2 | 7.4 | 7.6 | 7.8 | 8.0 | 8.2 | 8.4 |
| % max. signal | 63 | 79 | 92 | 91 | 100 | 88 | 59 | 65 |

Bibliography:
Angel, P., Baumann, I., Stein, B., Delius, H., Rahmsdorf, H. J. und Herrlich, P., 1987a, Mol. Cell. Biol. 7, 2256–2266
Angel, P., Imagawa, M., Chiu, R., Stein, B., Imbra, R. J., Rahmsdorf, H. J., Jonat, L., Herrlich, P. and Karin, M., 1987b, Cell 49, 729–739
Billah, M. M., Pai, J.-K., Mullmann, T. J. Egan, R. W. and Siegel, 1989, J. Biol. Chem. 264, 9069–9076.
Brasier, A. R., Tate, J. E. and Habener, J. F. 1989, BioTechniques 7, 1116–1122
Buckley, N. J. et al., 1989, Molecular Pharmacology 35, 469–476
Chung, C. T. and Miller, R. H., 1988, Nucl. Acids Res. 16,
Deutsch, P. J., Hoeffler, J. P., Jameson, J. L. and Habener, J. F., 1988, Proc.Natl.Acad.Sci. USA 85, 7922–7926
DeLuca, M., Wannlund, J. and McElroy, W. D., 1979, Anal. Biochem. 95, 194–198
De Wet, J. R., Wood, K. V., Helinski, D. R., and DeLuca, M., 1985, Proc.Natl.Acad.Sci. USA 82, 7870–7873
De Wet, J. R., Wood, K., DeLuca, M., Helinski, D. and Subramani, S., 1987, Mol. Cell. Biol. 7, 725–737
Dohlman, H. G. et al., 1991, Ann. Rev. Biochem. 60, 653–688
Doods, N. H. and von Meel, J. C. A., 1991, Receptor Data for Biological Experiments, Ellis Horwood Series in Pharmacological Sciences
Felgner, P. L., Gadek, T. R., Holm, M., Roman, R., Chan, H. N., Wenz, M., Northrop, J. P., Ringold, G. M., and Danielsen, M., 1987, Proc.Natl.Acad.Sci. USA 84, 7413–7417.
Grandy, D. K., Zhang, Y., Bouvier, C., Zhou, Q. Y. et al., 1991, Proc. Natl. Acad. Sci. USA 88, 9175–9179
Gritz, L. and Davies, J., 1903, Gene 25, 179–188
Hartmann, A., 1991, BioTec 5, 40–45
Houslay, M. D., 1991, Eur. J. Biochem. 195, 9–27
Julius, D., Huang, K. N., Livelli, T. J. Axel, R. and Jessell, T. M., 1990, Proc.Natl.Acad.Sci. USA 87, 928–932
Karin, M., 1989, TIG 5, 65–67
King, K., Dohlnan, H. G., Thorner, J., Caron, M. G. and Lefkowitz, R. J., 1990, Science 250, 121–123
Kricka, L. J., 1988, Analyt. Biochem. 175, 14–21
Leach, F. R. und Webster, J. J., 1986, in:
Bioluminescence and Chemiluminescence, Part B, Methods in Enzymology 133, 51–70
Lee, W., Mitchell, P. und Tjian, R., 1987, Cell 49, 741–752
Landschulz, W. H., Johnson, P. F. and McKnight, S. L., 1988, Science 240, 1759–1764
Maniatis, T., Fritsch, E. F. and Sambrook, J., 1982, Molecular Cloning: A Laboratory Manual, Cold Spring Harbor, N.Y., Cold Spring Harbour Laboratory
McKnight, S.L, 1980, Nucleic Acids Res. 8, 5949–5964
Montmayeur, J.-P. und Borrelli, E., 1991, Proc.Natl.Acad.Sci. USA 88, 3135–3139
Montminy, M. R., Gonzalez, G. A. and Yamamoto, K. K., 1990, Trends Neurosci. 13, 185
Mulligan, R. and Berg, P., 1981, Proc.Natl.Acad.Sci. USA 78, 2072–2076
Okayama, H. and Berg, P., 1983, Mol. Cell. Biol. 3, 280–289
Potter, H., Weir, L., and Leder, P., 1984, Proc.Natl.Acad.Sci. USA 81, 7161.
Pritchett et al., 1988, EMBO Journal 7, 4135–4140
Saiki, R. K., Gelfand, D. H., Stoffel, S., Scharf, S. J., Higuchi, R., Horn, G. T., Mullis, K. B. und Erlich, H. A., 1988, Science 239, 487–491

Sassone-Corsi, P., Ransone, L. J. and Verra, I. M. , 1990, Oncogene 5, 427–431
Short, et al., 1988, Nucl. Acids Res. 11, 5521–5540
Simon M. I., Strathmann, M. P. und Gautam, N., 1991, Science 252, 802–808
Southern, P. and Berg, P., 1982, J. Mol. Appl. Gen. 1, 327
Stinski, M. F. and Roehr, T. J., 1985, J. Virology 55, 431–441
Subramani, S. and DeLuca, M., 1987, Genetic Engineering, Principles and Methods, J. K. Sedlow ed., Plenum Press, New York, Band 10, 75–89
Sugden, B., Marsh, K. and Yates, J., 1985, Mol. Cell. Biol. 5, 410–413
Turner R. and Tjian, R., 1989, Science 243, 1689–1694
Ullrich, A. and Schlessinger, J., 1990, Cell 61, 203–212
Urlaub, G. and Chasin, L. A., 1980, Proc.Natl.Acad.Sci. USA 77, 4216–4220
Voraberger, G., et al., 1991, J. Immunol. 147, 2777
Wagner, M. J., Sharp, J. A. and Summers, W. C., 1981, Proc.Natl.Acad.Sci. USA 78, 1441–1445
Wieland, E. et al., 1985, Arztl. Lab. 31, 203–214
Winnacker, E. L., 1985, Gene und Klone, Eine Einfuhrung in die Gentechnologie, VCH Verlagsges. Weinheim,
Zhou, Q.-Y., Grandy, D. K., Thambi, L., Kushner, J. A., Van Tol, H. H. M., Cone, R., Pribnow, D., Salon, J., Bunzow, J. R., and Civelli, O., 1990, Nature 347, 76–80
Cloning Vectors: Chapter VIII, Eds. Pouwels, Enger-Valk, Brammer, Elsevier, Amsterdam, New York, Oxford,
Human Pharmacology—Molecular-To-Clinical, Chapter 2: Sites of Action: Receptors, Eds. Wingard., L. B., Brody, T. M., Larner, J. and Schwartz, A., Mosby Year-Book Inc., St. Louis, 1991
TiPS: Receptor Nomenclature Supplement, 1991

What is claimed is:

1. A process for screening a test substance for the ability of the test substance to modulate a receptor-dependent signal transduction pathway in a human or animal cell, wherein said modulation affects the activity of a phospholipase or a mechanism which precedes or succeeds phospholipase activation in the signal transduction pathway initiated by a receptor coupled to the signal transduction pathway, comprising 1) incubating test mammalian cells with the test substance,
wherein said test mammalian cells are:
(a) transformed with a recombinant DNA molecule comprising a reporter gene operably linked to a DNA molecule having a regulatory sequence which responds to a change in concentration of inositol-1, 4,5-triphosphate ($IP_3$) and diacylglycerol (DAG) brought about by the modulation of phospholipase activity in said mammalian cell, whereby the expression of the reporter gene in said mammalian cell is modulated by a change in concentration of $IP_3$/DAG; and (b) transformed with a recombinant DNA molecule comprising a sequence which codes for a receptor protein which is coupled functionally to the phospholipase effector system and wherein said mammalian cells express the receptor protein encoded by the recombinant DNA molecule, with the proviso that said receptor protein is not an ion channel protein;

2) incubating control mammalian cells with said test substance, wherein said control cells are transformed with a recombinant DNA molecule comprising said reporter gene operably linked to a DNA molecule having a regulatory sequence which responds to a change in concentration of $IP_3$/DAG, wherein said change in concentration is brought about by the modulation of phospholipase activity, wherein the same reporter gene and operably controlled regulatory sequence is used in both test and control cells;

3) measuring the concentration of said reporter gene product in said control cells and in said test cells; and
4) comparing the concentration of said reporter gene product in said control cells to the concentration of said reporter gene product in said test cells.

2. The process according to claim 1, further comprising
5) incubating further control mammalian cells with said test substance, wherein said further control mammalian cells are transformed with a recombinant DNA molecule comprising a reporter gene operably linked to a DNA molecule which is coupled functionally to the adenylate cyclase effector system;
6) measuring the concentration of said reporter gene product in said further control cells and in said test cells; and
7) comparing the concentration of said reporter gene product in said further control cells to the concentration of said reporter gene product in said test cells.

3. The process of claim 2, wherein said further control mammalian cells are also transformed with the same recombinant DNA molecule comprising a sequence which codes for a receptor protein which is coupled functionally the phospholipase effector system.

4. The process according to claim 1 or 2, wherein said test and control mammalian cells are selected from the group consisting of CHO cells, COS cells, A549 cells and JEG-3 cells.

5. The process according to claim 1, wherein said recombinant DNA molecule comprising a sequence which codes for a receptor protein codes for a human receptor protein.

6. The process according to claim 1, wherein said recombinant DNA molecule comprising a sequence which codes for a receptor protein codes for a 7 transmembrane receptor protein.

7. The process according to claim 1, wherein said recombinant DNA molecule defined in 1(a) and 2) comprises a regulatory sequence which responds to a change in concentration of $IP_3$ and DAG brought about by modulation of phospholipase C.

8. The process according to claim 1, wherein said process is a screening assay in which said test substance is but one of a number of test substances, wherein a predetermined number of test and control cells are incubated under predetermined conditions which each of said test substances, and the concentration of the reporter gene product is measured.

9. The process according to claim 1, further comprising measuring the concentration of the reporter gene product in the test and control mammalian cells in the absence of said test substance.

10. The process according to claim 1, wherein the reporter gene product is luciferase which is measured in the presence of a reagent which contains a detergent suitable for lysing the cells, a buffer having a pH from 6 to 9, a magnesium salt, adenosine triphosphate, luciferin, and a mild organic reducing reagent.

11. The process according to claim 10, wherein the buffer has a pH of about 7.8, the magnesium salt is magnesium sulphate, and the mild organic reducing agent is dithiothreitol, β-mercaptoethanol, sodium tripolyphosphate or sodium pyrophosphate.

12. The process of claim 1, wherein said process is an automated high-throughput process.

13. A process for screening a test substance for the ability of the test substance to modulate a receptor-dependent signal transduction pathway in a human or animal cell, wherein said modulation affects the adenylate cyclase signal transduction pathway initiated by a receptor coupled to the signal transduction pathway, comprising
1) incubating test mammalian cells with the test substance,
wherein said test mammalian cells are:
(a) transformed with a recombinant DNA molecule comprising a reporter gene operably linked to a DNA molecule having a regulatory sequence which responds to a change in concentration of cAMP; and
(b) transformed with a recombinant DNA molecule comprising a sequence which codes for a receptor protein which is coupled functionally to the adenylate cyclase effector system and wherein said mammalian cells express the receptor protein encoded by the recombinant DNA molecule;
2) incubating control mammalian cells with said test substance, wherein said control cells are transformed with a recombinant DNA molecule comprising said reporter gene operably linked to a DNA molecule having a regulatory sequence which responds to a change in concentration of cAMP, wherein the same reporter gene and operably controlled regulatory sequence is used in both test and control cells;
3) measuring the concentration of said reporter gene product in said control cells and in said test cells;
4) comparing the concentration of said reporter gene product in said control cells to the concentration of said reporter gene product in said test cells;
5) incubating further control mammalian cells with said test substance, wherein said further control mammalian cells are transformed with a recombinant DNA molecule comprising a reporter gene operably linked to a DNA molecule having a regulatory sequence which responds to a change in concentration of $IP_3$ and DAG brought about by the modulation of phospholipase activity in said mammalian cells;
6) measuring the concentration of said reporter gene product in said further control cells and in said test cells; and
7) comparing the concentration of said reporter gene product in said further control cells to the concentration of said reporter gene product in said test cells.

14. The process according to claim 13, wherein said test and control mammalian cells are selected from the group consisting of CHO cells, COS cells, A549 cells and JEG-3 cells.

15. The process according to claim 13, wherein said recombinant DNA molecule comprising a sequence which codes for a receptor protein codes for a human receptor protein.

16. The process according to claim 13, wherein said process is a screening assay in which said test substance is but one of a number of test substances, wherein a predetermined number of test, control cells and further control cells are incubated under predetermined conditions which each of said test substances, and the concentration of the reporter gene product is measured.

17. The process according to claim 13, further comprising measuring the concentration of the reporter gene product in the test, control mammalian cells and further control mammalian cells in the absence of said test substance.

18. The process according to claim 13, wherein the reporter gene product is luciferase which is measured in the presence of a reagent which contains a detergent suitable for lysing the cells, a buffer having a pH from 6 to 9, a magnesium salt, adenosine triphosphate, luciferin, and a mild organic reducing reagent.

19. The process according to claim 18, wherein the buffer has a pH of about 7.8, the magnesium salt is magnesium sulphate, and the mild organic reducing agent is dithiothreitol, β-mercaptoethanol, sodium tripolyphosphate or sodium pyrophosphate.

* * * * *

UNITED STATES PATENT AND TRADEMARK OFFICE
CERTIFICATE OF CORRECTION

PATENT NO. : 5,854,004

DATED : December 29, 1998

INVENTORS : Czernilofsky *et al.*

It is certified that an error appears in the above-identified patent and that said Letters Patent is hereby corrected as shown below.
On the title page, item [75] ("Inventors"), please delete "Schafer" and insert therefor --Schäfer--.

item [73] ("Assignee"), please delete "Ingleheim" and insert therefor --Ingelheim--.

Signed and Sealed this

First Day of June, 1999

Attest:

Attesting Officer

Q. TODD DICKINSON

*Acting Commissioner of Patents and Trademarks*

SEQUENCE LISTING ( 1 ) GENERAL INFORMATION:

( i i i ) NUMBER OF SEQUENCES: 37

( 2 ) INFORMATION FOR SEQ ID NO:1:

( i ) SEQUENCE CHARACTERISTICS:
( A ) LENGTH: 1630 base pairs
( B ) TYPE: nucleic acid
( C ) STRANDEDNESS: both
( D ) TOPOLOGY: unknown ( i i ) MOLECULE TYPE:

( x i ) SEQUENCE DESCRIPTION: SEQ ID NO:1:

```
CGTATCGATA  GCATGTCTGA  TCAGACAGCA  GCTGCGCAGG  GCTCGGAATG  CTACCCTAAA                                60

AGGCCACTCG  AAACCCCAGC  CCCGGGAGAA  CAGCATGTAC  ACCAGCCTCA  GTGTTACAGA                               120

GTGTGGGTAC  ATCAAGGTGA  ATGGTGAGCA  GAAACTATAA  CCTGTTAGTC  CTTCTACACC                               180

TCATCTGCTA  CAAGTTCTGG  CTTAGAC ATG GAT ATT CTT TGT GAA GAA AAT                                     231
                                Met Asp Ile Leu Cys Glu Glu Asn
                                 1                   5

ACT TCT TTG AGC TCA ACT ACG AAC TCC CTA ATG CAA TTA AAT GAT GAC                                     279
Thr Ser Leu Ser Ser Thr Thr Asn Ser Leu Met Gln Leu Asn Asp Asp
    10              15                  20

ACC AGG CTC TAC AGT AAT GAC TTT AAC TCC GGA GAA GCT AAC ACT TCT                                     327
Thr Arg Leu Tyr Ser Asn Asp Phe Asn Ser Gly Glu Ala Asn Thr Ser
25              30                  35                      40

GAT GCA TTT AAC TGG ACA GTC GAC TCT GAA AAT CGA ACC AAC CTT TCC                                     375
Asp Ala Phe Asn Trp Thr Val Asp Ser Glu Asn Arg Thr Asn Leu Ser
                45                  50                  55

TGT GAA GGG TGC CTC TCA CCG TCG TGT CTC TCC TTA CTT CAT CTC CAG                                     423
Cys Glu Gly Cys Leu Ser Pro Ser Cys Leu Ser Leu Leu His Leu Gln
            60                  65                  70

GAA AAA AAC TGG TCT GCT TTA CTG ACA GCC GTA GTG ATT ATT CTA ACT                                     471
Glu Lys Asn Trp Ser Ala Leu Leu Thr Ala Val Val Ile Ile Leu Thr
        75                  80                      85

ATT GCT GGA AAC ATA CTC GTC ATC ATG GCA GTG TCC CTA GAG AAA AAG                                     519
Ile Ala Gly Asn Ile Leu Val Ile Met Ala Val Ser Leu Glu Lys Lys
        90                  95                      100

CTG CAG AAT GCC ACC AAC TAT TTC CTG ATG TCA CTT GCC ATA GCT GAT                                     567
Leu Gln Asn Ala Thr Asn Tyr Phe Leu Met Ser Leu Ala Ile Ala Asp
105                 110                 115                 120
```

| | | | | | | | | | | | | | | | | |
|---|---|---|---|---|---|---|---|---|---|---|---|---|---|---|---|---|
| ATG | CTG | CTG | GGT | TTC | CTT | GTC | ATG | CCC | GTG | TCC | ATG | TTA | ACC | ATC | CTG | 615 |
| Met | Leu | Leu | Gly | Phe | Leu | Val | Met | Pro | Val | Ser | Met | Leu | Thr | Ile | Leu | |
| | | | 125 | | | | 130 | | | | | 135 | | | | |
| TAT | GGG | TAC | CGG | TGG | CCT | CTG | CCG | AGC | AAG | CTT | TGT | GCA | GTC | TGG | ATT | 663 |
| Tyr | Gly | Tyr | Arg | Trp | Pro | Leu | Pro | Ser | Lys | Leu | Cys | Ala | Val | Trp | Ile | |
| | | | 140 | | | | 145 | | | | | 150 | | | | |
| TAC | CTG | GAC | GTG | CTC | TTC | TCC | ACG | GCC | TCC | ATC | ATG | CAC | CTC | TGC | GCC | 711 |
| Tyr | Leu | Asp | Val | Leu | Phe | Ser | Thr | Ala | Ser | Ile | Met | His | Leu | Cys | Ala | |
| | | 155 | | | | | 160 | | | | | 165 | | | | |
| ATC | TCG | CTG | GAC | CGC | TAC | GTC | GCC | ATC | CAG | AAT | CCC | ATC | CAC | CAC | AGC | 759 |
| Ile | Ser | Leu | Asp | Arg | Tyr | Val | Ala | Ile | Gln | Asn | Pro | Ile | His | His | Ser | |
| | 170 | | | | | 175 | | | | | 180 | | | | | |
| CGC | TTC | AAC | TCC | AGA | ACT | AAG | GCA | TTT | CTG | AAA | ATC | ATT | GCT | GTT | TGG | 807 |
| Arg | Phe | Asn | Ser | Arg | Thr | Lys | Ala | Phe | Leu | Lys | Ile | Ile | Ala | Val | Trp | |
| 185 | | | | | 190 | | | | | 195 | | | | | 200 | |
| ACC | ATA | TCA | GTA | GGT | ATA | TCC | ATG | CCA | ATA | CCA | GTC | TTT | GGG | CTA | CAG | 855 |
| Thr | Ile | Ser | Val | Gly | Ile | Ser | Met | Pro | Ile | Pro | Val | Phe | Gly | Leu | Gln | |
| | | | | 205 | | | | 210 | | | | | 215 | | | |
| GAC | GAT | TCG | AAG | GTC | TTT | AAG | GAG | GGG | AGT | TGC | TTA | CTC | GCC | GAT | GAT | 903 |
| Asp | Asp | Ser | Lys | Val | Phe | Lys | Glu | Gly | Ser | Cys | Leu | Leu | Ala | Asp | Asp | |
| | | | 220 | | | | 225 | | | | | 230 | | | | |
| AAC | TTT | GTC | CTG | ATC | GGC | TCT | TTT | GTG | TCA | TTT | TTC | ATT | CCC | TTA | ACC | 951 |
| Asn | Phe | Val | Leu | Ile | Gly | Ser | Phe | Val | Ser | Phe | Phe | Ile | Pro | Leu | Thr | |
| | | 235 | | | | | 240 | | | | | 245 | | | | |
| ATC | ATG | GTG | ATC | ACC | TAC | TTT | CTA | ACT | ATC | AAG | TCA | CTC | CAG | AAA | GAA | 999 |
| Ile | Met | Val | Ile | Thr | Tyr | Phe | Leu | Thr | Ile | Lys | Ser | Leu | Gln | Lys | Glu | |
| | 250 | | | | | 255 | | | | | 260 | | | | | |
| GCT | ACT | TTG | TGT | GTA | AGC | GAT | CTT | GGC | ACA | CGG | GCC | AAA | TTA | GCT | TCT | 1047 |
| Ala | Thr | Leu | Cys | Val | Ser | Asp | Leu | Gly | Thr | Arg | Ala | Lys | Leu | Ala | Ser | |
| 265 | | | | | 270 | | | | | 275 | | | | | 280 | |
| TTC | AGC | TTC | CTC | CCT | CAG | AGT | TCT | TTG | TCT | TCA | GAA | AAG | CTC | TTC | CAG | 1095 |
| Phe | Ser | Phe | Leu | Pro | Gln | Ser | Ser | Leu | Ser | Ser | Glu | Lys | Leu | Phe | Gln | |
| | | | | 285 | | | | | 290 | | | | | 295 | | |
| CGG | TCG | ATC | CAT | AGG | GAG | CCT | GGG | TCC | TAC | ACA | GGC | AGG | AGG | ACT | ATG | 1143 |
| Arg | Ser | Ile | His | Arg | Glu | Pro | Gly | Ser | Tyr | Thr | Gly | Arg | Arg | Thr | Met | |
| | | | 300 | | | | 305 | | | | | 310 | | | | |
| CAG | TCC | ATC | AGC | AAT | GAG | CAA | AAG | GCA | TGC | AAG | GTG | CTG | GGC | ATC | GTC | 1191 |
| Gln | Ser | Ile | Ser | Asn | Glu | Gln | Lys | Ala | Cys | Lys | Val | Leu | Gly | Ile | Val | |
| | | 315 | | | | | 320 | | | | | 325 | | | | |
| TTC | TTC | CTG | TTT | GTG | GTG | ATG | TGG | TGC | CCT | TTC | TTC | ATC | ACA | AAC | ATC | 1239 |
| Phe | Phe | Leu | Phe | Val | Val | Met | Trp | Cys | Pro | Phe | Phe | Ile | Thr | Asn | Ile | |
| | 330 | | | | | 335 | | | | | 340 | | | | | |
| ATG | GCC | GTC | ATC | TGC | AAA | GAG | TCC | TGC | AAT | GAG | GAT | GTC | ATT | GGG | GCC | 1287 |
| Met | Ala | Val | Ile | Cys | Lys | Glu | Ser | Cys | Asn | Glu | Asp | Val | Ile | Gly | Ala | |
| 345 | | | | | 350 | | | | | 355 | | | | | 360 | |
| CTG | CTC | AAT | GTG | TTT | GTT | TGG | ATC | GGT | TAT | CTC | TCT | TCA | GCA | GTC | AAC | 1335 |
| Leu | Leu | Asn | Val | Phe | Val | Trp | Ile | Gly | Tyr | Leu | Ser | Ser | Ala | Val | Asn | |
| | | | | 365 | | | | | 370 | | | | | 375 | | |
| CCA | CTA | GTC | TAC | ACA | CTG | TTC | AAC | AAG | ACC | TAT | AGG | TCA | GCC | TTT | TCA | 1383 |
| Pro | Leu | Val | Tyr | Thr | Leu | Phe | Asn | Lys | Thr | Tyr | Arg | Ser | Ala | Phe | Ser | |
| | | | 380 | | | | 385 | | | | | 390 | | | | |
| CGG | TAT | ATT | CAG | TGT | CAG | TAC | AAG | GAA | AAC | AAA | AAA | CCA | TTG | CAG | TTA | 1431 |
| Arg | Tyr | Ile | Gln | Cys | Gln | Tyr | Lys | Glu | Asn | Lys | Lys | Pro | Leu | Gln | Leu | |
| | | 395 | | | | | 400 | | | | | 405 | | | | |
| ATT | TTA | GTG | AAC | ACA | ATA | CCG | GCT | TTG | GCC | TAC | AAG | TCT | AGC | CAA | CTT | 1479 |
| Ile | Leu | Val | Asn | Thr | Ile | Pro | Ala | Leu | Ala | Tyr | Lys | Ser | Ser | Gln | Leu | |
| | 410 | | | | | 415 | | | | | 420 | | | | | |
| CAA | ATG | GGA | CAA | AAA | AAG | AAT | TCA | AAG | CAA | GAT | GCC | AAG | ACA | ACA | GAT | 1527 |
| Gln | Met | Gly | Gln | Lys | Lys | Asn | Ser | Lys | Gln | Asp | Ala | Lys | Thr | Thr | Asp | |
| 425 | | | | | 430 | | | | | 435 | | | | | 440 | |

-continued

| AAT | GAC | TGC | TCA | ATG | GTT | GCT | CTA | GGA | AAG | CAG | CAT | TCT | GAA | GAG | GCT | 1575 |
| Asn | Asp | Cys | Ser | Met | Val | Ala | Leu | Gly | Lys | Gln | His | Ser | Glu | Glu | Ala | |
| | | | | 445 | | | | 450 | | | | | 455 | | | |

| TCT | AAA | GAC | AAT | AGC | GAC | GGA | GTG | AAT | GAA | AAG | GTG | AGC | TGT | | | |
| Ser | Lys | Asp | Asn | Ser | Asp | Gly | Val | Asn | Glu | Lys | Val | Ser | Cys | | | |
| | | | 460 | | | | | 465 | | | | | 470 | | | |

| | | | | | | | | | | | | GTG | TGATAGGCTA | 1630 |
| | | | | | | | | | | | | Val | | |

(2) INFORMATION FOR SEQ ID NO:2:

(i) SEQUENCE CHARACTERISTICS:
        (A) LENGTH: 471 amino acids
        (B) TYPE: amino acid
        (D) TOPOLOGY: linear (ii) MOLECULE TYPE: protein (xi) SEQUENCE DESCRIPTION: SEQ ID NO:2:

| Met | Asp | Ile | Leu | Cys | Glu | Glu | Asn | Thr | Leu | Ser | Ser | Thr | Thr | Asn |
| 1 | | | | 5 | | | | | 10 | | | | | 15 |

| Ser | Leu | Met | Gln | Leu | Asn | Asp | Asp | Thr | Arg | Leu | Tyr | Ser | Asn | Asp | Phe |
| | | | 20 | | | | | 25 | | | | | 30 | | |

| Asn | Ser | Gly | Glu | Ala | Asn | Thr | Ser | Asp | Ala | Phe | Asn | Trp | Thr | Val | Asp |
| | | | 35 | | | | | 40 | | | | | 45 | | |

| Ser | Glu | Asn | Arg | Thr | Asn | Leu | Ser | Cys | Glu | Gly | Cys | Leu | Ser | Pro | Ser |
| | 50 | | | | | 55 | | | | | 60 | | | | |

| Cys | Leu | Ser | Leu | Leu | His | Leu | Gln | Glu | Lys | Asn | Trp | Ser | Ala | Leu | Leu |
| 65 | | | | | 70 | | | | | 75 | | | | | 80 |

| Thr | Ala | Val | Val | Ile | Ile | Leu | Thr | Ile | Ala | Gly | Asn | Ile | Leu | Val | Ile |
| | | | | 85 | | | | | 90 | | | | | 95 | |

| Met | Ala | Val | Ser | Leu | Glu | Lys | Lys | Leu | Gln | Asn | Ala | Thr | Asn | Tyr | Phe |
| | | | | 100 | | | | | 105 | | | | | 110 | |

| Leu | Met | Ser | Leu | Ala | Ile | Ala | Asp | Met | Leu | Leu | Gly | Phe | Leu | Val | Met |
| | | | 115 | | | | | 120 | | | | | 125 | | |

| Pro | Val | Ser | Met | Leu | Thr | Ile | Leu | Tyr | Gly | Tyr | Arg | Trp | Pro | Leu | Pro |
| | | | 130 | | | | | 135 | | | | | 140 | | |

| Ser | Lys | Leu | Cys | Ala | Val | Trp | Ile | Tyr | Leu | Asp | Val | Leu | Phe | Ser | Thr |
| 145 | | | | | 150 | | | | | 155 | | | | | 160 |

| Ala | Ser | Ile | Met | His | Leu | Cys | Ala | Ile | Ser | Leu | Asp | Arg | Tyr | Val | Ala |
| | | | | 165 | | | | | 170 | | | | | 175 | |

| Ile | Gln | Asn | Pro | Ile | His | His | Ser | Arg | Phe | Asn | Ser | Arg | Thr | Lys | Ala |
| | | | 180 | | | | | 185 | | | | | 190 | | |

| Phe | Leu | Lys | Ile | Ile | Ala | Val | Trp | Thr | Ile | Ser | Val | Gly | Ile | Ser | Met |
| | | 195 | | | | | 200 | | | | | 205 | | | |

| Pro | Ile | Pro | Val | Phe | Gly | Leu | Gln | Asp | Asp | Ser | Lys | Val | Phe | Lys | Glu |
| | 210 | | | | | 215 | | | | | 220 | | | | |

| Gly | Ser | Cys | Leu | Leu | Ala | Asp | Asp | Asn | Phe | Val | Leu | Ile | Gly | Ser | Phe |
| 225 | | | | | 230 | | | | | 235 | | | | | 240 |

| Val | Ser | Phe | Phe | Ile | Pro | Leu | Thr | Ile | Met | Val | Ile | Thr | Tyr | Phe | Leu |
| | | | | 245 | | | | | 250 | | | | | 255 | |

| Thr | Ile | Lys | Ser | Leu | Gln | Lys | Glu | Ala | Thr | Leu | Cys | Val | Ser | Asp | Leu |
| | | | 260 | | | | | 265 | | | | | 270 | | |

| Gly | Thr | Arg | Ala | Lys | Leu | Ala | Ser | Phe | Ser | Phe | Leu | Pro | Gln | Ser | Ser |
| | | 275 | | | | | 280 | | | | | 285 | | | |

| Leu | Ser | Ser | Glu | Lys | Leu | Phe | Gln | Arg | Ser | Ile | His | Arg | Glu | Pro | Gly |
| | 290 | | | | | 295 | | | | | 300 | | | | |

| Ser | Tyr | Thr | Gly | Arg | Arg | Thr | Met | Gln | Ser | Ile | Ser | Asn | Glu | Gln | Lys |
| 305 | | | | | 310 | | | | 315 | | | | | | 320 |

| Ala | Cys | Lys | Val | Leu | Gly | Ile | Val | Phe | Phe | Leu | Phe | Val | Val | Met | Trp |
| | | | | 325 | | | | | 330 | | | | | 335 | |

| Cys | Pro | Phe | Phe | Ile | Thr | Asn | Ile | Met | Ala | Val | Ile | Cys | Lys | Glu | Ser |
| | | | 340 | | | | | 345 | | | | | 350 | | |

| Cys | Asn | Glu | Asp | Val | Ile | Gly | Ala | Leu | Leu | Asn | Val | Phe | Val | Trp | Ile |
| | | 355 | | | | | 360 | | | | | 365 | | | |

| Gly | Tyr | Leu | Ser | Ser | Ala | Val | Asn | Pro | Leu | Val | Tyr | Thr | Leu | Phe | Asn |
| | 370 | | | | | 375 | | | | | 380 | | | | |

| Lys | Thr | Tyr | Arg | Ser | Ala | Phe | Ser | Arg | Tyr | Ile | Gln | Cys | Gln | Tyr | Lys |
| 385 | | | | | 390 | | | | | 395 | | | | | 400 |

| Glu | Asn | Lys | Lys | Pro | Leu | Gln | Leu | Ile | Leu | Val | Asn | Thr | Ile | Pro | Ala |
| | | | | 405 | | | | | 410 | | | | | 415 | |

| Leu | Ala | Tyr | Lys | Ser | Ser | Gln | Leu | Gln | Met | Gly | Gln | Lys | Lys | Asn | Ser |
| | | | 420 | | | | | 425 | | | | | 430 | | |

| Lys | Gln | Asp | Ala | Lys | Thr | Thr | Asp | Asn | Asp | Cys | Ser | Met | Val | Ala | Leu |
| | | 435 | | | | 440 | | | | | 445 | | | | |

| Gly | Lys | Gln | His | Ser | Glu | Glu | Ala | Ser | Lys | Asp | Asn | Ser | Asp | Gly | Val |
| | 450 | | | | | 455 | | | | | 460 | | | | |

| Asn | Glu | Lys | Val | Ser | Cys | Val |
| 465 | | | | | 470 | |

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:3:

GGAATTCGCG CCCTGTAGCG GCG        23

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:4:

CACTGAACTC GAGCAGCTGC GTTGCTGGCG TTTTTCC        37

( 2 ) INFORMATION FOR SEQ ID NO:5:

( i ) SEQUENCE CHARACTERISTICS:
        ( A ) LENGTH: 64 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:5:

GACTTCAGAT CTGCGGCCGC CTCGAGGGTA CCGTTAACGT CGACAAACCC CGCCCAGCGT        60

CTTG        64

( 2 ) INFORMATION FOR SEQ ID NO:6:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:6:

GACTTCGGAT CCGAGCTCAC TAGTTCTAGA AAGCTTGACG CTGTTAAGCG GGTCGC      56

( 2 ) INFORMATION FOR SEQ ID NO:7:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:7:

GACTTCGGAT CCGAGCTCAC TAGTTCTAGA AAGCTTGACG CTGTTAAGCG GGTCGC      56

( 2 ) INFORMATION FOR SEQ ID NO:8:

( i ) SEQUENCE CHARACTERISTICS:
        ( A ) LENGTH: 45 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:8:

AGCTTGTAAG CAGCAGCTGC AGTGCTCTGC CTTTTATGCC CAAGG      45

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:9:

TCGATGCGGC CGCGACTTCA G      21

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:10:

CTGAAGTCGC GGCCGCA      17

( 2 ) INFORMATION FOR SEQ ID NO:11:

( i ) SEQUENCE CHARACTERISTICS:
        ( A ) LENGTH: 25 base pairs

```
         ( B ) TYPE: nucleic acid
         ( C ) STRANDEDNESS: both
         ( D ) TOPOLOGY: linear ( i i ) MOLECULE TYPE: oligonucleotide ( x i ) SEQUENCE DESCRIPTION: SEQ ID NO:11:
```

GGCAGCTGAC GTCACTGTCT GGTGC                                                     25

( 2 ) INFORMATION FOR SEQ ID NO:12:

```
    ( i ) SEQUENCE CHARACTERISTICS:
         ( A ) LENGTH: 35 base pairs
         ( B ) TYPE: nucleic acid
         ( C ) STRANDEDNESS: both
         ( D ) TOPOLOGY: linear ( i i ) MOLECULE TYPE: oligonucleotide ( x i ) SEQUENCE DESCRIPTION: SEQ ID NO:12:
```

CTCCTTGGCT GACGTCAGTA GAGAGATCCC ATGGC                                          35

( 2 ) INFORMATION FOR SEQ ID NO:13:

```
    ( i ) SEQUENCE CHARACTERISTICS:
         ( A ) LENGTH: 27 base pairs
         ( B ) TYPE: nucleic acid
         ( C ) STRANDEDNESS: both
         ( D ) TOPOLOGY: linear ( i i ) MOLECULE TYPE: oligonucleotide ( x i ) SEQUENCE DESCRIPTION: SEQ ID NO:13:
```

CTCTACTGAC GTCAGCCAAG GAGGTAC                                                   27

( 2 ) INFORMATION FOR SEQ ID NO:14:

```
    ( i ) SEQUENCE CHARACTERISTICS:
         ( A ) LENGTH: 47 base pairs
         ( B ) TYPE: nucleic acid
         ( C ) STRANDEDNESS: both
         ( D ) TOPOLOGY: linear ( i i ) MOLECULE TYPE: oligonucleotide ( x i ) SEQUENCE DESCRIPTION: SEQ ID NO:14:
```

CGTCATACTG TGACGTCTTT CAGACACCCC ATTGACGTCA ATGGGAG                             47

( 2 ) INFORMATION FOR SEQ ID NO:15:

```
    ( i ) SEQUENCE CHARACTERISTICS:
         ( A ) LENGTH: 41 base pairs
         ( B ) TYPE: nucleic acid
         ( C ) STRANDEDNESS: both
         ( D ) TOPOLOGY: linear ( i i ) MOLECULE TYPE: oligonucleotide ( x i ) SEQUENCE DESCRIPTION: SEQ ID NO:15:
```

GGCCGCACCA GACAGTGACG TCAGCTGCCA GATCCCATGG C                                   41

( 2 ) INFORMATION FOR SEQ ID NO:16:

```
    ( i ) SEQUENCE CHARACTERISTICS:
         ( A ) LENGTH: 35 base pairs
         ( B ) TYPE: nucleic acid
         ( C ) STRANDEDNESS: both
         ( D ) TOPOLOGY: linear ( i i ) MOLECULE TYPE: oligonucleotide
```

( x i ) SEQUENCE DESCRIPTION: SEQ ID NO:16:

CTCCTTGGCT GACGTCAGTA GAGAGATCCC ATGGC     35

( 2 ) INFORMATION FOR SEQ ID NO:17:

( i ) SEQUENCE CHARACTERISTICS:
        ( A ) LENGTH: 63 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:17:

TCGACTCCCA TTGACGTCAA TGGGGTGTCT GAAAGACGTC ACAGTATGAC GGCCATGGGA     60

TCT     63

( 2 ) INFORMATION FOR SEQ ID NO:18:

( i ) SEQUENCE CHARACTERISTICS:
        ( A ) LENGTH: 57 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:18:

GGCCGCAGGT ACCAGATCTA CTCGAGTGTA GACCGTGATT CAAGCTTAGC TGTAGAC     57

( 2 ) INFORMATION FOR SEQ ID NO:19:

( i ) SEQUENCE CHARACTERISTICS:
        ( A ) LENGTH: 41 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:19:

GCTTGAATCA CGGTCTACAC TCGAGTAGAT CTGGTACCTG C     41

( 2 ) INFORMATION FOR SEQ ID NO:20:

( i ) SEQUENCE CHARACTERISTICS:
        ( A ) LENGTH: 56 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:20:

TCGACTAAGC TTGAATCACG GTCTACAGCT AAGCTTGAAT CACGGTCTAC AGCTAA     56

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:21:

CGTGATTCAA GCTTAGCTGT AGACCGTGAT TCAAGCTTAG                                      40

( 2 ) INFORMATION FOR SEQ ID NO:22:

( i ) SEQUENCE CHARACTERISTICS:
          ( A ) LENGTH: 56 base pairs
          ( B ) TYPE: nucleic acid
          ( C ) STRANDEDNESS: both
          ( D ) TOPOLOGY: linear ( i i ) MOLECULE TYPE: oligonucleotide ( x i ) SEQUENCE DESCRIPTION: SEQ ID NO:22:

GGCCGCAGGT ACCAGATCTA CTCGAGTGTA GACCGTGATT CAAGCTTAGT GTAGAC          56

( 2 ) INFORMATION FOR SEQ ID NO:23:

( i ) SEQUENCE CHARACTERISTICS:
          ( A ) LENGTH: 50 base pairs
          ( B ) TYPE: nucleic acid
          ( C ) STRANDEDNESS: both
          ( D ) TOPOLOGY: linear ( i i ) MOLECULE TYPE: oligonucleotide ( x i ) SEQUENCE DESCRIPTION: SEQ ID NO:23:

TCGACCTTGA ATCACGGTCT ACACTAAGCT TGAATCACGG TCTACACTAA                 50

( 2 ) INFORMATION FOR SEQ ID NO:24:

( i ) SEQUENCE CHARACTERISTICS:
          ( A ) LENGTH: 35 base pairs
          ( B ) TYPE: nucleic acid
          ( C ) STRANDEDNESS: both
          ( D ) TOPOLOGY: linear ( i i ) MOLECULE TYPE: oligonucleotide ( x i ) SEQUENCE DESCRIPTION: SEQ ID NO:24:

CGTGATTCAA GCTTAGTGTA GACCGTGATT CAAGG                                 35

( 2 ) INFORMATION FOR SEQ ID NO:25:

( i ) SEQUENCE CHARACTERISTICS:
          ( A ) LENGTH: 53 base pairs
          ( B ) TYPE: nucleic acid
          ( C ) STRANDEDNESS: both
          ( D ) TOPOLOGY: linear ( i i ) MOLECULE TYPE: oligonucleotide ( x i ) SEQUENCE DESCRIPTION: SEQ ID NO:25:

GGCCGCAGGT ACCAGATCTA CTCGAGTGTA GACCGTGATT CAAGCTTAGC CTG             53

( 2 ) INFORMATION FOR SEQ ID NO:26:

( i ) SEQUENCE CHARACTERISTICS:
          ( A ) LENGTH: 64 base pairs
          ( B ) TYPE: nucleic acid
          ( C ) STRANDEDNESS: both
          ( D ) TOPOLOGY: linear ( i i ) MOLECULE TYPE: oligonucleotide ( x i ) SEQUENCE DESCRIPTION: SEQ ID NO:26:

TCGACTAAGC TTGAATCACG GTCTACACCA GGCTAAGCTT GAATCACGGT CTACACCAGG      60

CTAA                                                                   64

( 2 ) INFORMATION FOR SEQ ID NO:27:

( i ) SEQUENCE CHARACTERISTICS:
        ( A ) LENGTH: 52 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:27:

```
GTGTAGACCG TGATTCAAGC TTAGCCTGGT GTAGACCGTG ATTCAAGCTT AG          52
```

( 2 ) INFORMATION FOR SEQ ID NO:28:

( i ) SEQUENCE CHARACTERISTICS:
        ( A ) LENGTH: 64 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:28:

```
GGCCGCAGGT ACCAGATCTA CTCGAGTGTA GACCGTGATT CAAGCTTAGC CTGGCGGTGT  60

AGAC                                                              64
```

( 2 ) INFORMATION FOR SEQ ID NO:29:

( i ) SEQUENCE CHARACTERISTICS:
        ( A ) LENGTH: 50 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:29:

```
CCAGGCTAAG CTTGAATCAC GGTCTACACT CGAGTAGATC TGGTACCTGC            50
```

( 2 ) INFORMATION FOR SEQ ID NO:30:

( i ) SEQUENCE CHARACTERISTICS:
        ( A ) LENGTH: 51 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:30:

```
CGTGATTCAA GCTTAGCCTG GCGGTGTAGA CCGTGATTCA AGCTTAGCCT G          51
```

( 2 ) INFORMATION FOR SEQ ID NO:31:

( i ) SEQUENCE CHARACTERISTICS:
        ( A ) LENGTH: 65 base pairs
        ( B ) TYPE: nucleic acid
        ( C ) STRANDEDNESS: both
        ( D ) TOPOLOGY: linear ( i i ) MOLECULE TYPE: oligonucleotide ( x i ) SEQUENCE DESCRIPTION: SEQ ID NO:31:

```
TCGACAGGCT AAGCTTGAAT CACGGTCTAC ACCGCCAGGC TAAGCTTGAA TCACGGTCTA  60

CACCG                                                             65
```

( 2 ) INFORMATION FOR SEQ ID NO:32:

( i ) SEQUENCE CHARACTERISTICS:
  ( A ) LENGTH: 74 base pairs
  ( B ) TYPE: nucleic acid
  ( C ) STRANDEDNESS: both
  ( D ) TOPOLOGY: linear ( i i ) MOLECULE TYPE: oligonucleotide ( x i ) SEQUENCE DESCRIPTION: SEQ ID NO:32:

```
GGCCGCAGGT ACCAGATCTA CTCGAGTGTA GACCGTGATT CAAGCTTAGC CTGGCCGGTT      60

AGCGCGGTGT AGAC                                                        74
```

( 2 ) INFORMATION FOR SEQ ID NO:33:

( i ) SEQUENCE CHARACTERISTICS:
    ( A ) LENGTH: 62 base pairs
    ( B ) TYPE: nucleic acid
    ( C ) STRANDEDNESS: both
    ( D ) TOPOLOGY: linear ( i i ) MOLECULE TYPE: oligonucleotide ( x i ) SEQUENCE DESCRIPTION: SEQ ID NO:33:

```
CGCGCTAACC GGCCAGGCTA AGCTTGAATC ACGGTCTACA CTCGAGTAGA TCTGGTACCT      60

GC                                                                     62
```

( 2 ) INFORMATION FOR SEQ ID NO:34:

( i ) SEQUENCE CHARACTERISTICS:
    ( A ) LENGTH: 73 base pairs
    ( B ) TYPE: nucleic acid
    ( C ) STRANDEDNESS: both
    ( D ) TOPOLOGY: linear ( i i ) MOLECULE TYPE: oligonucleotide ( x i ) SEQUENCE DESCRIPTION: SEQ ID NO:34:

```
TCGACAGGCT AAGCTTGAAT CACGGTCTAC ACCGCGCTAA CCGGCCAGGC TAAGCTTGAA      60

TCACGGTCTA CAC                                                         73
```

( 2 ) INFORMATION FOR SEQ ID NO:35:

( i ) SEQUENCE CHARACTERISTICS:
    ( A ) LENGTH: 61 base pairs
    ( B ) TYPE: nucleic acid
    ( C ) STRANDEDNESS: both
    ( D ) TOPOLOGY: linear ( i i ) MOLECULE TYPE: oligonucleotide ( x i ) SEQUENCE DESCRIPTION: SEQ ID NO:35:

```
CGTGATTCAA GCTTAGCCTG GCCGGTTAGC GCGGTGTAGA CCGTGATTCA AGCTTAGCCT      60

G                                                                      61
```

( 2 ) INFORMATION FOR SEQ ID NO:36:

( i ) SEQUENCE CHARACTERISTICS:
    ( A ) LENGTH: 6623 base pairs
    ( B ) TYPE: nucleic acid
    ( C ) STRANDEDNESS: both
    ( D ) TOPOLOGY: circular ( i i ) MOLECULE TYPE:

( x i ) SEQUENCE DESCRIPTION: SEQ ID NO:36:

```
   AATCAATATT GGCAATTAGC CATATTAGTC ATTGGTTATA TAGCATGAAT CAATATTGGC    60
```

-continued

```
TATTGGCCAT TGCATACGTT GTATCTATAT CATAATATGT ACATTTATAT TGGCTCATGT   120
CCAATATGAC CGCCATGTTG ACATTGATTA TTGACTAGTT ATTAATAGTA ATCAATTACG   180
GGGTCATTAG TTCATAGCCC ATATATGGAG TTCCGCGTTA CATAACTTAC GGTAAATGGC   240
CCGCCTGGCT GACCGCCCAA CGACCCCCGC CCATTGACGT CAATAATGAC GTATGTTCCC   300
ATAGTAACGC CAATAGGGAC TTTCCATTGA CGTCAATGGG TGGAGTATTT ACGGTAAACT   360
GCCCACTTGG CAGTACATCA AGTGTATCAT ATGCCAAGTA CGCCCCCTAT TGACGTCAAT   420
GACGGTAAAT GGCCCGCCTG GCATTATGCC CAGTACATGA CCTTATGGGA CTTTCCTACT   480
TGGCAGTACA TCTACGTATT AGTCATCGCT ATTACCATGG TGATGCGGTT TTGGCAGTAC   540
ATCAATGGGC GTGGATAGCG GTTTGACTCA CGGGGATTTC CAAGTCTCCA CCCCATTGAC   600
GTCAATGGGA GTTTGTTTTG GCACCAAAAT CAACGGGACT TTCCAAAATG TCGTAACAAC   660
TCCGCCCCAT TGACGCAAAT GGGCGGTAGG CGTGTACGGT GGGAGGTCTA TATAAGCAGA   720
GCTCTCTGGC TAACTAGAGA ACCCACTGCT TACTGGCTTA TCGAAATTAA TACGACTCAC   780
TATAGGGAGA CCCAAGCTTC TGCAGGTCGA CATCGATGGA TCCGGTACCT CGAGCGGCCG   840
CGAATTCTCT AGAGGATCTT TGTGAAGGAA CCTTACTTCT GTGGTGTGAC ATAATTGGAC   900
AAACTACCTA CAGAGATTTA AAGCTCTAAG GTAAATATAA AATTTTTAAG TGTATAATGT   960
GTTAAACTAC TGATTCTAAT TGTTTGTGTA TTTAGATTC  CAACCTATGG AACTGATGAA  1020
TGGGAGCAGT GGTGGAATGC CTTAATGAG  GAAAACCTGT TTTGCTCAGA AGAAATGCCA  1080
TCTAGTGATG ATGAGGCTAC TGCTGACTCT CAACATTCTA CTCCTCCAAA AAAGAAGAGA  1140
AAGGTAGAAG ACCCCAAGGA CTTTCCTTCA GAATTGCTAA GTTTTTTGAG TCATGCTGTG  1200
TTTAGTAATA GAACTCTTGC TTGCTTTGCT ATTTACACCA CAAAGGAAAA AGCTGCACTG  1260
CTATACAAGA AAATTATGGA AAAATATTTG ATGTATAGTG CCTTGACTAG AGATCATAAT  1320
CAGCCATACC ACATTTGTAG AGGTTTTACT TGCTTTAAAA AACCTCCCAC ACCTCCCCCT  1380
GAACCTGAAA CATAAAATGA ATGCAATTGT TGTTGTTAAC TTGTTTATTG CAGCTTATAA  1440
TGGTTACAAA TAAAGCAATA GCATCACAAA TTTCACAAAT AAAGCATTTT TTTCACTGCA  1500
TTCTAGTTGT GGTTTGTCCA AACTCATCAA TGTATCTTAT CATGTCTGGA TCAATTCTGA  1560
AAAACTAGCC TTAAAGACAG ACAGCTTTGT TCTAGTCAGC CAGGCAAGCA TATGTAAATA  1620
AAGTTCCTCA GGGAACTGAG GTTAAAAGAT GTATCCTGGA CCTGCCAGAC CTGGCCATTC  1680
ACGTAAACAG AAGATTCCGC CTCAAGTTCC GGTTAACAAC AGGAGGCAAC GAGATCATCG  1740
CTGTTCCTTA GGACCCTTTT ACTAACCCTA ATTCGATAGC ATATGCTTCC CGTTGGGTAA  1800
CATATGCTAT TGAATTAGGG TTAGTCTGGA TAGTATATAC TACTACCCGG GAAGCATATG  1860
CTACCCGTTT AGGGTTAACA AGGGGGCCTT ATAAACACTA TTGCTAATGC CCTCTTGAGG  1920
GTCCGCTTAT CGGTAGCTAC ACAGGCCCCT CTGATTGACG TTGGTGTAGC CTCCCGTAGT  1980
CTTCCTGGGC CCCTGGGAGG TACATGTCCC CCAGCATTGG TGTAAGAGCT TCAGCCAAGA  2040
GTTACACATA AAGGCAATGT TGTGTTGCAG TCCACAGACT GCAAAGTCTG CTCCAGGATG  2100
AAAGCCACTC AGTGTTGGCA AATGTGCACA TCCATTTATA AGGATGTCAA CTACAGTCAG  2160
AGAACCCCTT TGTGTTTGGT CCCCCCCCGT GTCACATGTG AACAGGGCC  CAGTTGGCAA  2220
GTTGTACCAA CCAACTGAAG GGATTACATG CACTGCCCCG CGTGAGCAAT ACAAAACAAA  2280
AGCGCTCCTC GTACCAGCGA AGAAGGGGCA GAGATGCCGT AGTCAGGTTT AGTTCGTCCG  2340
GCGGCGCCAG AAATCCGCGC GGTGGTTTTT GGGGGTCGGG GGTGTTTGGC AGCCACAGAC  2400
GCCCGGTGTT CGTGTCGCGC CAGTACATGC GGTCCATGCC CAGGCCATCC AAAAACCATG  2460
```

```
GGTCTGTCTG  CTCAGTCCAG  TCGTGGACCT  GACCCCACGC  AACGCCCAAA  AGAATAACCC  2520
CCACGAACCA  TAAACCATTC  CCCATGGGGG  ACCCCGTCCC  TAACCCACGG  GGCCCGTGGC  2580
TATGGCGGGC  TTGCCGCCCC  GACGTTGGCT  GCGAGCCCTG  GGCCTTCACC  CGAACTTGGG  2640
GGTTGGGGTG  GGGAAAAGGA  AGAAACGCGG  GCGTATTGGC  CCCAATGGGG  TCTCGGTGGG  2700
GTATCGACAG  AGTGCCAGCC  CTGGGACCGA  ACCCCGCGTT  TATGAACAAA  CGACCCAACA  2760
CCCGTGCGTT  TTATTCTGTC  TTTTTATTGC  CGTCATAGCG  CGGGTTCCTT  CCGGTATTGT  2820
CTCCTTCCGT  GTTTCAGTTA  GCCTCCCCCA  TCTCCCGATC  CCTATTCCTT  TGCCCTCGGA  2880
CGAGTGCTGG  GGCGTCGGTT  TCCACTATCG  GCGAGTACTT  CTACACAGCC  ATCGGTCCAG  2940
ACGGCCGCGC  TTCTGCGGGC  GATTTGTGTA  CGCCCGACAG  TCCCGGCTCC  GGATCGGACG  3000
ATTGCGTCGC  ATCGACCCTG  CGCCCAAGCT  GCATCATCGA  AATTGCCGTC  AACCAAGCTC  3060
TGATAGAGTT  GGTCAAGACC  AATGCGGAGC  ATATACGCCC  GGAGCCGCGG  CGATCCTGCA  3120
AGCTCCGGAT  GCCTCCGCTC  GAAGTAGCGC  GTCTGCTGCT  CCATACAAGC  CAACCACGGC  3180
CTCCAGAAGA  AGATGTTGGC  GACCTCGTAT  TGGGAATCCC  CGAACATCGC  CTCGCTCCAG  3240
TCAATGACCG  CTGTTATGCG  GCCATTGTCC  GTCAGGACAT  TGTTGGAGCC  GAAATCCGCG  3300
TGCACGAGGT  GCCGGACTTC  GGGGCAGTCC  TCGGCCCAAA  GCATCAGCTC  ATCGAGAGCC  3360
TGCGCGACGG  ACGCACTGAC  GGTGTCGTCC  ATCACAGTTT  GCCAGTGATA  CACATGGGGA  3420
TCAGCAATCG  CGCATATGAA  ATCACGCCAT  GTAGTGTATT  GACCGATTCC  TTGCGGTCCG  3480
AATGGGCCGA  ACCCGCTCGT  CTGGCTAAGA  TCGGCCGCAG  CGATCGCATC  CATGGCCTCC  3540
GCGACCGGCT  GCAGAACAGC  GGGCAGTTCG  GTTTCAGGCA  GGTCTTGCAA  CGTGACACCC  3600
TGTGCACGGC  GGGAGATGCA  ATAGGTCAGG  CTCTCGCTGA  ATTCCCCAAT  GTCAAGCACT  3660
TCCGGAATCG  GGAGCGCGGC  CGATGCAAAG  TGCCGATAAA  CATAACGATC  TTTGTAGAAA  3720
CCATCGGCGC  AGCTATTTAC  CCGCAGGACA  TATCCACGCC  CTCCTACATC  GAAGCTGAAA  3780
GCACGAGATT  CTTCGCCCTC  CGAGAGCTGC  ATCAGGTCGG  AGACGCTGTC  GAACTTTTCG  3840
ATCAGAAACT  TCTCGACAGA  CGTCGCGGTG  AGTTCAGGCT  TTTTCATATC  TCATTGCCCC  3900
CGGACGAGGA  TCTGCGGCAC  GCTGTTGACG  CTGTTAAGCG  GGTCGCTGCA  GGGTCGCTCG  3960
GTGTTCGAGG  CCACACGCGT  CACCTTAATA  TGCGAAGTGG  ACCTGGGACC  GCGCCGCCCC  4020
GACTGCATCT  GCGTGTTCGA  ATTCGCCAAT  GACAAGACGC  TGGGCGGGGT  TTGTGTCATC  4080
ATAGAACTAA  AGACATGCAA  ATATATTTCT  TCCGGGGACA  CCGCCAGCAA  ACGCGAGCAA  4140
CGGGCCACGG  GGATGAAGCA  GGGCGGCACC  TCGCTAACGG  ATTCACCACT  CCAAGAATTG  4200
GAGCCAATCA  ATTCTTGCGG  AGAACTGTGA  ATGCGCAAAC  CAACCCTTGG  CAGAACATAT  4260
CCATCGCGTC  CGCCATCTCC  AGCAGCCGCA  CGCGGCGCAT  CTCGGGCAGC  GTTGGGTCCT  4320
GGCCACGGGT  GCGCATGATC  GTGCTCCTGT  CGTTGAGGAC  CCGGCTAGGC  TGGCGGGGTT  4380
GCCTTACTGG  TTAGCAGAAT  GAATCACCGA  TACGCGAGCG  AACGTGAAGC  GACTGCTGCT  4440
GCAAAACGTC  TGCGACCTGA  GCAACAACAT  GAATGGTCTT  CGGTTTCCGT  GTTTCGTAAA  4500
GTCTGGAAAC  GCGGAAGTCA  GCGCTCTTCC  GCTTCCTCGC  TCACTGACTC  GCTGCGCTCG  4560
GTCGTTCGGC  TGCGGCGAGC  GGTATCAGCT  CACTCAAAGG  CGGTAATACG  GTTATCCACA  4620
GAATCAGGGG  ATAACGCAGG  AAAGAACATG  TGAGCAAAAG  GCCAGCAAAA  GGCCAGGAAC  4680
CGTAAAAAGG  CCGCGTTGCT  GGCGTTTTTC  CATAGGCTCC  GCCCCCTGA   CGAGCATCAC  4740
AAAAATCGAC  GCTCAAGTCA  GAGGTGGCGA  AACCCGACAG  GACTATAAAG  ATACCAGGCG  4800
TTTCCCCCTG  GAAGCTCCCT  CGTGCGCTCT  CCTGTTCCGA  CCCTGCCGCT  TACCGGATAC  4860
```

-continued

```
CTGTCCGCCT  TTCTCCCTTC  GGGAAGCGTG  GCGCTTTCTC  ATAGCTCACG  CTGTAGGTAT  4920
CTCAGTTCGG  TGTAGGTCGT  TCGCTCCAAG  CTGGGCTGTG  TGCACGAACC  CCCCGTTCAG  4980
CCCGACCGCT  GCGCCTTATC  CGGTAACTAT  CGTCTTGAGT  CCAACCCGGT  AAGACACGAC  5040
TTATCGCCAC  TGGCAGCAGC  CACTGGTAAC  AGGATTAGCA  GAGCGAGGTA  TGTAGGCGGT  5100
GCTACAGAGT  TCTTGAAGTG  GTGGCCTAAC  TACGGCTACA  CTAGAAGGAC  AGTATTTGGT  5160
ATCTGCGCTC  TGCTGAAGCC  AGTTACCTTC  GGAAAAAGAG  TTGGTAGCTC  TTGATCCGGC  5220
AAACAAACCA  CCGCTGGTAG  CGGTGGTTTT  TTTGTTTGCA  AGCAGCAGAT  TACGCGCAGA  5280
AAAAAGGAT   CTCAAGAAGA  TCCTTTGATC  TTTTCTACGG  GGTCTGACGC  TCAGTGGAAC  5340
GAAAACTCAC  GTTAAGGGAT  TTTGGTCATG  AGATTATCAA  AAAGGATCTT  CACCTAGATC  5400
CTTTTAAATT  AAAAATGAAG  TTTTAAATCA  ATCTAAAGTA  TATATGAGTA  AACTTGGTCT  5460
GACAGTTACC  AATGCTTAAT  CAGTGAGGCA  CCTATCTCAG  CGATCTGTCT  ATTTCGTTCA  5520
TCCATAGTTG  CCTGACTCCC  CGTCGTGTAG  ATAACTACGA  TACGGGAGGG  CTTACCATCT  5580
GGCCCCAGTG  CTGCAATGAT  ACCGCGAGAC  CCACGCTCAC  CGGCTCCAGA  TTTATCAGCA  5640
ATAAACCAGC  CAGCCGGAAG  GGCCGAGCGC  AGAAGTGGTC  CTGCAACTTT  ATCCGCCTCC  5700
ATCCAGTCTA  TTAATTGTTG  CCGGGAAGCT  AGAGTAAGTA  GTTCGCCAGT  TAATAGTTTG  5760
CGCAACGTTG  TTGCCATTGC  TGCAGGCATC  GTGGTGTCAC  GCTCGTCGTT  TGGTATGGCT  5820
TCATTCAGCT  CCGGTTCCCA  ACGATCAAGG  CGAGTTACAT  GATCCCCCAT  GTTGTGCAAA  5880
AAAGCGGTTA  GCTCCTTCGG  TCCTCCGATC  GTTGTCAGAA  GTAAGTTGGC  CGCAGTGTTA  5940
TCACTCATGG  TTATGGCAGC  ACTGCATAAT  TCTCTTACTG  TCATGCCATC  CGTAAGATGC  6000
TTTTCTGTGA  CTGGTGAGTA  CTCAACCAAG  TCATTCTGAG  AATAGTGTAT  GCGGCGACCG  6060
AGTTGCTCTT  GCCCGGCGTC  AACACGGGAT  AATACCGCGC  CACATAGCAG  AACTTTAAAA  6120
GTGCTCATCA  TTGGAAAACG  TTCTTCGGGG  CGAAAACTCT  CAAGGATCTT  ACCGCTGTTG  6180
AGATCCAGTT  CGATGTAACC  CACTCGTGCA  CCCAACTGAT  CTTCAGCATC  TTTTACTTTC  6240
ACCAGCGTTT  CTGGGTGAGC  AAAAACAGGA  AGGCAAAATG  CCGCAAAAAA  GGGAATAAGG  6300
GCGACACGGA  AATGTTGAAT  ACTCATACTC  TTCCTTTTTC  AATATTATTG  AAGCATTTAT  6360
CAGGGTTATT  GTCTCATGAG  CGGATACATA  TTTGAATGTA  TTTAGAAAAA  TAAACAAATA  6420
GGGGTTCCGC  GCACATTTCC  CCGAAAAGTG  CCACCTGACG  TCTAAGAAAC  CATTATTATC  6480
ATGACATTAA  CCTATAAAAA  TAGGCGTATC  ACGAGGCCCT  TTCGTCTTCA  AGAATTCTCA  6540
TGTTTGACAG  CTTATCGATC  CGGCCAACGG  TGTTGCCATT  GCTGCAGGCG  CAGAGCTGGT  6600
AGGTATGGAA  GATCTATACA  GTG                                             6623
```

( 2 ) INFORMATION FOR SEQ ID NO:37:

( i ) SEQUENCE CHARACTERISTICS:
        ( A ) LENGTH: 6630 base pairs
        ( B ) TYPE: nucleic acid
        ( C ) STRANDEDNESS: both
        ( D ) TOPOLOGY: circular ( i i ) MOLECULE TYPE:

( x i ) SEQUENCE DESCRIPTION: SEQ ID NO:37:

```
AATCAATATT  GGCAATTAGC  CATATTAGTC  ATTGGTTATA  TAGCATGAAT  CAATATTGGC   60
TATTGGCCAT  TGCATACGTT  GTATCTATAT  CATAATATGT  ACATTTATAT  TGGCTCATGT  120
CCAATATGAC  CGCCATGTTG  ACATTGATTA  TTGACTAGTT  ATTAATAGTA  ATCAATTACG  180
```

```
GGGTCATTAG  TTCATAGCCC  ATATATGGAG  TTCCGCGTTA  CATAACTTAC  GGTAAATGGC   240

CCGCCTGGCT  GACCGCCCAA  CGACCCCCGC  CCATTGACGT  CAATAATGAC  GTATGTTCCC   300

ATAGTAACGC  CAATAGGGAC  TTTCCATTGA  CGTCAATGGG  TGGAGTATTT  ACGGTAAACT   360

GCCCACTTGG  CAGTACATCA  AGTGTATCAT  ATGCCAAGTA  CGCCCCCTAT  TGACGTCAAT   420

GACGGTAAAT  GGCCCGCCTG  GCATTATGCC  CAGTACATGA  CCTTATGGGA  CTTTCCTACT   480

TGGCAGTACA  TCTACGTATT  AGTCATCGCT  ATTACCATGG  TGATGCGGTT  TTGGCAGTAC   540

ATCAATGGGC  GTGGATAGCG  GTTTGACTCA  CGGGGATTTC  CAAGTCTCCA  CCCCATTGAC   600

GTCAATGGGA  GTTTGTTTTG  GCACCAAAAT  CAACGGGACT  TTCCAAAATG  TCGTAACAAC   660

TCCGCCCCAT  TGACGCAAAT  GGGCGGTAGG  CGTGTACGGT  GGGAGGTCTA  TATAAGCAGA   720

GCTCTCTGGC  TAACTAGAGA  ACCCACTGCT  TACTGGCTTA  TCGAAATTAA  TACGACTCAC   780

TATAGGGAGA  CCCAAGCTCT  AGAGAATTCG  CGGCTCGAGG  TACCGGATCC  ATCGATGTCG   840

ACCTGCAGAA  GCTTGCTAGA  GGATCTTTGT  GAAGGAACCT  TACTTCTGTG  GTGTGACATA   900

ATTGGACAAA  CTACCTACAG  AGATTTAAAG  CTCTAAGGTA  AATATAAAAT  TTTTAAGTGT   960

ATAATGTGTT  AAACTACTGA  TTCTAATTGT  TTGTGTATTT  TAGATTCCAA  CCTATGGAAC  1020

TGATGAATGG  GAGCAGTGGT  GGAATGCCTT  TAATGAGGAA  AACCTGTTTT  GCTCAGAAGA  1080

AATGCCATCT  AGTGATGATG  AGGCTACTGC  TGACTCTCAA  CATTCTACTC  CTCCAAAAAA  1140

GAAGAGAAAG  GTAGAAGACC  CCAAGGACTT  TCCTTCAGAA  TTGCTAAGTT  TTTTGAGTCA  1200

TGCTGTGTTT  AGTAATAGAA  CTCTTGCTTG  CTTTGCTATT  TACACCACAA  AGGAAAAAGC  1260

TGCACTGCTA  TACAAGAAAA  TTATGGAAAA  ATATTTGATG  TATAGTGCCT  TGACTAGAGA  1320

TCATAATCAG  CCATACCACA  TTTGTAGAGG  TTTTACTTGC  TTTAAAAAAC  CTCCCACACC  1380

TCCCCCTGAA  CCTGAAACAT  AAAATGAATG  CAATTGTTGT  TGTTAACTTG  TTTATTGCAG  1440

CTTATAATGG  TTACAAATAA  AGCAATAGCA  TCACAAATTT  CACAAATAAA  GCATTTTTTT  1500

CACTGCATTC  TAGTTGTGGT  TTGTCCAAAC  TCATCAATGT  ATCTTATCAT  GTCTGGATCA  1560

ATTCTGAGAA  ACTAGCCTTA  AAGACAGACA  GCTTTGTTCT  AGTCAGCCAG  GCAAGCATAT  1620

GTAAATAAAG  TTCCTCAGGG  AACTGAGGTT  AAAAGATGTA  TCCTGGACCT  GCCAGACCTG  1680

GCCATTCACG  TAAACAGAAG  ATTCCGCCTC  AAGTTCCGGT  TAACAACAGG  AGGCAACGAG  1740

ATCATCGCTG  TTCCTTAGGA  CCCTTTTACT  AACCCTAATT  CGATAGCATA  TGCTTCCCGT  1800

TGGGTAACAT  ATGCTATTGA  ATTAGGGTTA  GTCTGGATAG  TATATACTAC  TACCCGGGAA  1860

GCATATGCTA  CCCGTTTAGG  GTTAACAAGG  GGGCCTTATA  AACACTATTG  CTAATGCCCT  1920

CTTGAGGGTC  CGCTTATCGG  TAGCTACACA  GGCCCCTCTG  ATTGACGTTG  GTGTAGCCTC  1980

CCGTAGTCTT  CCTGGGCCCC  TGGGAGGTAC  ATGTCCCCCA  GCATTGGTGT  AAGAGCTTCA  2040

GCCAAGAGTT  ACACATAAAG  GCAATGTTGT  GTTGCAGTCC  ACAGACTGCA  AAGTCTGCTC  2100

CAGGATGAAA  GCCACTCAGT  GTTGGCAAAT  GTGCACATCC  ATTTATAAGG  ATGTCAACTA  2160

CAGTCAGAGA  ACCCCTTTGT  GTTTGGTCCC  CCCCGTGTC   ACATGTGGAA  CAGGGCCCAG  2220

TTGGCAAGTT  GTACCAACCA  ACTGAAGGGA  TTACATGCAC  TGCCCCGCGT  GAGCAATACA  2280

AAACAAAAGC  GCTCCTCGTA  CCAGCGAAGA  AGGGGCAGAG  ATGCCGTAGT  CAGGTTTAGT  2340

TCGTCCGGCG  GCGCCAGAAA  TCCGCGCGGT  GGTTTTGGG   GGTCGGGGT   GTTTGGCAGC  2400

CACAGACGCC  CGGTGTTCGT  GTCGCGCCAG  TACATGCGGT  CCATGCCCAG  GCCATCCAAA  2460

AACCATGGGT  CTGTCTGCTC  AGTCCAGTCG  TGGACCTGAC  CCCACGCAAC  GCCCAAAAGA  2520

ATAACCCCCA  CGAACCATAA  ACCATTCCCC  ATGGGGACC   CCGTCCCTAA  CCCACGGGGC  2580
```

```
CCGTGGCTAT GGCGGGCTTG CCGCCCCGAC GTTGGCTGCG AGCCCTGGGC CTTCACCCGA 2640
ACTTGGGGGT TGGGGTGGGG AAAAGGAAGA AACGCGGGCG TATTGGCCCC AATGGGGTCT 2700
CGGTGGGGTA TCGACAGAGT GCCAGCCCTG GGACCGAACC CCGCGTTTAT GAACAAACGA 2760
CCCAACACCC GTGCGTTTTA TTCTGTCTTT TTATTGCCGT CATAGCGCGG GTTCCTTCCG 2820
GTATTGTCTC CTTCCGTGTT TCAGTTAGCC TCCCCCATCT CCCGATCCCT ATTCCTTTGC 2880
CCTCGGACGA GTGCTGGGGC GTCGGTTTCC ACTATCGGCG AGTACTTCTA CACAGCCATC 2940
GGTCCAGACG GCCGCGCTTC TGCGGGCGAT TTGTGTACGC CCGACAGTCC CGGCTCCGGA 3000
TCGGACGATT GCGTCGCATC GACCCTGCGC CCAAGCTGCA TCATCGAAAT GCCGTCAAC 3060
CAAGCTCTGA TAGAGTTGGT CAAGACCAAT GCGGAGCATA TACGCCCGGA GCCGCGGCGA 3120
TCCTGCAAGC TCCGGATGCC TCCGCTCGAA GTAGCGCGTC TGCTGCTCCA TACAAGCCAA 3180
CCACGGCCTC CAGAAGAAGA TGTTGGCGAC CTCGTATTGG GAATCCCCGA ACATCGCCTC 3240
GCTCCAGTCA ATGACCGCTG TTATGCGGCC ATTGTCCGTC AGGACATTGT TGGAGCCGAA 3300
ATCCGCGTGC ACGAGGTGCC GGACTTCGGG GCAGTCCTCG GCCCAAAGCA TCAGCTCATC 3360
GAGAGCCTGC GCGACGGACG CACTGACGGT GTCGTCCATC ACAGTTTGCC AGTGATACAC 3420
ATGGGGATCA GCAATCGCGC ATATGAAATC ACGCCATGTA GTGTATTGAC CGATTCCTTG 3480
CGGTCCGAAT GGGCCGAACC CGCTCGTCTG GCTAAGATCG GCCGCAGCGA TCGCATCCAT 3540
GGCCTCCGCG ACCGGCTGCA GAACAGCGGG CAGTTCGGTT TCAGGCAGGT CTTGCAACGT 3600
GACACCCTGT GCACGGCGGG AGATGCAATA GGTCAGGCTC TCGCTGAATT CCCCAATGTC 3660
AAGCACTTCC GGAATCGGGA GCGCGGCCGA TGCAAAGTGC CGATAAACAT AACGATCTTT 3720
GTAGAAACCA TCGGCGCAGC TATTTACCCG CAGGACATAT CCACGCCCTC CTACATCGAA 3780
GCTGAAAGCA CGAGATTCTT CGCCCTCCGA GAGCTGCATC AGGTCGGAGA CGCTGTCGAA 3840
CTTTTCGATC AGAAACTTCT CGACAGACGT CGCGGTGAGT TCAGGCTTTT TCATATCTCA 3900
TTGCCCCCGG ACGAGGATCT GCGGCACGCT GTTGACGCTG TTAAGCGGGT CGCTGCAGGG 3960
TCGCTCGGTG TTCGAGGCCA CACGCGTCAC CTTAATATGC GAAGTGGACC TGGGACCGCG 4020
CCGCCCCGAC TGCATCTGCG TGTTCGAATT CGCCAATGAC AAGACGCTGG GCGGGGTTTG 4080
TGTCATCATA GAACTAAAGA CATGCAAATA TATTTCTTCC GGGGACACCG CCAGCAAACG 4140
CGAGCAACGG GCCACGGGGA TGAAGCAGGG CGGCACCTCG CTAACGGATT CACCACTCCA 4200
AGAATTGGAG CCAATCAATT CTTGCGGAGA ACTGTGAATG CGCAAACCAA CCCTTGGCAG 4260
AACATATCCA TCGCGTCCGC CATCTCCAGC AGCCGCACGC GGCGCATCTC GGGCAGCGTT 4320
GGGTCCTGGC CACGGGTGCG CATGATCGTG CTCCTGTCGT TGAGGACCCG GCTAGGCTGG 4380
CGGGGTTGCC TTACTGGTTA GCAGAATGAA TCACCGATAC GCGAGCGAAC GTGAAGCGAC 4440
TGCTGCTGCA AAACGTCTGC GACCTGAGCA ACAACATGAA TGGTCTTCGG TTTCCGTGTT 4500
TCGTAAAGTC TGGAAACGCG GAAGTCAGCG CTCTTCCGCT TCCTCGCTCA CTGACTCGCT 4560
GCGCTCGGTC GTTCGGCTGC GGCGAGCGGT ATCAGCTCAC TCAAAGGCGG TAATACGGTT 4620
ATCCACAGAA TCAGGGGATA ACGCAGGAAA GAACATGTGA GCAAAAGGCC AGCAAAAGGC 4680
CAGGAACCGT AAAAAGGCCG CGTTGCTGGC GTTTTTCCAT AGGCTCCGCC CCCCTGACGA 4740
GCATCACAAA AATCGACGCT CAAGTCAGAG GTGGCGAAAC CCGACAGGAC TATAAAGATA 4800
CCAGGCGTTT CCCCCTGGAA GCTCCCTCGT GCGCTCTCCT GTTCCGACCC TGCCGCTTAC 4860
CGGATACCTG TCCGCCTTTC TCCCTTCGGG AAGCGTGGCG CTTTCTCATA GCTCACGCTG 4920
TAGGTATCTC AGTTCGGTGT AGGTCGTTCG CTCCAAGCTG GGCTGTGTGC ACGAACCCCC 4980
```

-continued

| | | | | | | |
|---|---|---|---|---|---|---|
| CGTTCAGCCC | GACCGCTGCG | CCTTATCCGG | TAACTATCGT | CTTGAGTCCA | ACCCGGTAAG | 5040 |
| ACACGACTTA | TCGCCACTGG | CAGCAGCCAC | TGGTAACAGG | ATTAGCAGAG | CGAGGTATGT | 5100 |
| AGGCGGTGCT | ACAGAGTTCT | TGAAGTGGTG | GCCTAACTAC | GGCTACACTA | GAAGGACAGT | 5160 |
| ATTTGGTATC | TGCGCTCTGC | TGAAGCCAGT | TACCTTCGGA | AAAAGAGTTG | GTAGCTCTTG | 5220 |
| ATCCGGCAAA | CAAACCACCG | CTGGTAGCGG | TGGTTTTTTT | GTTTGCAAGC | AGCAGATTAC | 5280 |
| GCGCAGAAAA | AAAGGATCTC | AAGAAGATCC | TTTGATCTTT | TCTACGGGGT | CTGACGCTCA | 5340 |
| GTGGAACGAA | AACTCACGTT | AAGGGATTTT | GGTCATGAGA | TTATCAAAAA | GGATCTTCAC | 5400 |
| CTAGATCCTT | TTAAATTAAA | AATGAAGTTT | TAAATCAATC | TAAAGTATAT | ATGAGTAAAC | 5460 |
| TTGGTCTGAC | AGTTACCAAT | GCTTAATCAG | TGAGGCACCT | ATCTCAGCGA | TCTGTCTATT | 5520 |
| TCGTTCATCC | ATAGTTGCCT | GACTCCCCGT | CGTGTAGATA | ACTACGATAC | GGGAGGGCTT | 5580 |
| ACCATCTGGC | CCCAGTGCTG | CAATGATACC | GCGAGACCCA | CGCTCACCGG | CTCCAGATTT | 5640 |
| ATCAGCAATA | AACCAGCCAG | CCGGAAGGGC | CGAGCGCAGA | AGTGGTCCTG | CAACTTTATC | 5700 |
| CGCCTCCATC | CAGTCTATTA | ATTGTTGCCG | GGAAGCTAGA | GTAAGTAGTT | CGCCAGTTAA | 5760 |
| TAGTTTGCGC | AACGTTGTTG | CCATTGCTGC | AGGCATCGTG | GTGTCACGCT | CGTCGTTTGG | 5820 |
| TATGGCTTCA | TTCAGCTCCG | GTTCCCAACG | ATCAAGGCGA | GTTACATGAT | CCCCCATGTT | 5880 |
| GTGCAAAAAA | GCGGTTAGCT | CCTTCGGTCC | TCCGATCGTT | GTCAGAAGTA | AGTTGGCCGC | 5940 |
| AGTGTTATCA | CTCATGGTTA | TGGCAGCACT | GCATAATTCT | CTTACTGTCA | TGCCATCCGT | 6000 |
| AAGATGCTTT | TCTGTGACTG | GTGAGTACTC | AACCAAGTCA | TTCTGAGAAT | AGTGTATGCG | 6060 |
| GCGACCGAGT | TGCTCTTGCC | CGGCGTCAAC | ACGGGATAAT | ACCGCGCCAC | ATAGCAGAAC | 6120 |
| TTTAAAAGTG | CTCATCATTG | GAAAACGTTC | TTCGGGGCGA | AAACTCTCAA | GGATCTTACC | 6180 |
| GCTGTTGAGA | TCCAGTTCGA | TGTAACCCAC | TCGTGCACCC | AACTGATCTT | CAGCATCTTT | 6240 |
| TACTTTCACC | AGCGTTTCTG | GGTGAGCAAA | AACAGGAAGG | CAAAATGCCG | CAAAAAAGGG | 6300 |
| AATAAGGGCG | ACACGGAAAT | GTTGAATACT | CATACTCTTC | CTTTTTCAAT | ATTATTGAAG | 6360 |
| CATTTATCAG | GGTTATTGTC | TCATGAGCGG | ATACATATTT | GAATGTATTT | AGAAAAATAA | 6420 |
| ACAAATAGGG | GTTCCGCGCA | CATTTCCCCG | AAAAGTGCCA | CCTGACGTCT | AAGAAACCAT | 6480 |
| TATTATCATG | ACATTAACCT | ATAAAAATAG | GCGTATCACG | AGGCCCTTTC | GTCTTCAAGA | 6540 |
| ATTCTCATGT | TTGACAGCTT | ATCGATCCGG | CCAACGGTGT | TGCCATTGCT | GCAGGCGCAG | 6600 |
| AGCTGGTAGG | TATGGAAGAT | CTATACAGTG | | | | 6630 |